(12) United States Patent
Jang et al.

(10) Patent No.: US 8,173,272 B2
(45) Date of Patent: *May 8, 2012

(54) DIAMINE DERIVATIVES, PREPARATION METHOD THEREOF AND ORGANIC ELECTRONIC DEVICE USING THE SAME

(75) Inventors: Hye-Young Jang, Daejeon Metropolitan (KR); Jae-Chol Lee, Daejeon Metropolitan (KR); Jin-Kyoon Park, Daejeon Metropolitan (KR); Kong-Kyeom Kim, Daejeon Metropolitan (KR); Ji-Eun Kim, Daejeon Metropolitan (KR); Tae-Yoon Park, Daejeon Metropolitan (KR); Sung-Kil Hong, Daejeon Metropolitan (KR); Sang-Young Jeon, Daejeon Metropolitan (KR); Dong-Seob Jeong, Daejeon Metropolitan (KR)

(73) Assignee: LG Chem, Ltd., Seoul (KR)

( * ) Notice: Subject to any disclaimer, the term of this patent is extended or adjusted under 35 U.S.C. 154(b) by 726 days.

This patent is subject to a terminal disclaimer.

(21) Appl. No.: 12/225,483

(22) PCT Filed: Mar. 23, 2007

(86) PCT No.: PCT/KR2007/001448
§ 371 (c)(1),
(2), (4) Date: Sep. 23, 2008

(87) PCT Pub. No.: WO2007/108666
PCT Pub. Date: Sep. 27, 2007

(65) Prior Publication Data
US 2009/0134781 A1    May 28, 2009

(30) Foreign Application Priority Data

Mar. 23, 2006  (KR) .......................... 10-2006-0026468

(51) Int. Cl.
*H01L 51/54* (2006.01)
(52) U.S. Cl. ........ 428/690; 428/917; 313/504; 313/505; 313/506; 564/426; 564/434
(58) Field of Classification Search .................. 428/690, 428/917; 313/504, 505, 506; 464/426, 434
See application file for complete search history.

(56) References Cited

U.S. PATENT DOCUMENTS

| 5,811,834 | A | 9/1998 | Tamano et al. | |
| 6,737,532 | B2 * | 5/2004 | Chen et al. ..................... | 548/156 |
| 2004/0137270 | A1 * | 7/2004 | Seo et al. ....................... | 428/690 |

(Continued)

FOREIGN PATENT DOCUMENTS

EP    0 786 926 A2    7/1997

(Continued)

*Primary Examiner* — Jennifer Chriss
*Assistant Examiner* — Gregory Clark
(74) *Attorney, Agent, or Firm* — McKenna Long & Aldridge LLP

(57) ABSTRACT

The present invention relates to a novel diamine derivative, a method for preparation thereof, and an organic electronic device using the same. The diamine derivative according to the present invention can serve as a hole injecting, hole transporting, electron injecting, electron transporting, or light emitting material in an organic electronic device including an organic light emitting device. Particularly, it can be used as a light emitting material as used alone, and also serve as a light emitting host, or a light emitting dopant, in particular, a blue light emitting dopant. The organic electronic device according to the present invention exhibits excellent characteristics in terms of efficiency, drive voltage, life time, and stability.

13 Claims, 1 Drawing Sheet

U.S. PATENT DOCUMENTS

| | | |
|---|---|---|
| 2004/0209118 A1* | 10/2004 | Seo et al. .................. 428/690 |
| 2005/0067951 A1 | 3/2005 | Richter et al. |
| 2008/0220285 A1 | 9/2008 | Vestweber et al. |

FOREIGN PATENT DOCUMENTS

| | | |
|---|---|---|
| EP | 1 775 334 A1 | 4/2007 |
| JP | 09-268283 A | 10/1997 |
| JP | 2002184575 A | 6/2002 |
| JP | 2003213002 A | 7/2003 |
| JP | 2003238534 A | 8/2003 |
| JP | 2004-204238 A | 7/2004 |
| JP | 2004253298 A | 9/2004 |
| JP | 2005-516059 A | 6/2005 |
| JP | 2009-502778 A | 1/2009 |
| KR | 1020060115951 A | 11/2006 |
| WO | WO 2004/078872 A2 | 9/2004 |
| WO | WO 2006/121237 A1 | 11/2006 |
| WO | WO 2006/122630 A1 | 11/2006 |
| WO | WO 2007/105917 A1 | 9/2007 |

* cited by examiner

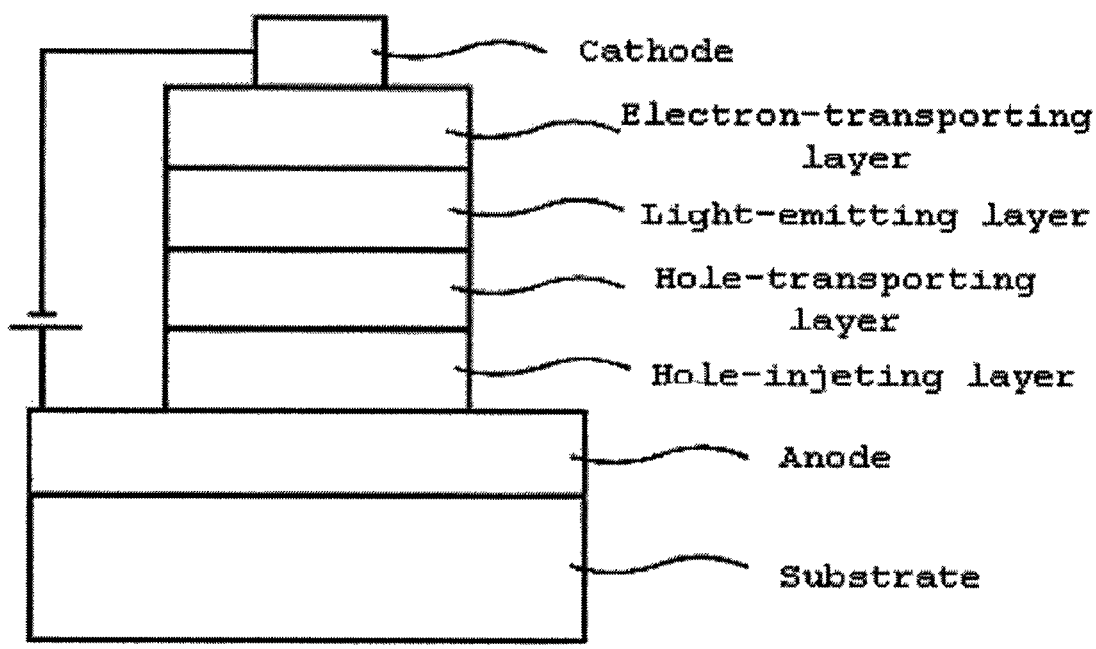

DIAMINE DERIVATIVES, PREPARATION METHOD THEREOF AND ORGANIC ELECTRONIC DEVICE USING THE SAME

This application is a 371 national stage entry of International Application No. PCT/KR2007/001448, filed on Mar. 23, 2007 that claims priority to Korean Patent Application No. 10-2006-0026468, filed on Mar. 23, 2006, both of which are hereby incorporated by reference in their entirety.

TECHNICAL FIELD

The present invention relates to a novel diamine derivative, a method for preparation thereof, and an organic electronic device using the same.

This application claims priority benefits from Korean Patent Application No. 10-2006-0026468, filed on Mar. 23, 2006, the entire contents of which are fully incorporated herein by reference.

BACKGROUND ART

The organic electronic device refers to a device which requires charge exchange between an electrode and an organic material using holes and electrons. The organic electronic device can be largely classified into two types according to its operation principle as follows. One type is an electronic device having a configuration in which an exciton is formed in an organic material layer by photons flown from an external light source into the device and the exciton is separated into an electron and a hole, the formed electron and hole are transported to a different electrode, respectively and used as a current source (voltage source), and the other type is an electronic device having a configuration in which a hole and/or electron are/is injected into an organic material semiconductor forming an interface with an electrode by applying a voltage or current to two or more electrodes to allow the device to operate by means of the injected electron and hole.

Examples of the organic electronic device include an organic light emitting device, an organic solar cell, an organic photoconductor (OPC) drum and an organic transistor, which all require a hole injecting or hole transporting material, an electron injecting or electron transporting material, or a light emitting material for driving the device.

Hereinafter, the organic light emitting device will be mainly and specifically described, but in the above-mentioned organic electronic devices, the hole injecting or hole transporting material, the electron injecting or electron transporting material, or the light emitting material injection functions according to a similar principle.

In general, the term "organic light emitting phenomenon" refers to a phenomenon in which electric energy is converted to light energy by means of an organic material. The organic light emitting device using the organic light emitting phenomenon has a structure usually comprising an anode, a cathode and an organic material layer interposed therebetween. Herein, the organic material layer may be mostly formed in a multilayer structure comprising layers of different materials, for example, the hole injecting layer, the hole transporting layer, the light emitting layer, the electron transporting layer, the electron injecting layer and the like, in order to improve efficiency and stability of the organic light emitting device. In the organic light emitting device having such a structure, when a voltage is applied between two electrodes, holes from the anode and electrons from a cathode are injected into the organic material layer, the holes and the electrons injected are combined together to form excitons. Further, when the excitons drop to a ground state, lights are emitted. Such the organic light emitting device is known to have characteristics such as self-luminescence, high brightness, high efficiency, low drive voltage, wide viewing angle, high contrast and high-speed response.

The materials used for the organic material layer of the organic light emitting device can be classified into a light emitting material and a charge transporting material, for example, a hole injecting material, a hole transporting material, an electron transporting material and an electron injecting material, according to their functions. The light emitting material can be classified into a high molecular weight type and a low molecular weight type, according to their molecular weight, and divided into a fluorescent material from singlet excited states and a phosphorescent material from triplet excited states according to their light emitting mechanism. Further, the light emitting material can be classified into a blue, green or red light emitting material and a yellow or orange light emitting material required for giving more natural color, according to a light emitting color.

On the other hand, an efficiency of a device is lowered owing to maximum luminescence wavelength moved to a longer wavelength due to the interaction between the molecules, the deterioration of color purity and the reduction in light emitting efficiency when only one material is used for the light emitting material, and therefore a host/dopant system can be used as the light emitting material for the purpose of enhancing the color purity and the light emitting efficiency through energy transfer. It is based on the principle that if a small amount of a dopant having a smaller energy band gap than a host which forms a light emitting layer, excitons which are generated in the light emitting layer are transported to the dopant, thus emitting a light having a high efficiency. Here, since the wavelength of the host is moved according to the wavelength of the dopant, a light having a desired wavelength can be obtained according the kind of the dopant.

In order to allow the organic light emitting device to fully exhibit the above-mentioned excellent characteristics, a material constituting the organic material layer in the device, for example, a hole injecting material, a hole transporting material, a light emitting material, an electron transporting material and an electron injecting material should be essentially composed of a stable and efficient material. However, the development of a stable and efficient organic material layer material for the organic light emitting device has not yet been fully realized. Accordingly, the development of new materials is continuously desired. The development of such a material is equally required to the above-mentioned other organic electronic devices.

DISCLOSURE

Technical Problem

The present inventors found a novel diamine derivative, and further found that the diamine derivative can be used as a hole injecting, hole transporting, electron injecting, electron transporting or light emitting material, and exhibit effects of increased efficiency, lower operating voltage, increased lifetime, and higher stability of an organic electronic device when forming an organic material layer of the organic electronic device.

Technical Solution

Therefore, it is an object of the present invention to provide a novel diamine derivative, a method for preparation thereof, and an organic electronic device using the same.

ADVANTAGEOUS EFFECTS

The diamine derivative according to the present invention can serve as a hole injecting, hole transporting, electron injecting, electron transporting, or light emitting material in an organic electronic device including an organic light emitting device. Particularly, it can be used as a light emitting material as used alone, and also serve as a light emitting host, or a light emitting dopant, in particular, a blue light emitting dopant. The organic electronic device according to the present invention exhibits excellent characteristics in terms of efficiency, drive voltage, life time, and stability.

DESCRIPTION OF DRAWINGS

FIG. 1 illustrates the structure of the organic light emitting device according to one embodiment of the present invention.

BEST MODE

The present invention provides a diamine derivative represented by the following formula 1.

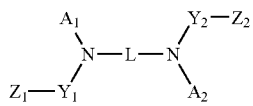
[Formula 1]

wherein

L is a $C_6$ to $C_{30}$ aryl group, $A_1$ and $A_2$ are the same or different from each other, and are each

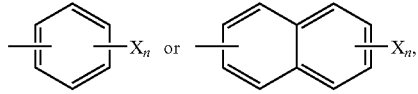

wherein n is an integer from 1 to 5, and at least one of Xs is selected from —GeRR'R", —SiRR'R" and deuterium (D), and the others are each independently selected from the group of consisting of hydrogen, CN, $NO_2$, a $C_6$ to $C_{20}$ arylamine group, a $C_6$ to $C_{20}$ arylthiophene group, a $C_3$ to $C_{20}$ cycloalkyl group, —OR, —SR, —SeR, —TeR, —BRR', —AlRR', —SnRR'R", a $C_6$ to $C_{20}$ aryl group, a $C_8$ to $C_{20}$ arylalkenyl group, and a $C_4$ to $C_{20}$ alkylene group which formed a fused ring with the phenyl group or the naphthyl group, $Y_1$ and $Y_2$ are the same or different from each other, and are each a $C_6$ to $C_{20}$ arylene group or a divalent $C_5$ to $C_{20}$ heterocyclic group, $Z_1$ and $Z_2$ are the same or different from each other, and are each hydrogen, halogen, deuterium, CN, $NO_2$, a $C_1$ to $C_{20}$ alkyl group, a $C_1$ to $C_{20}$ alkoxy group, a $C_6$ to $C_{20}$ aryl group, a $C_6$ to $C_{20}$ arylamine group, a $C_6$ to $C_{20}$ arylthiophene group, a $C_3$ to $C_{20}$ cycloalkyl group, —OR, —SR, —SeR, —TeR, —BRR', —AlRR', —SiRR'R", —GeRR'R", —SnRR'R", a $C_6$ to $C_{20}$ aryl group, a $C_8$ to $C_{20}$ arylalkenyl group, and a $C_4$ to $C_{20}$ alkylene group which formed a fused ring with the phenyl group or the naphthyl group, and R, R' and R" are the same or different from each other, and are each hydrogen, a $C_1$ to $C_{20}$ alkyl group, a $C_3$ to $C_{20}$ cycloalkyl group, a $C_6$ to $C_{20}$ aryl group, or a $C_5$ to $C_{20}$ heterocyclic group.

In the formula 1,

L is preferably selected from, for example, anthracenyl, phenanthrenyl, pyrenyl, perylenyl, chrysenyl,

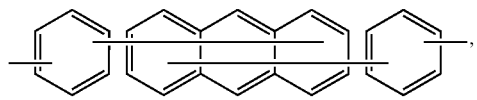

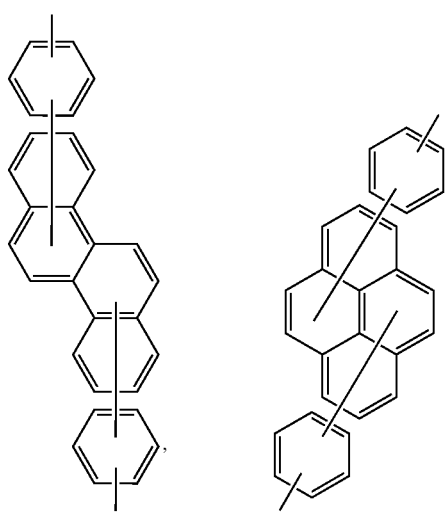
and

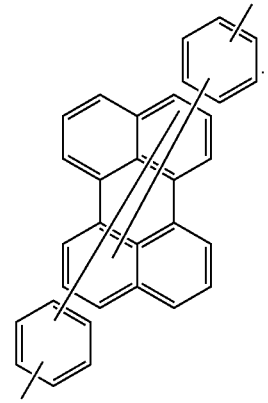

$Y_1$ and $Y_2$ are preferably selected from, for example, phenyl, biphenyl, naphthalenyl, tetralinyl, anthracenyl, stilbenyl, phenanthrenyl, pyrenyl, perylenyl, chrysenyl and carbazolyl, $Z_1$ and $Z_2$ are preferably selected from, for example, hydrogen, a $C_6$ to $C_{20}$ aryl group, a $C_6$ to $C_{20}$ arylamine group, —BRR', —SiRR'R", —GeRR'R" and a $C_4$ to $C_{20}$ alkylene group which formed a fused ring with the phenyl group or the naphthyl group, and R, R' and R" are each preferably, for example, a $C_1$ to $C_{20}$ alkyl group, or a $C_6$ to $C_{20}$ aryl group.

Specific examples of the compound of the formula 1 according to the present invention are shown in the following compounds, but are not limited thereto.

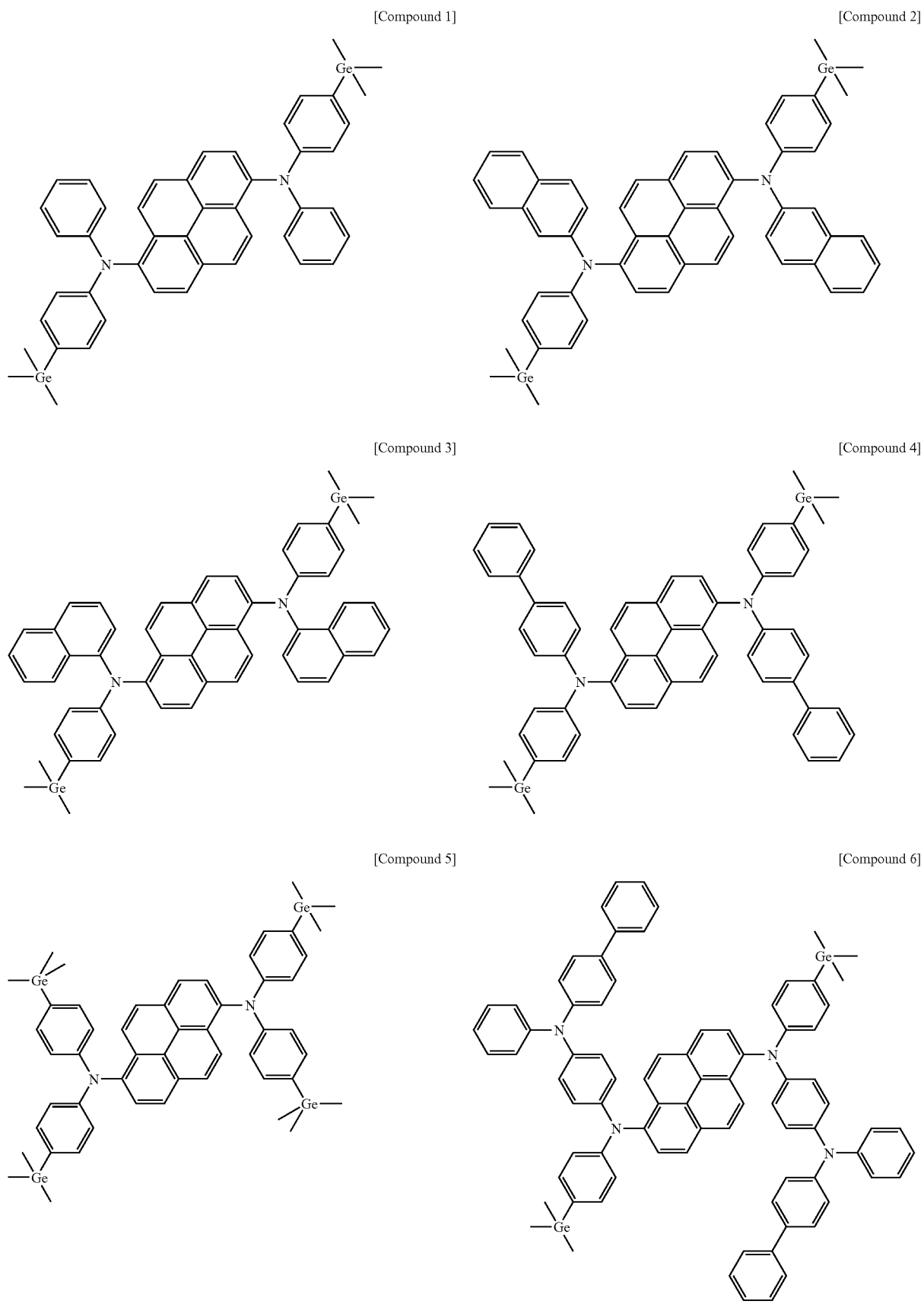

[Compound 7]
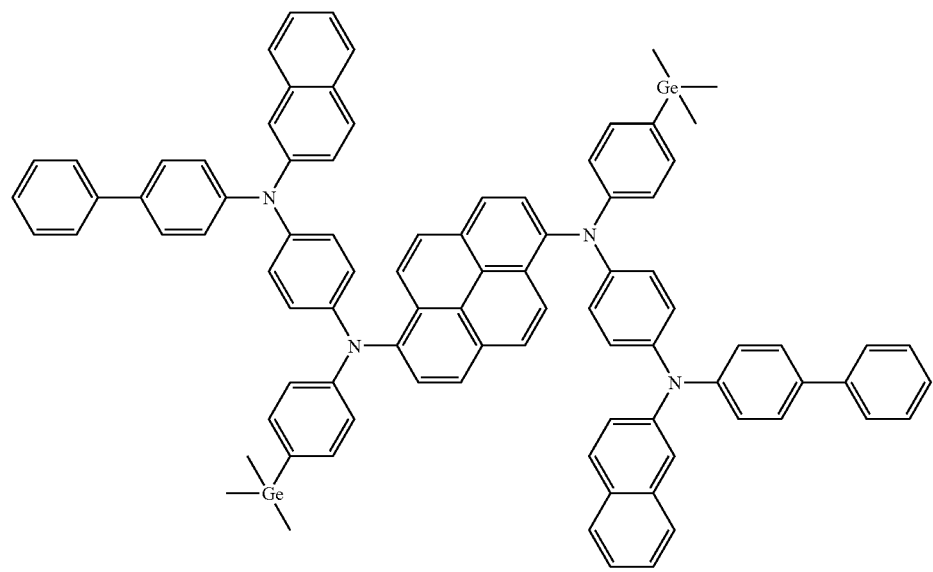
[Compound 8]
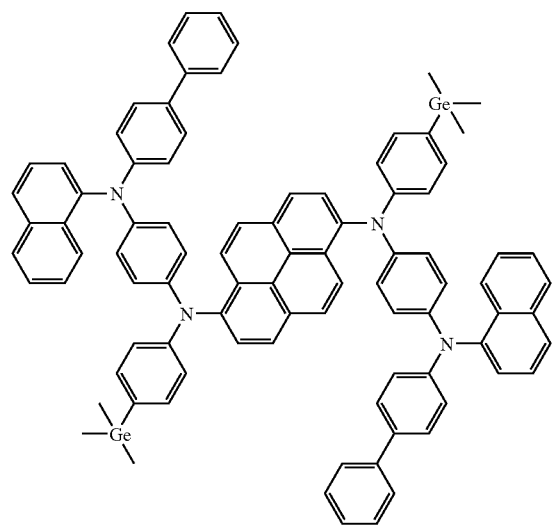
[Compound 9]
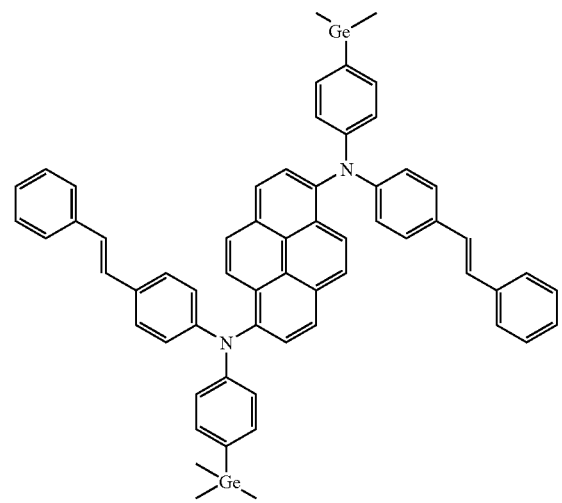
[Compound 10]
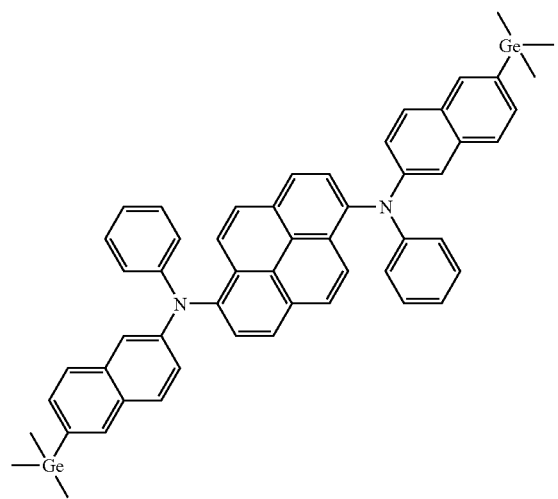
[Compound 11]
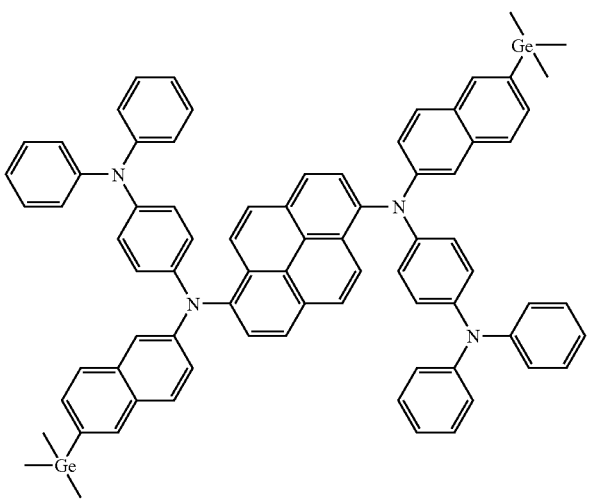

[Compound 12]
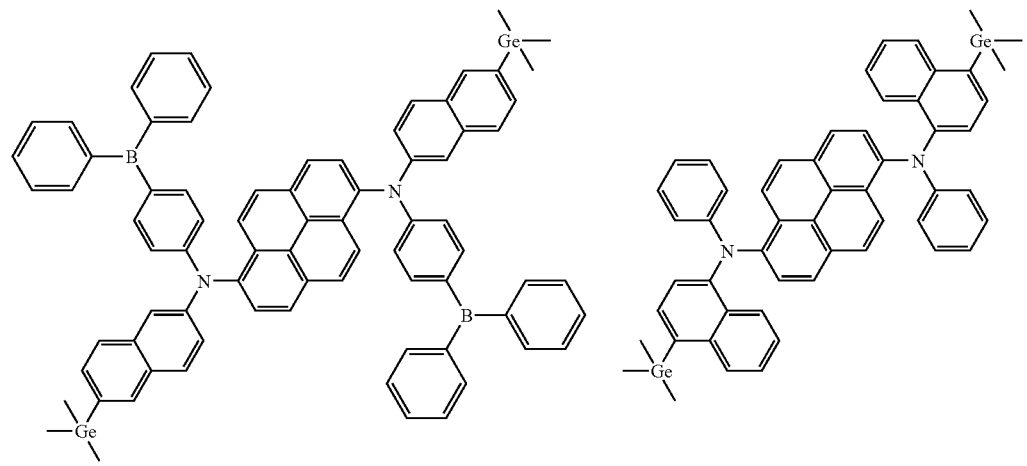
[Compound 13]
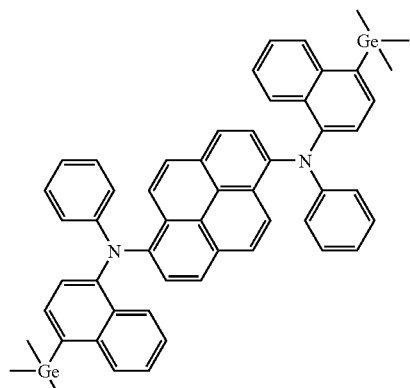
[Compound 14]
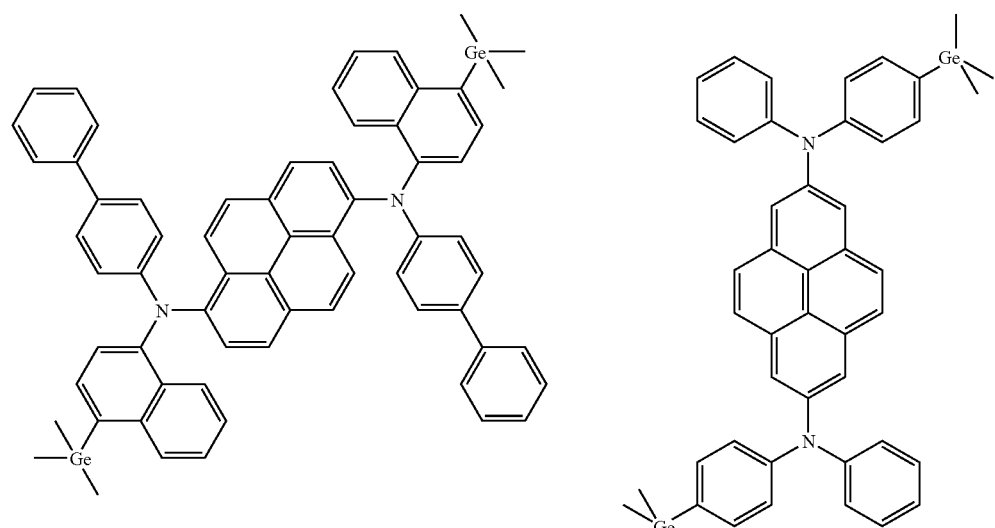
[Compound 15]
[Compound 16]
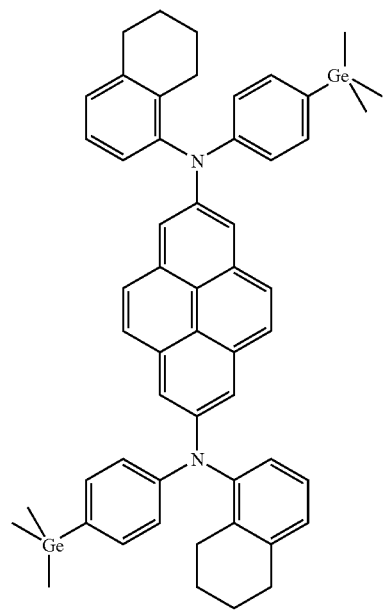
[Compound 17]
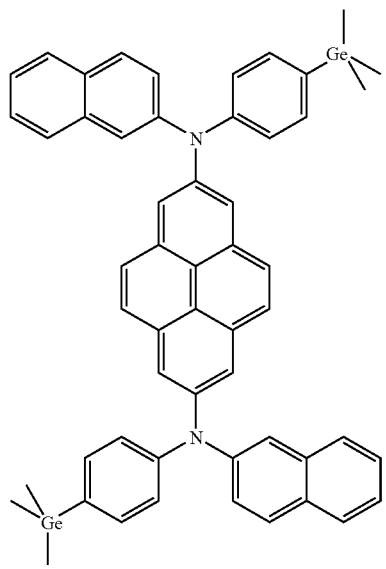

[Compound 18]
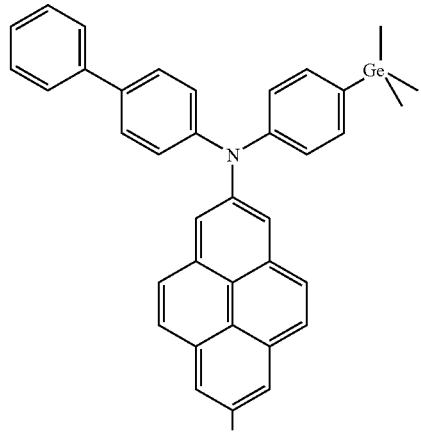
[Compound 19]
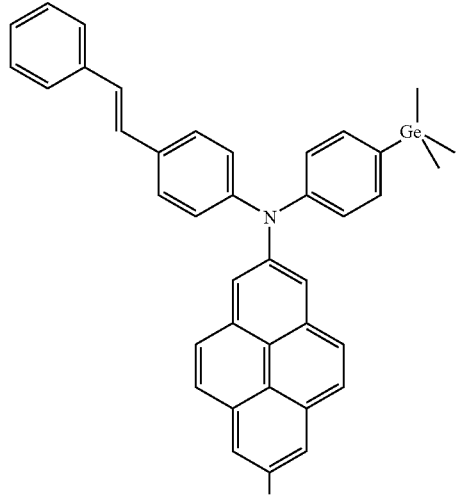
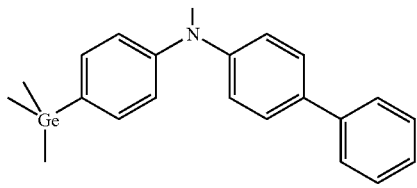
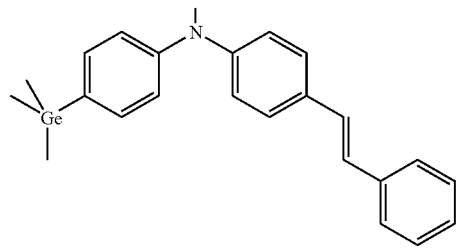
[Compound 20]
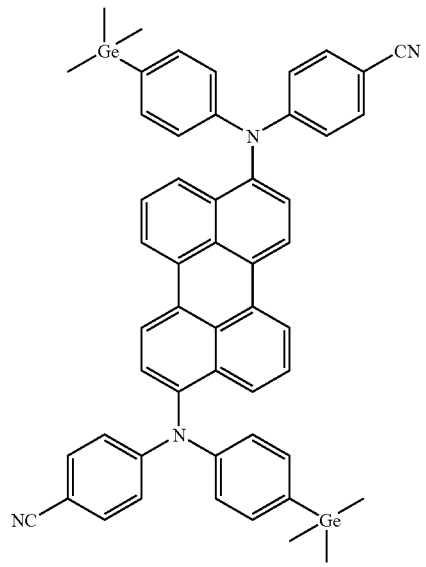
[Compound 21]
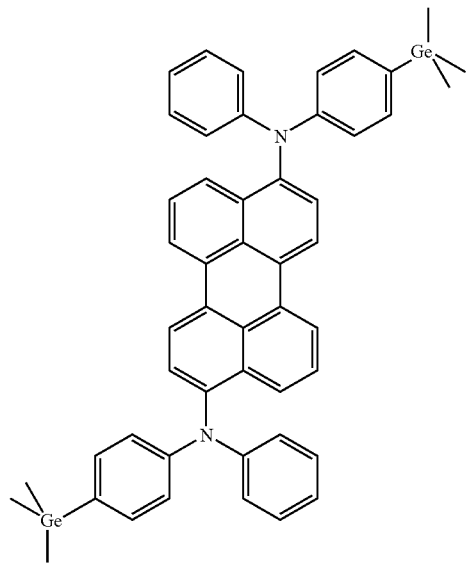

-continued
[Compound 22]
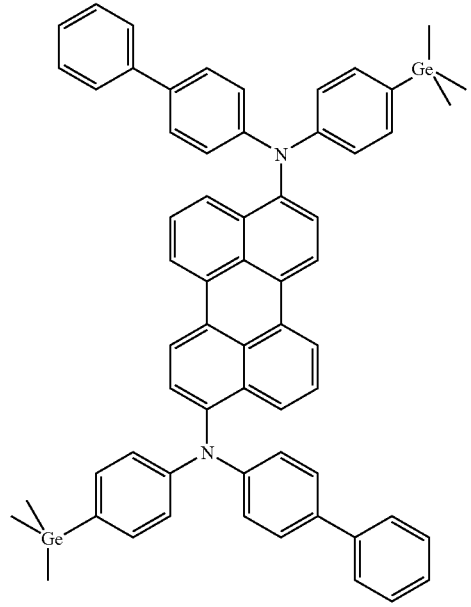
[Compound 23]
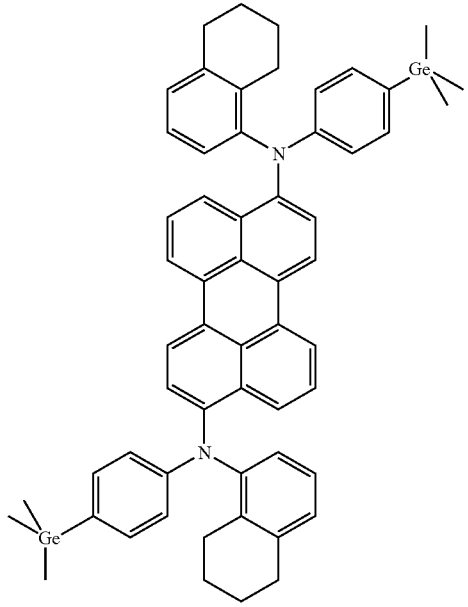
[Compound 24]
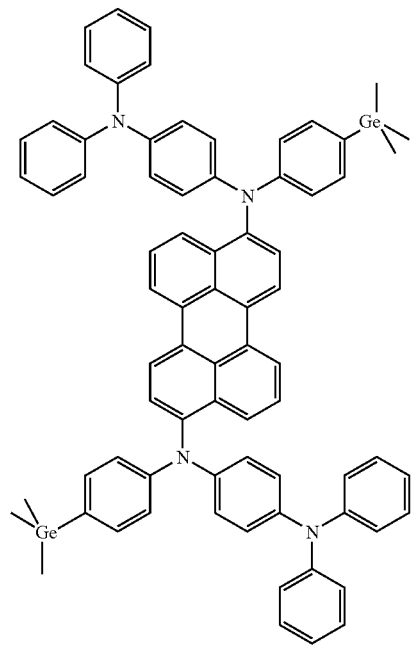
[Compound 25]
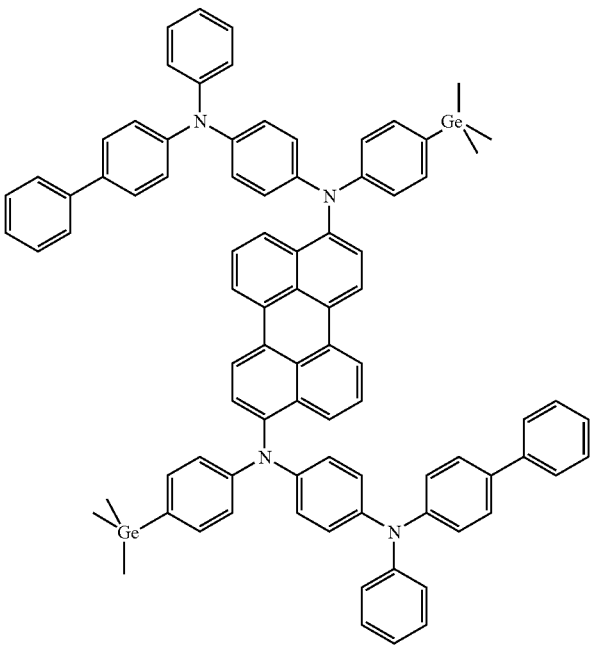

-continued
[Compound 26]
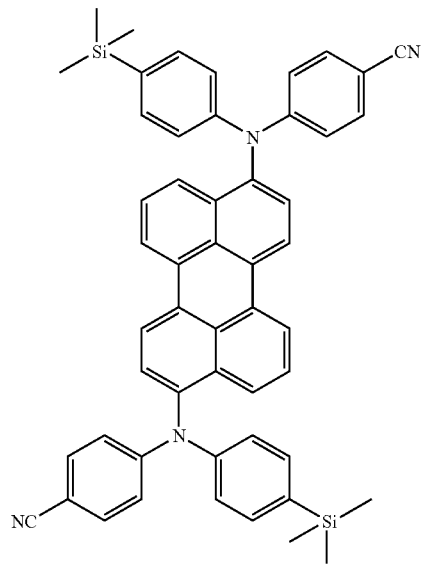
[Compound 27]
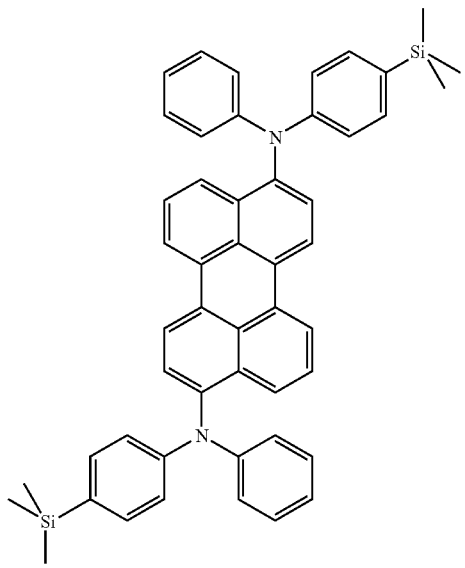
[Compound 28]
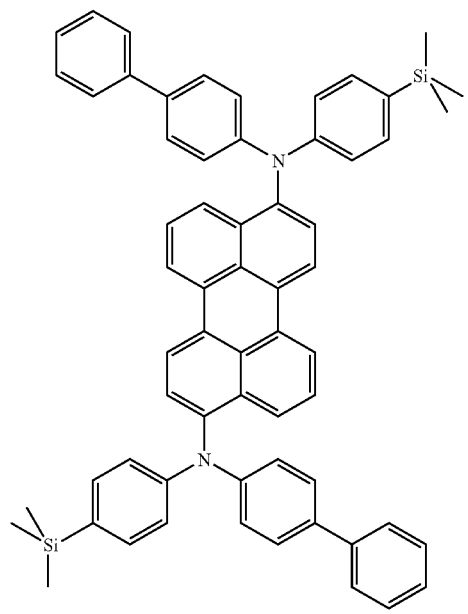
[Compound 29]
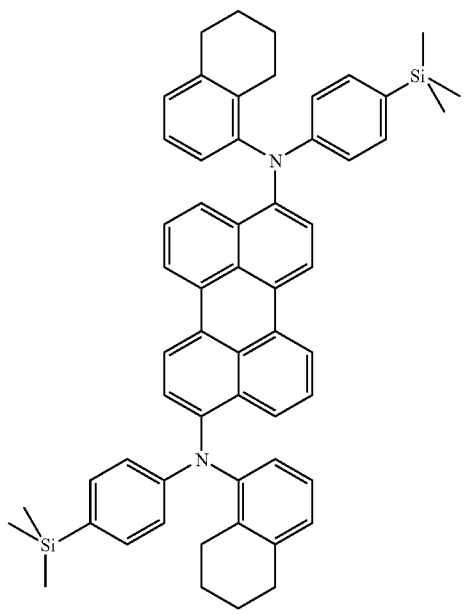
[Compound 30]
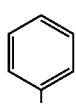
[Compound 31]

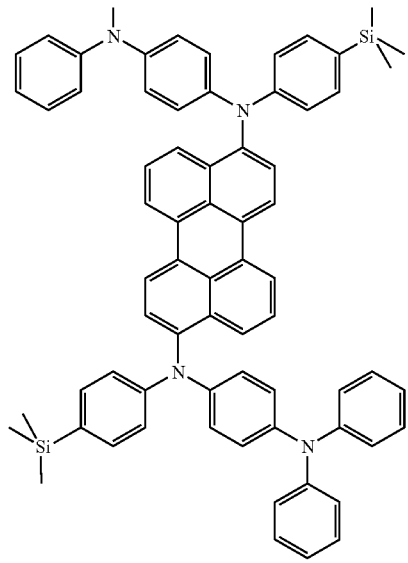
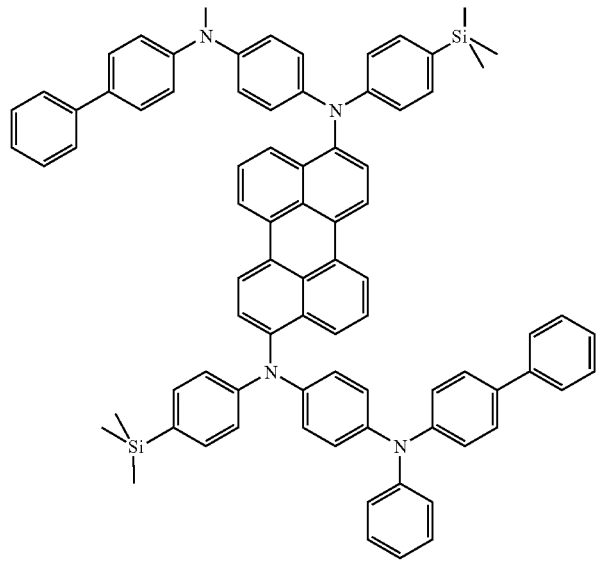
[Compound 32]
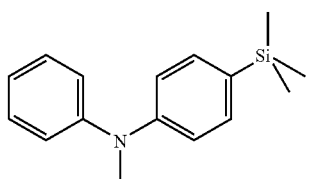
[Compound 33]
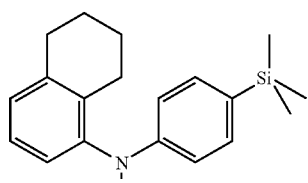
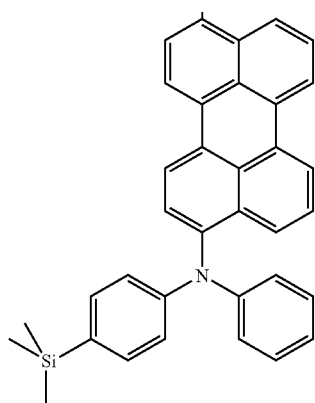
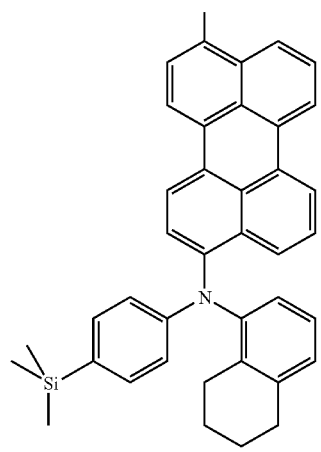

-continued
[Compound 34]
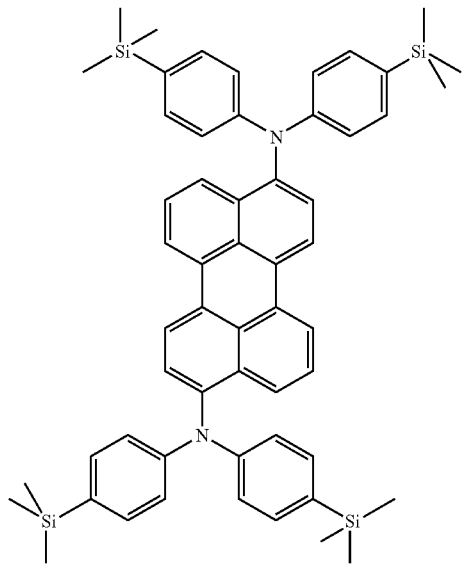
[Compound 35]
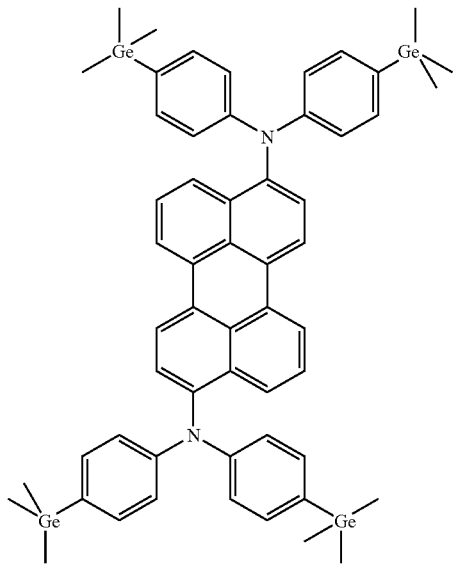
[Compound 36]
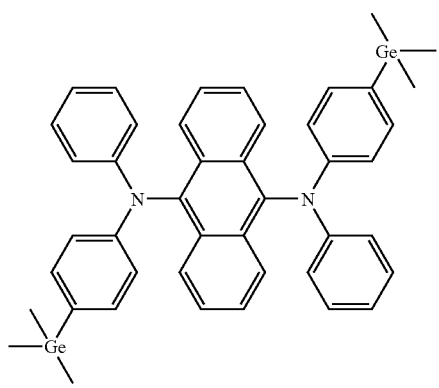
[Compound 37]
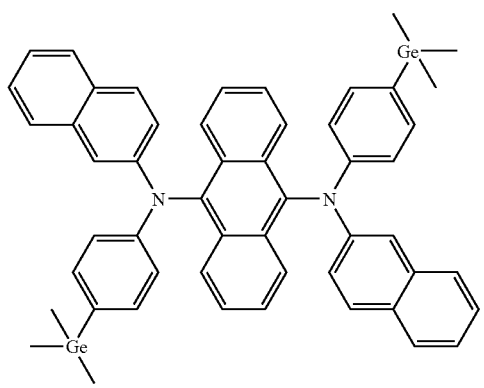
[Compound 38]
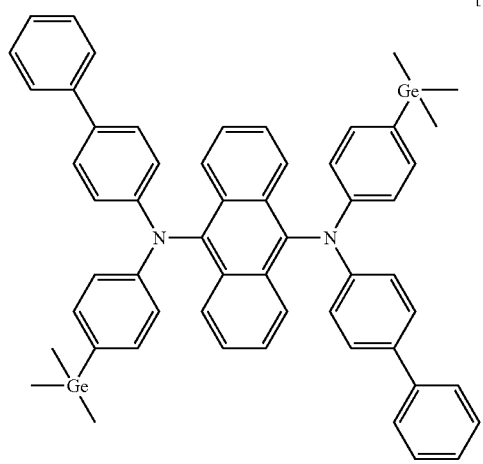
[Compound 39]
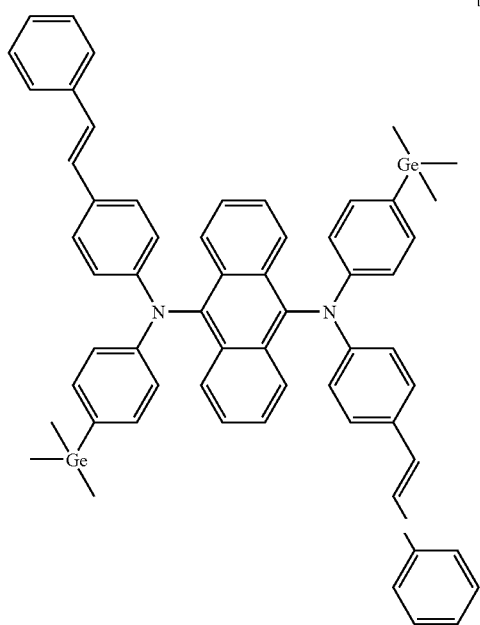

[Compound 40]
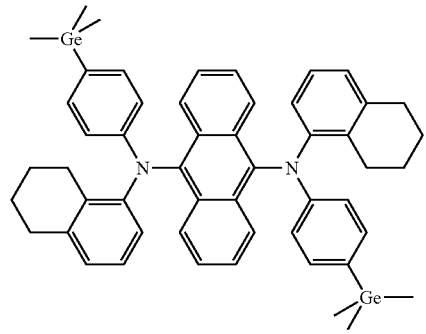
[Compound 41]
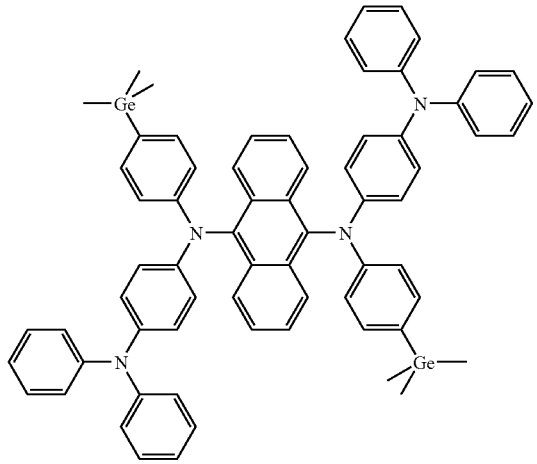
[Compound 42]
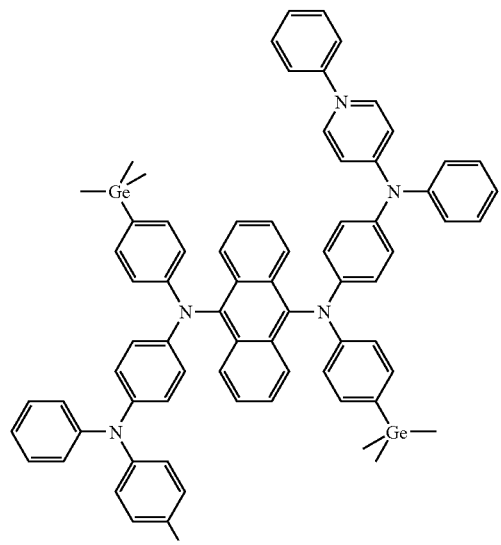
[Compound 43]
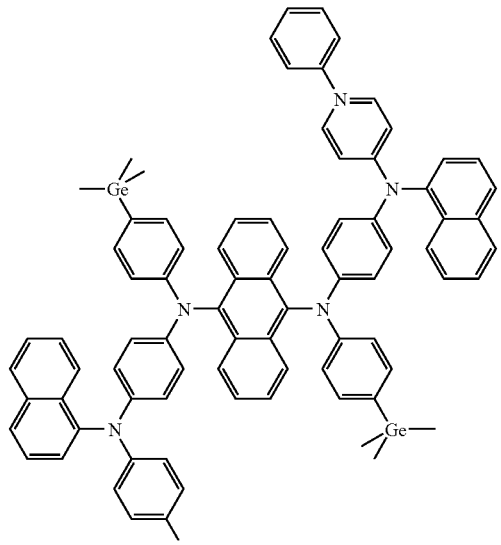
[Compound 44]
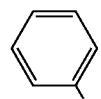

-continued
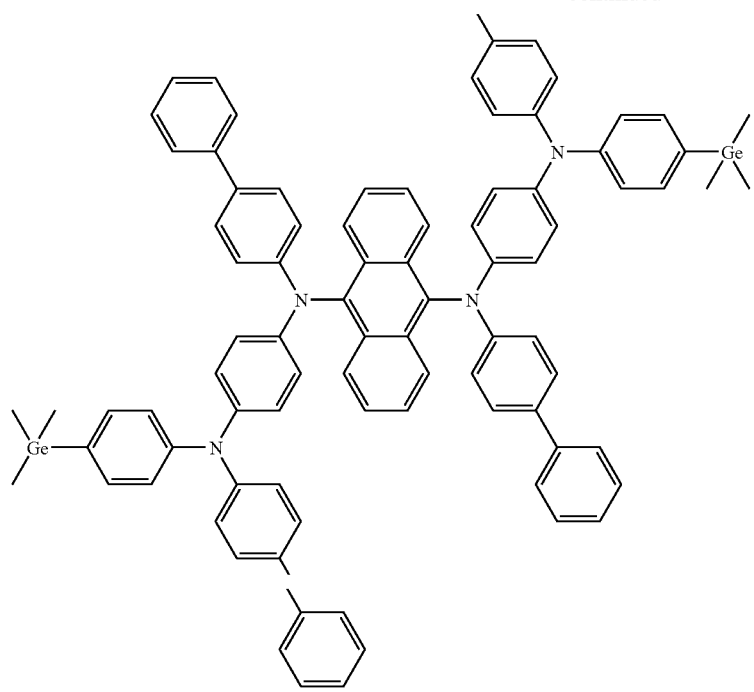
[Compound 45]
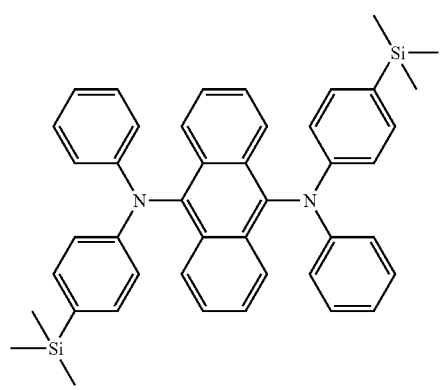
[Compound 46]
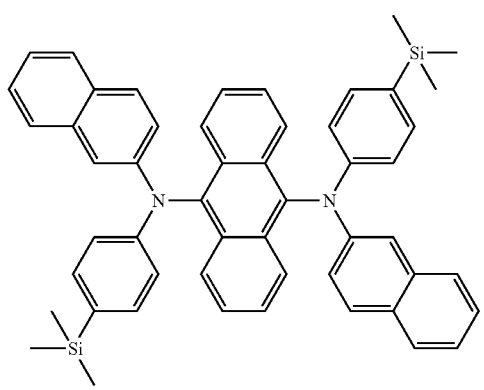
[Compound 47]
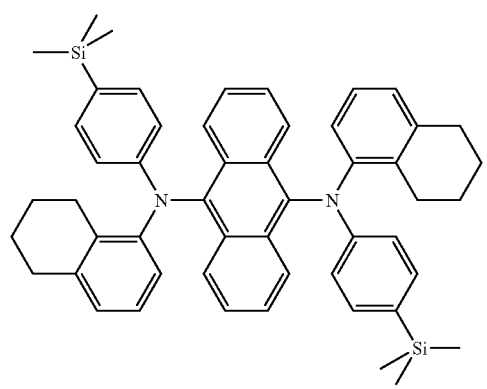
[Compound 48]
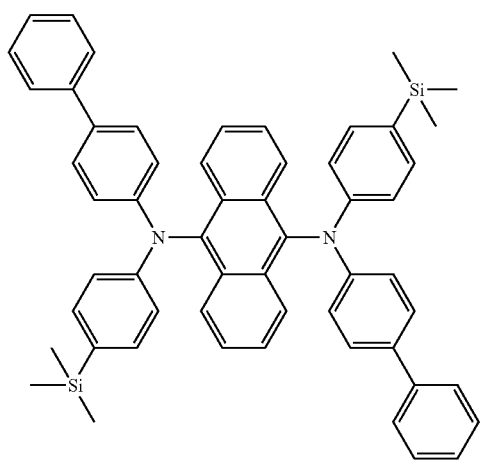

[Compound 49]
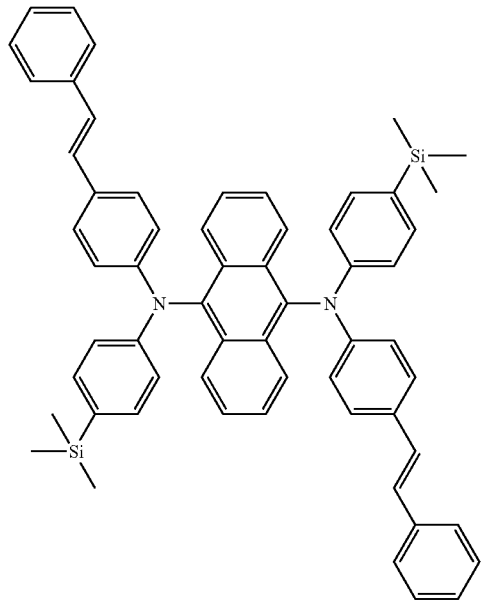
[Compound 50]
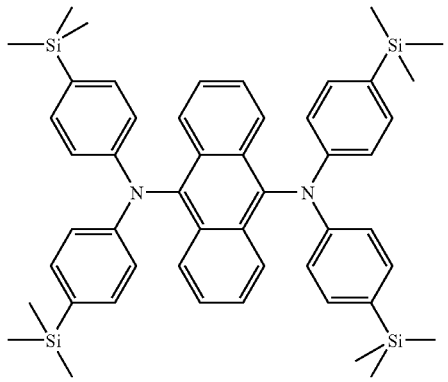
[Compound 51]
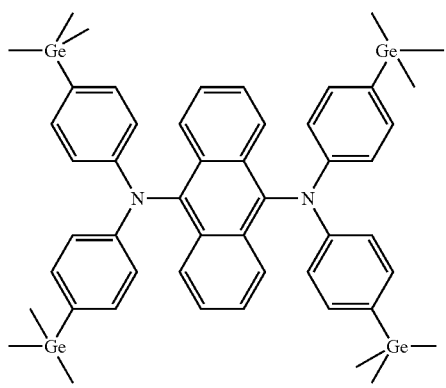
[Compound 52]
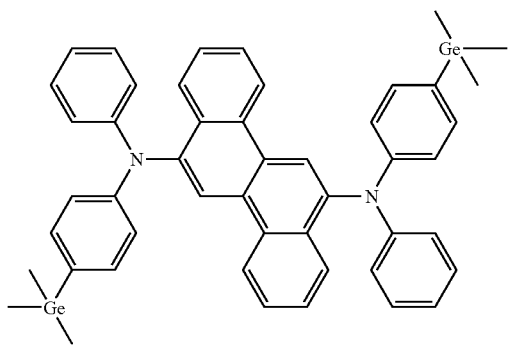
[Compound 53]
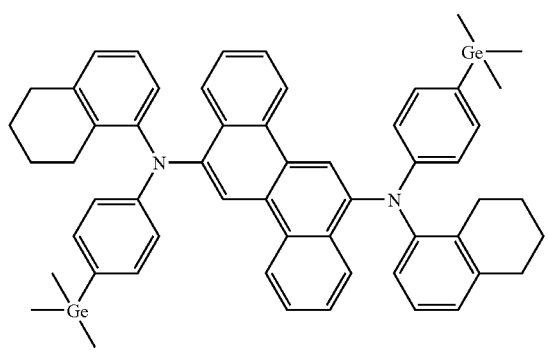
[Compound 54]
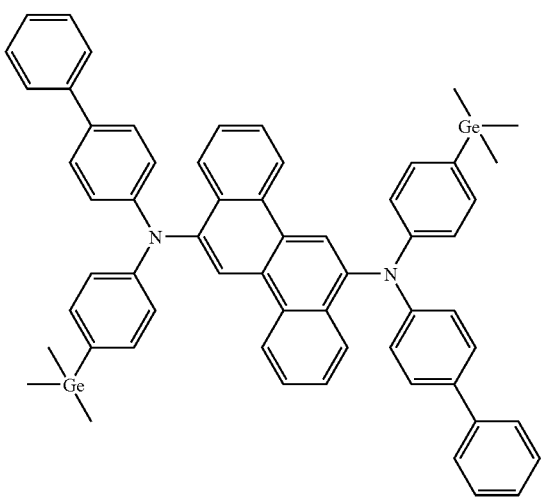

[Compound 55]
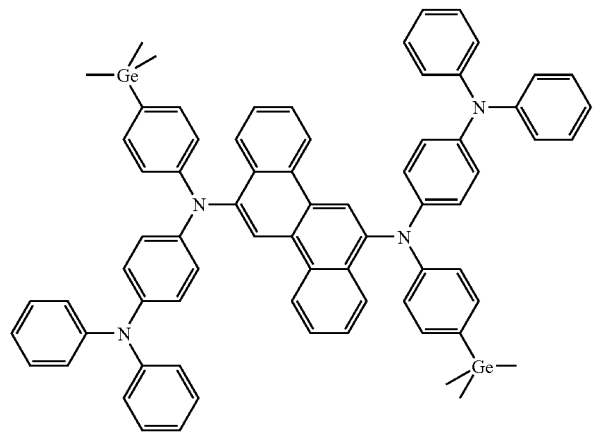
[Compound 56]
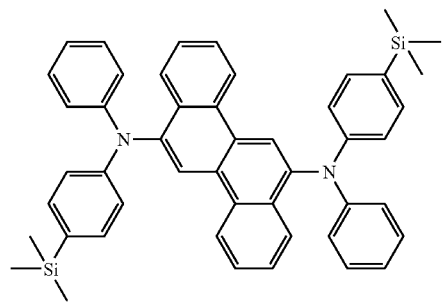
[Compound 57]
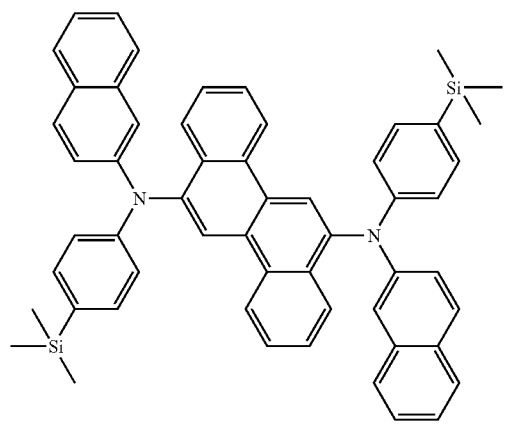
[Compound 58]
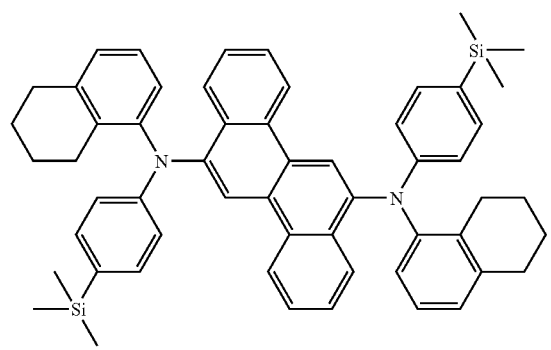
[Compound 59]
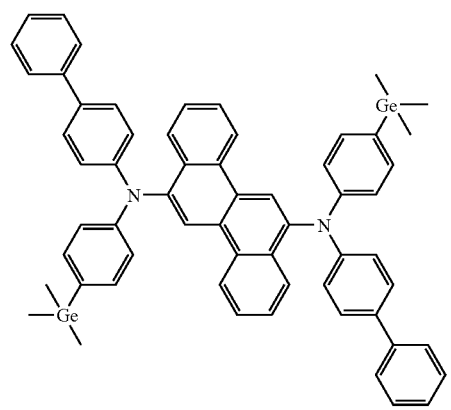
[Compound 60]
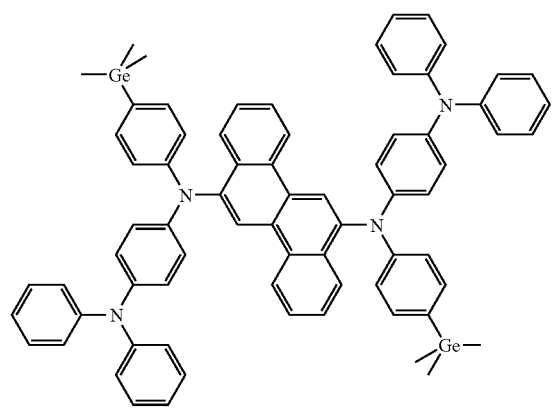

-continued
[Compound 61]
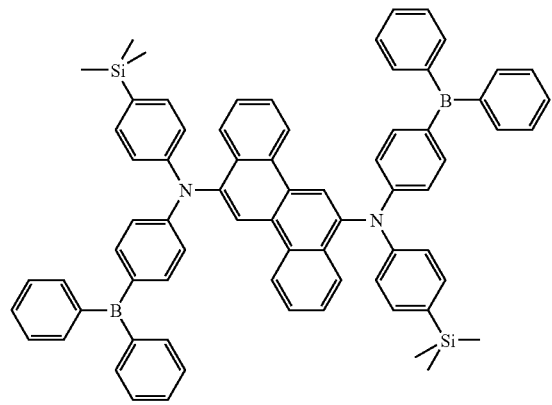
[Compound 62]
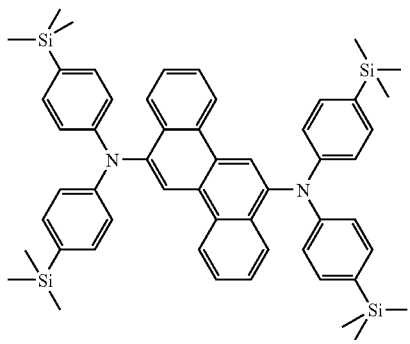
[Compound 63]
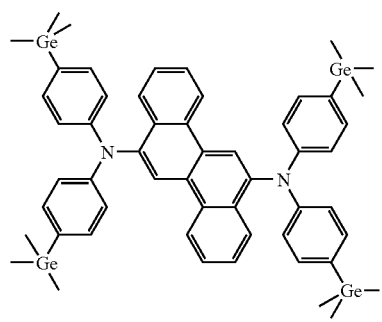
[Compound 64]
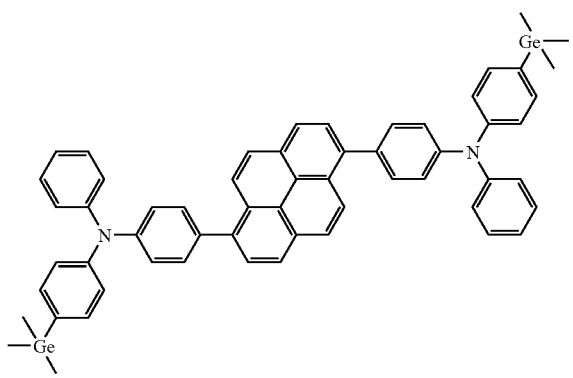
[Compound 65]
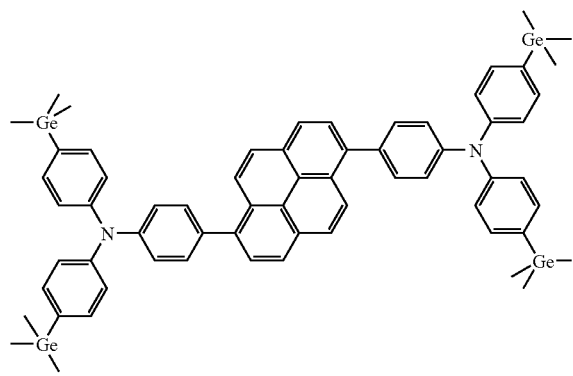
[Compound 66]
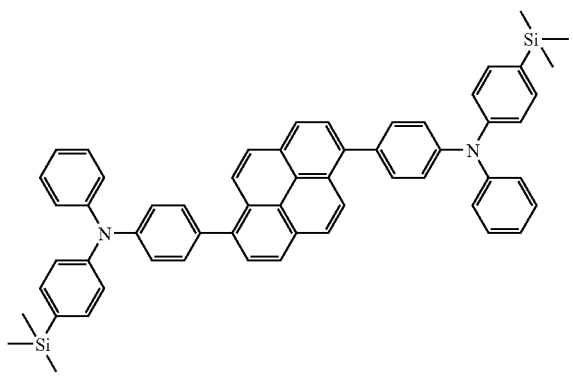
[Compound 67]
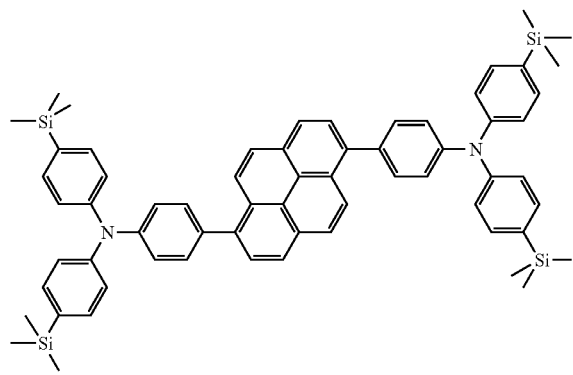
[Compound 68]
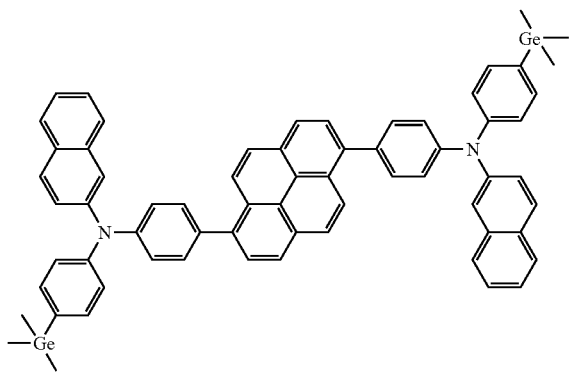

-continued
[Compound 69]
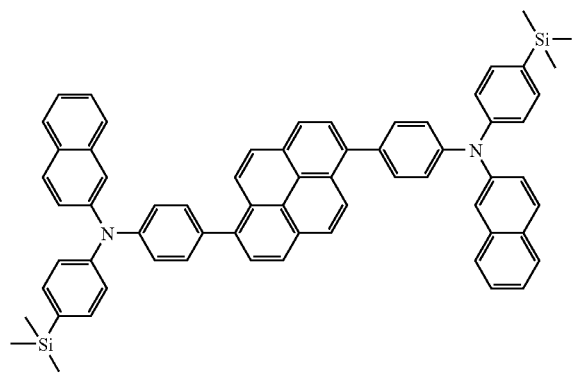
[Compound 70]
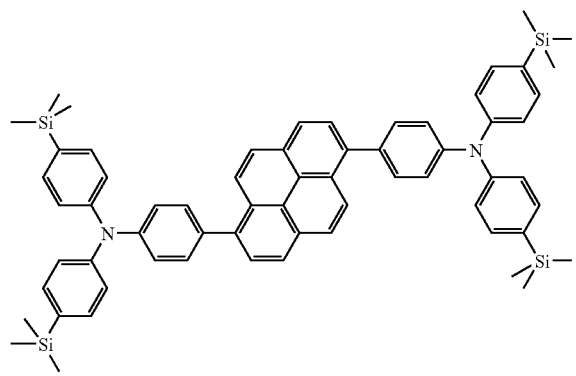
[Compound 71]
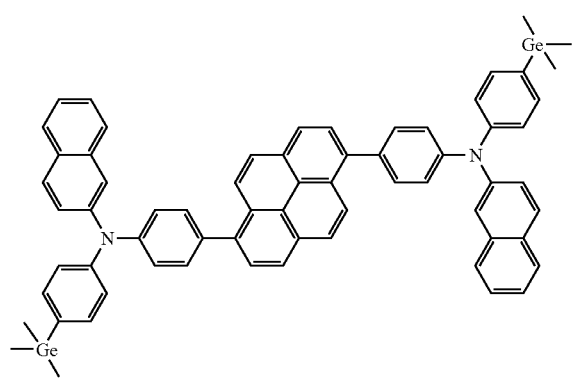
[Compound 72]
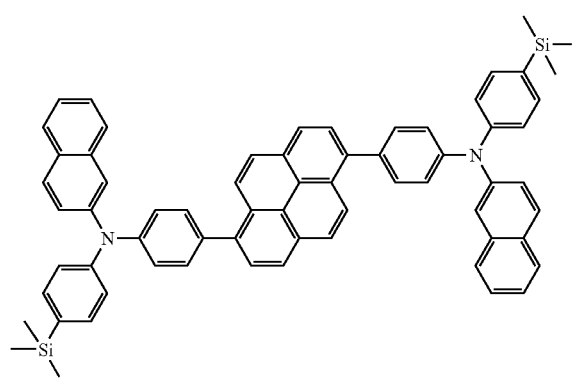
[Compound 73]
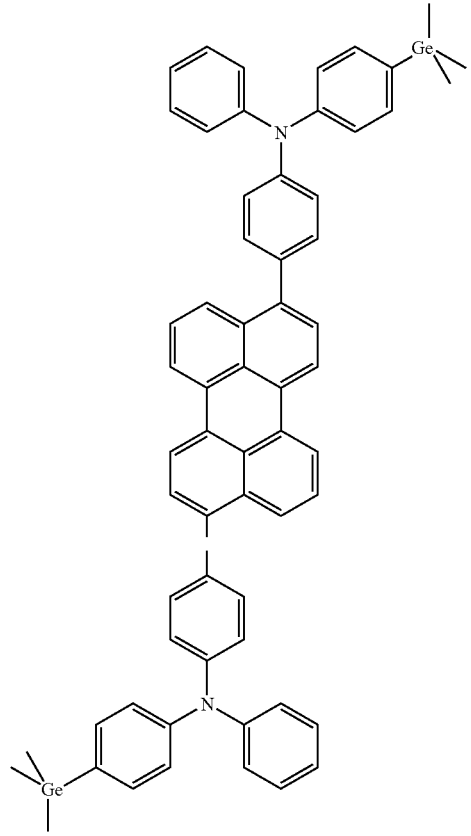
[Compound 74]
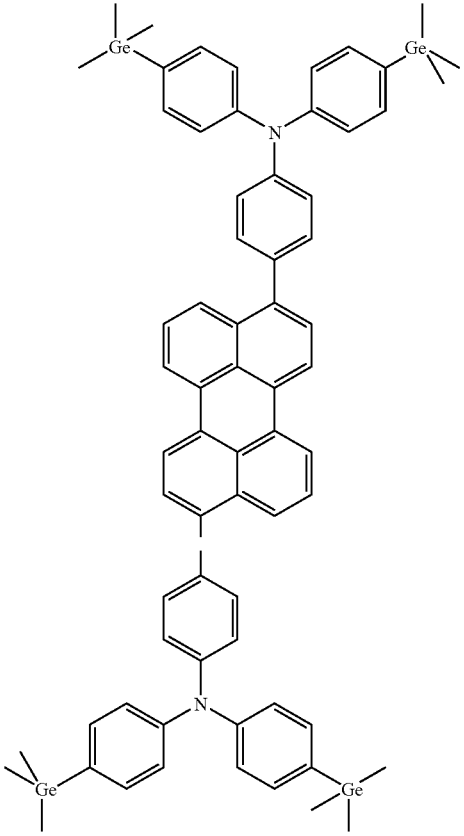

-continued
[Compound 75]
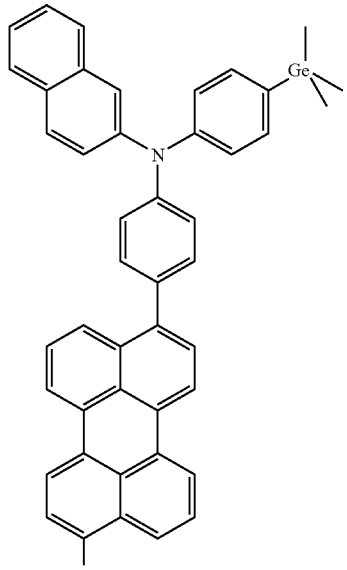
[Compound 76]
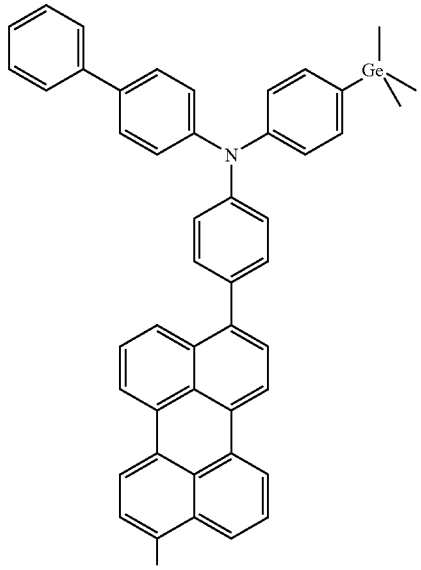
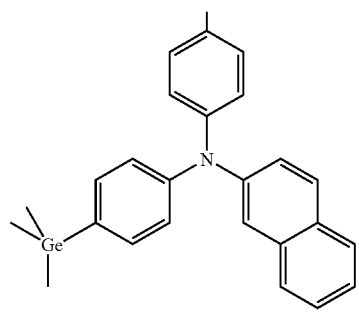
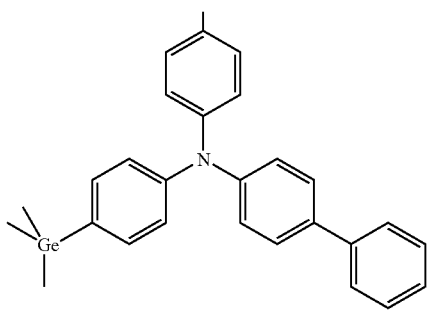
[Compound 77]
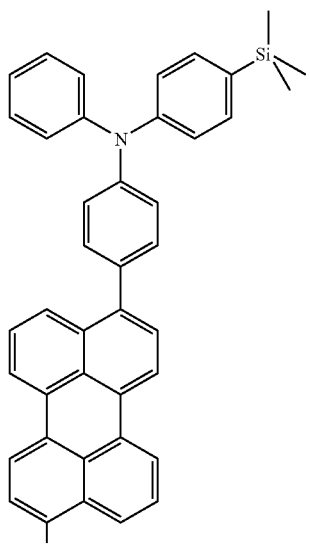
[Compound 78]
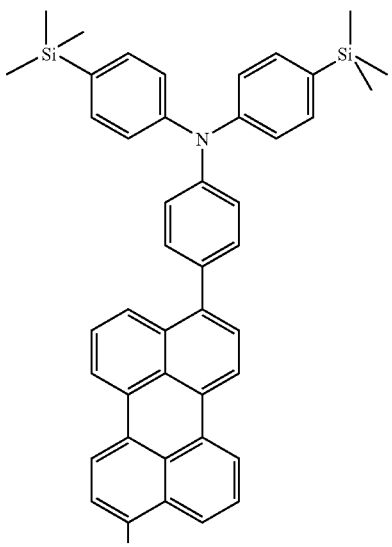

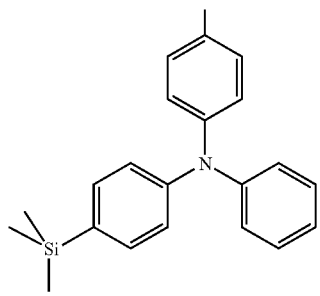
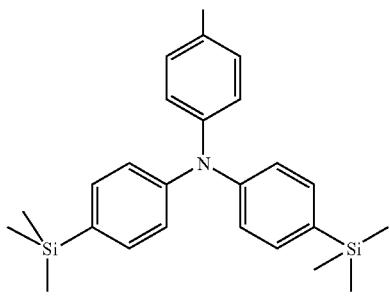
[Compound 79]
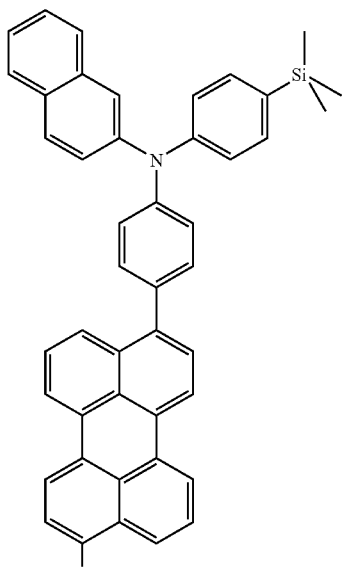
[Compound 80]
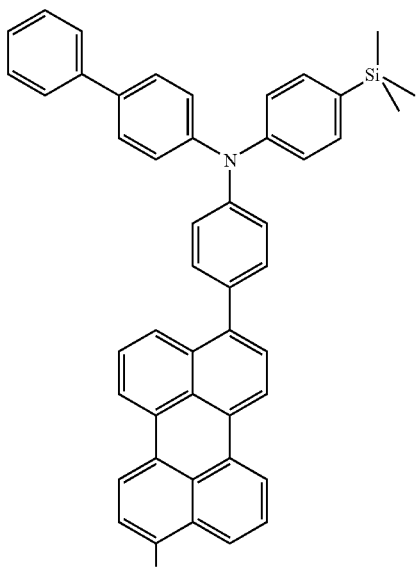
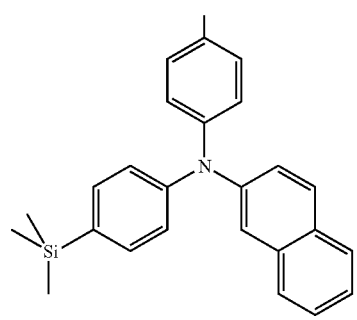
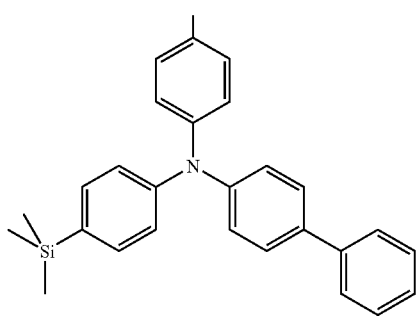
[Compound 81]
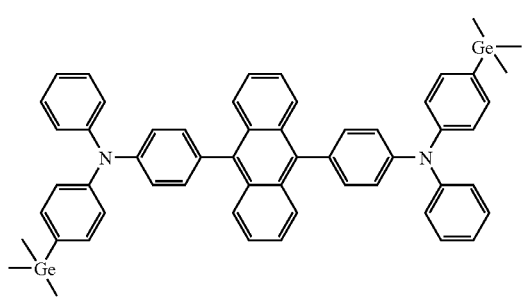
[Compound 82]
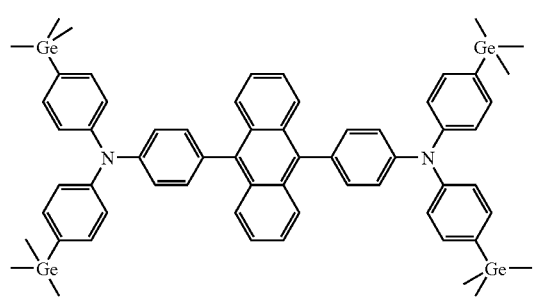

[Compound 83]
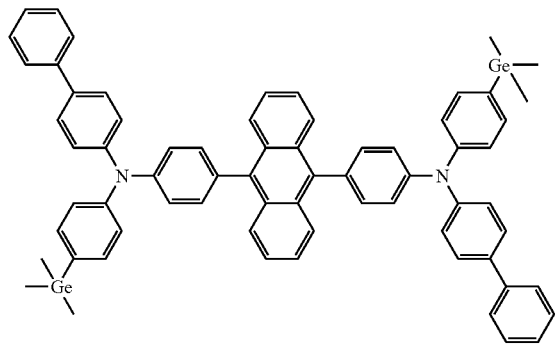
[Compound 84]
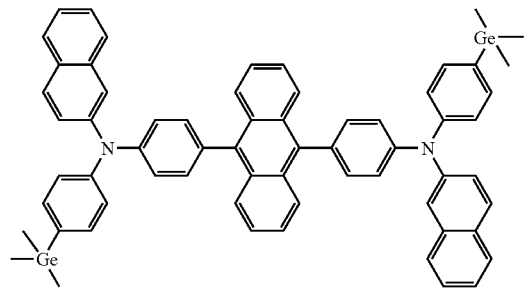
[Compound 85]
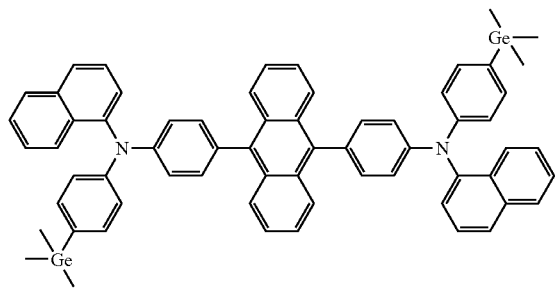
[Compound 86]
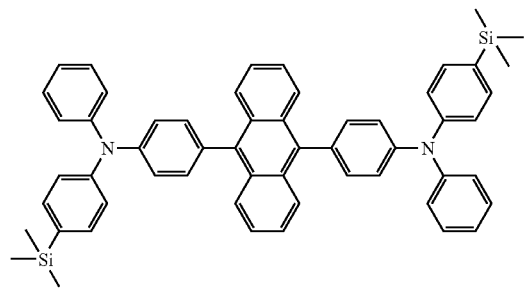
[Compound 87]
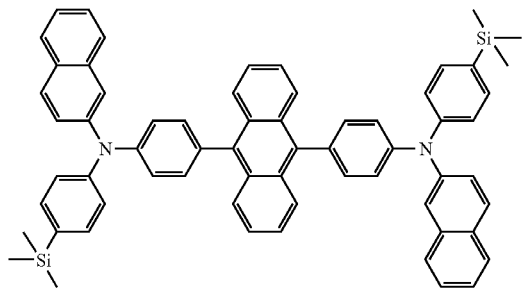
[Compound 88]
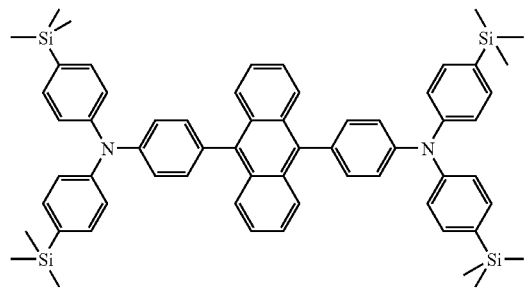
[Compound 89]
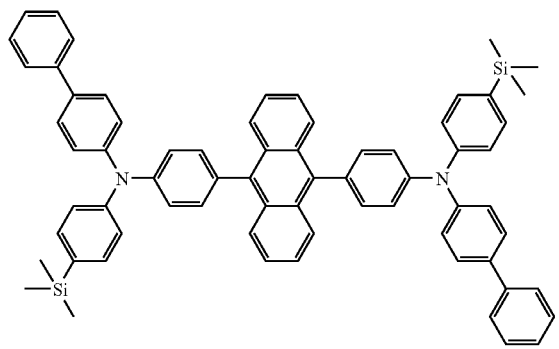
[Compound 90]
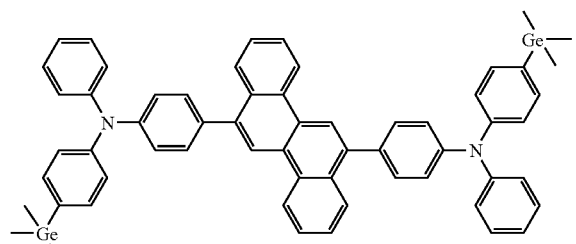

-continued
[Compound 91]
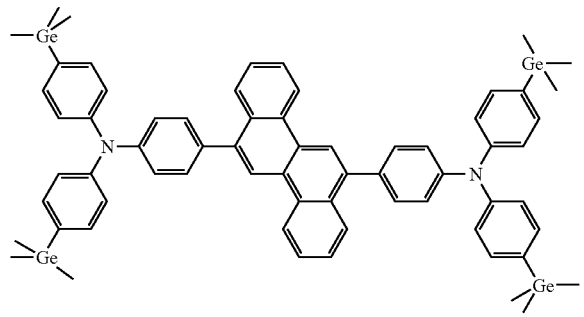
[Compound 92]
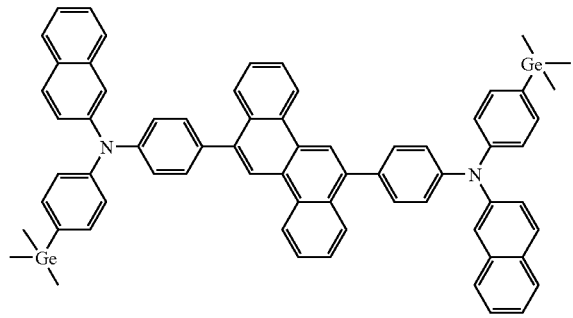
[Compound 93]
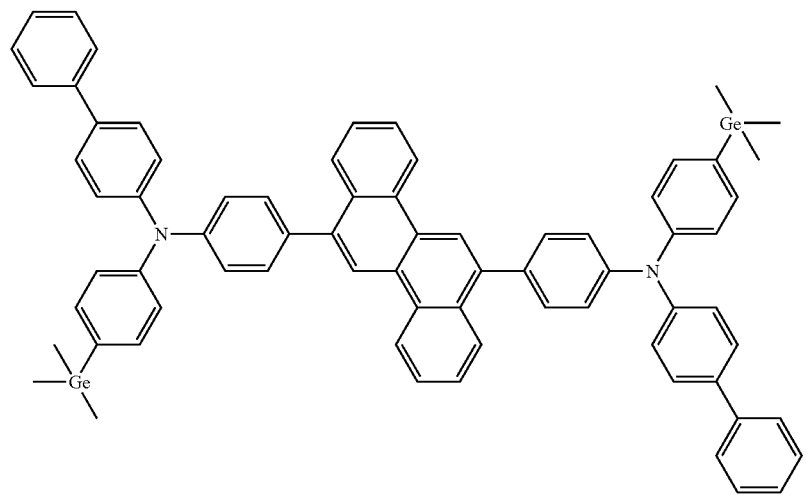
[Compound 94]
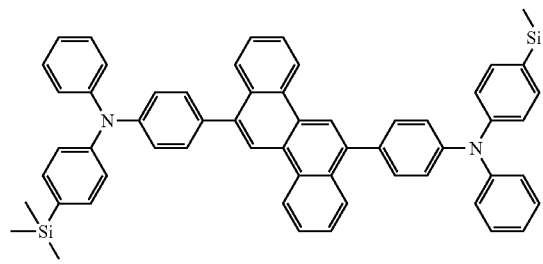
[Compound 95]
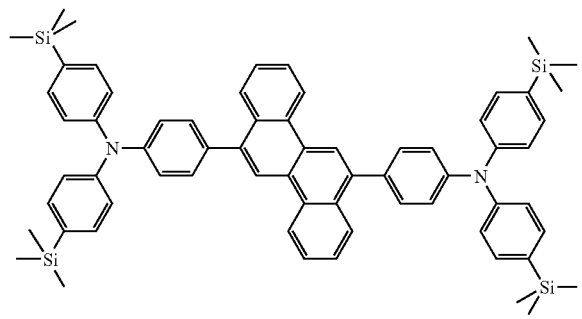
[Compound 96]
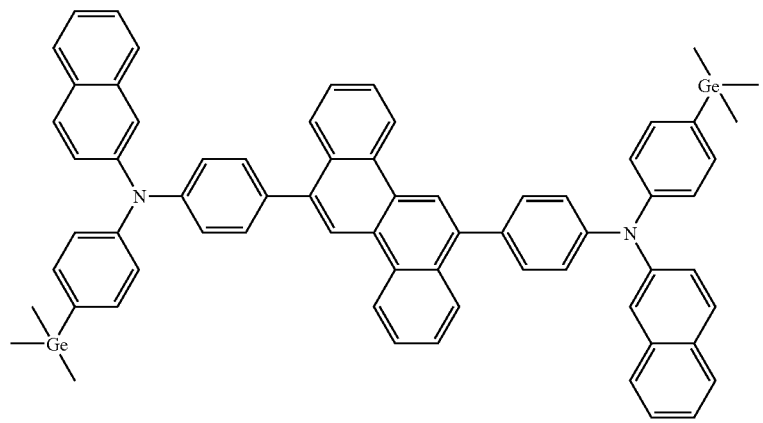

[Compound 97]
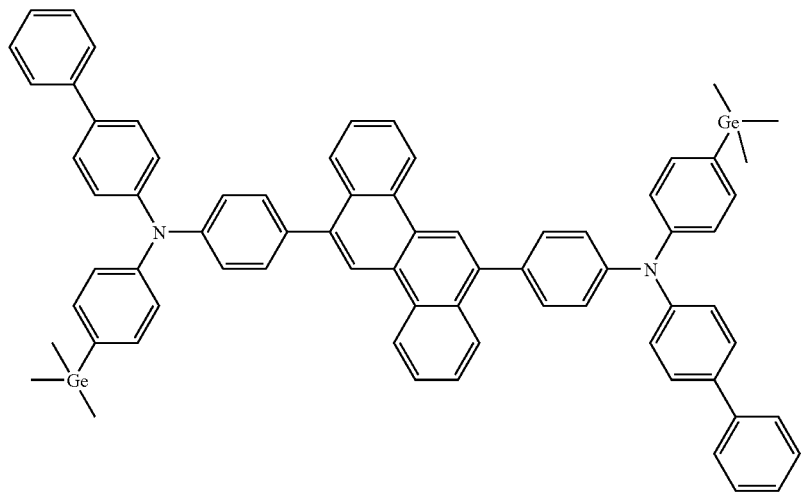
[Compound 98]
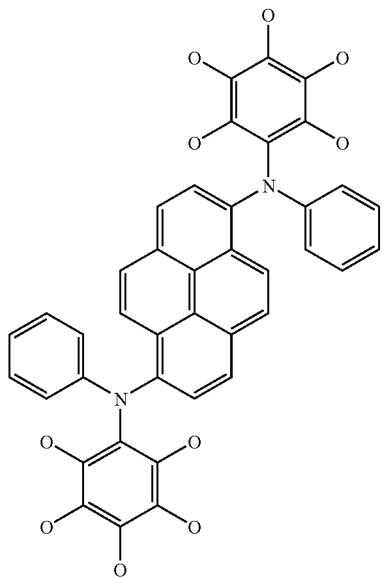
[Compound 99]
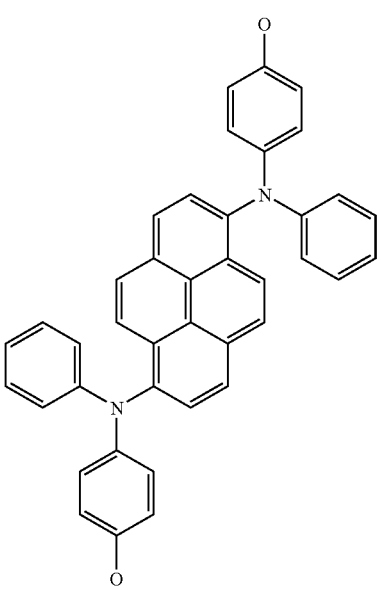
[Compound 100]
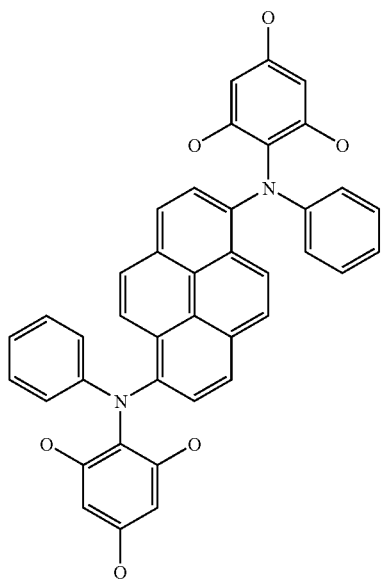
[Compound 101]
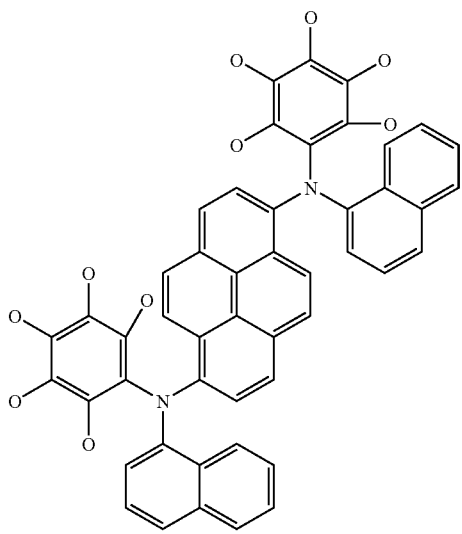

-continued
[Compound 102]
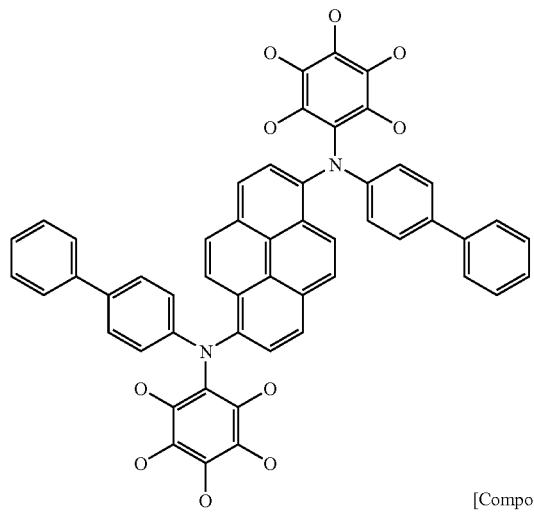
[Compound 103]
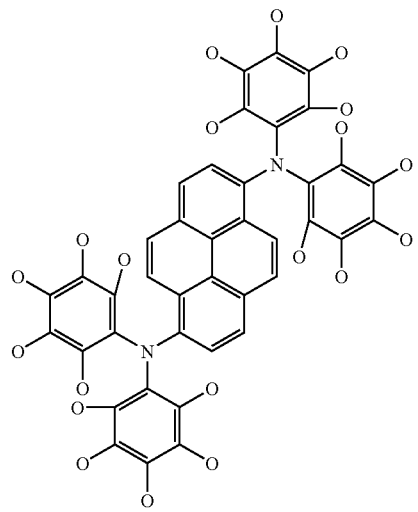
[Compound 104]
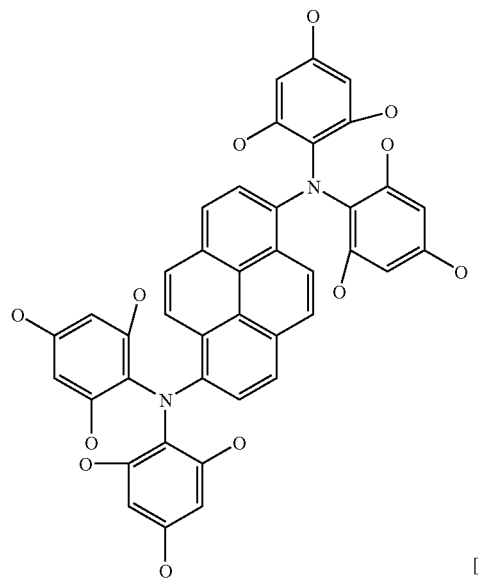
[Compound 105]
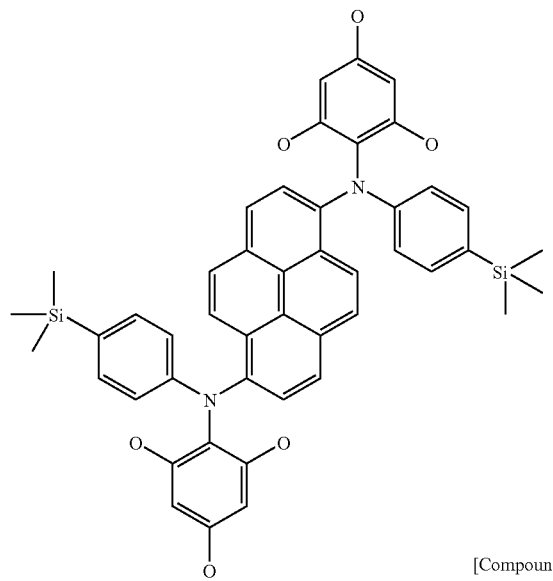
[Compound 106]
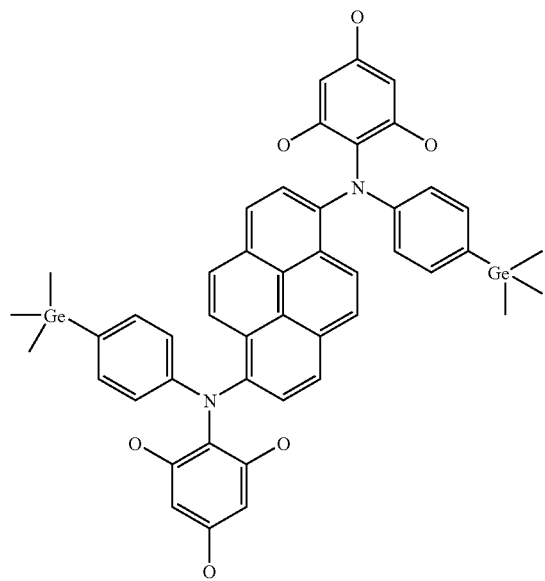
[Compound 107]
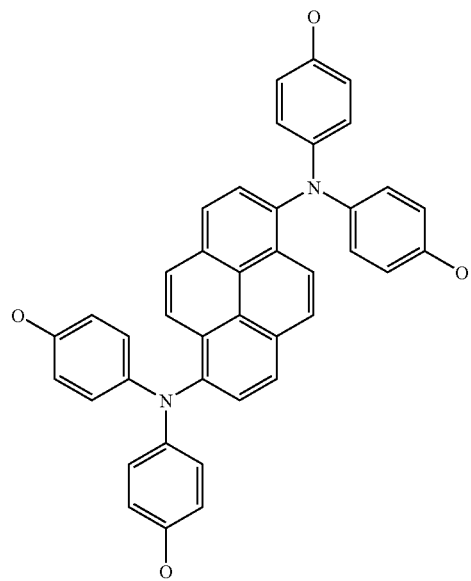

[Compound 108]
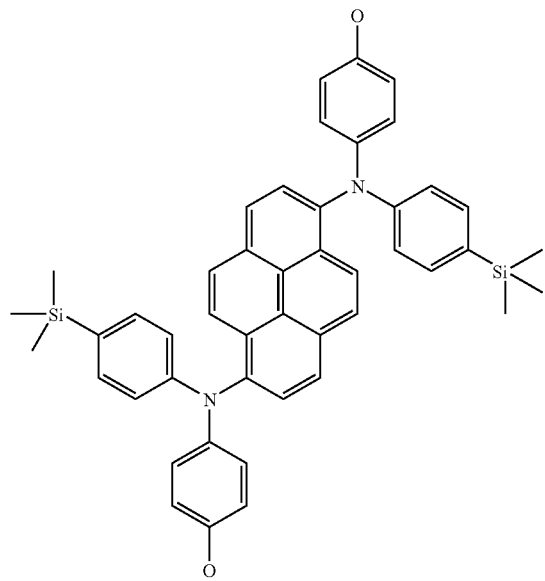
[Compound 109]
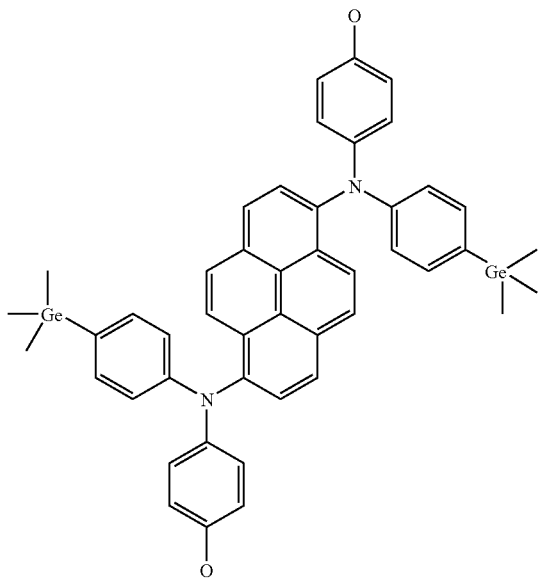
[Compound 110]
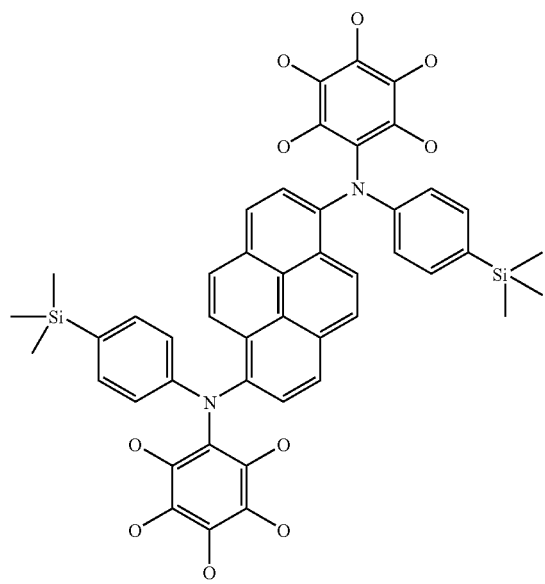
[Compound 111]
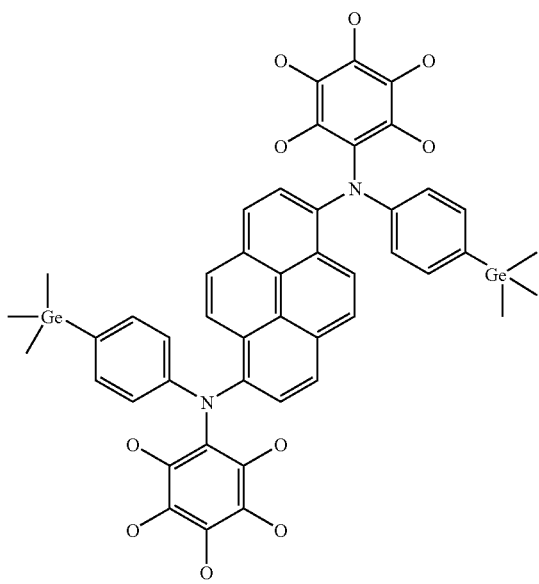
[Compound 112]
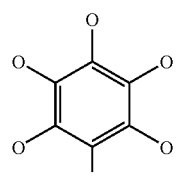
[Compound 113]
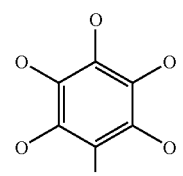

47    48
-continued
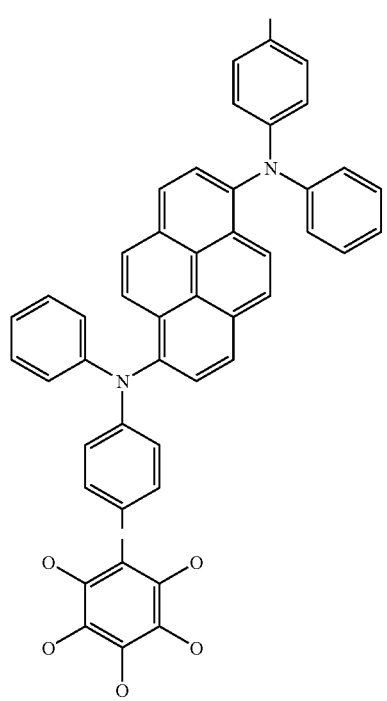 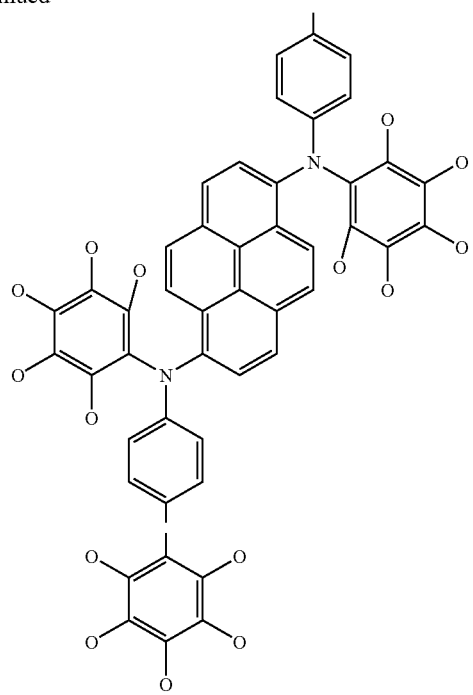
[Compound 114] 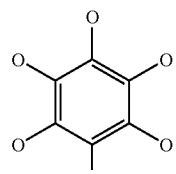　　　　[Compound 115] 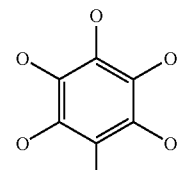
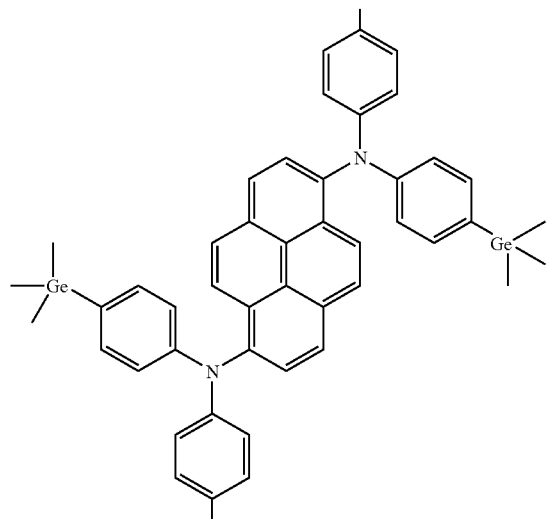 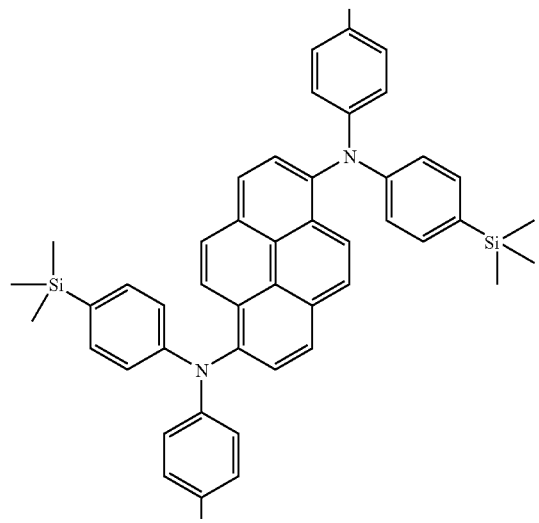
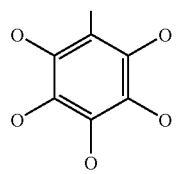 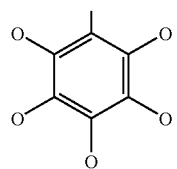

-continued
[Compound 116]
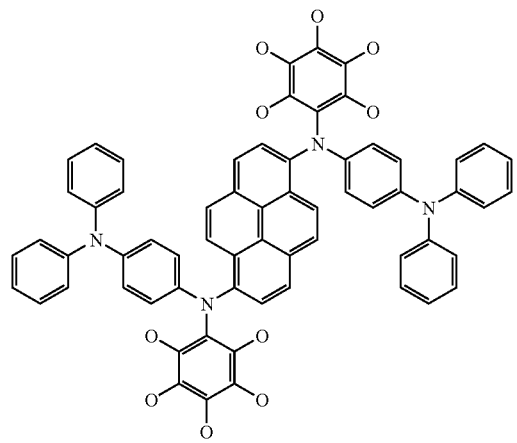
[Compound 117]
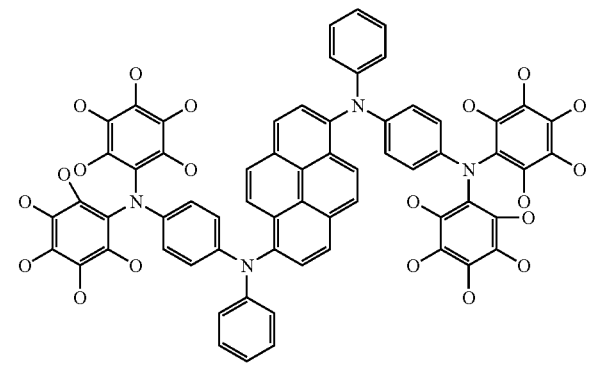
[Compound 118]
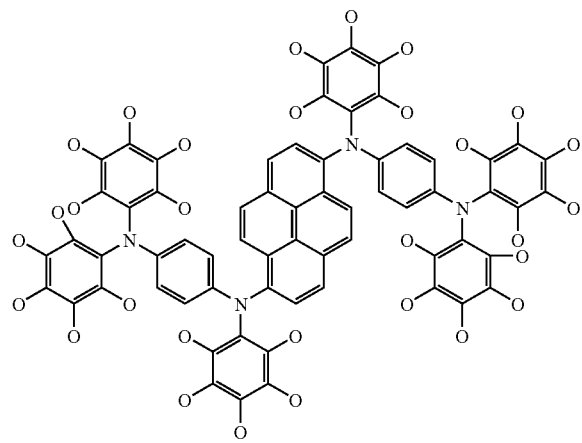
[Compound 119]
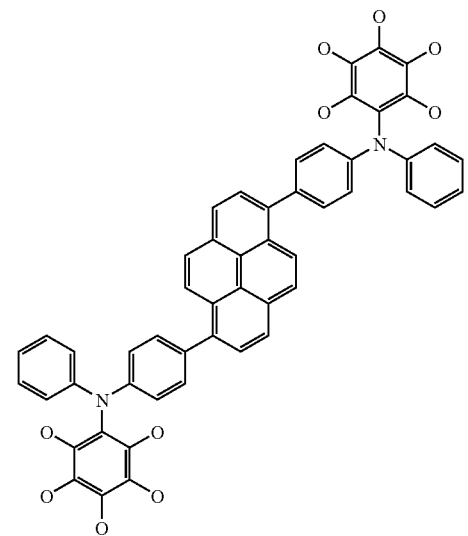
[Compound 120]
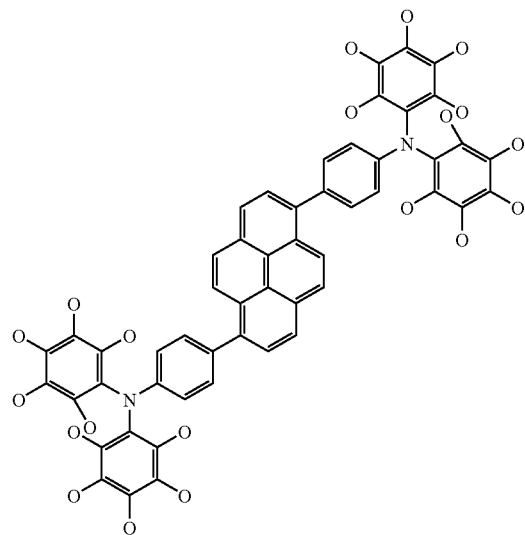
[Compound 121]
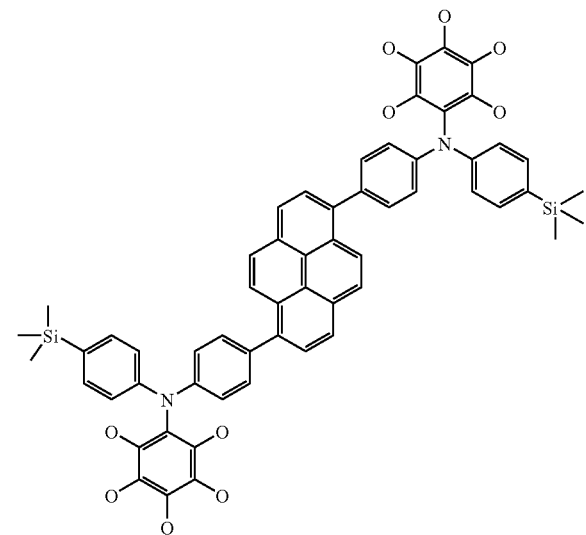

[Compound 122]
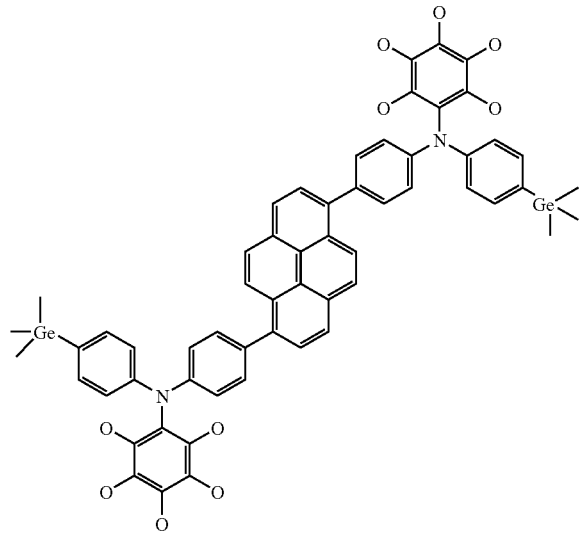
[Compound 123]
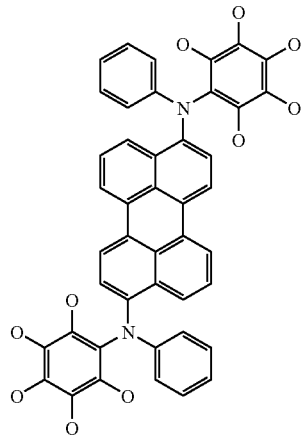
[Compound 124]
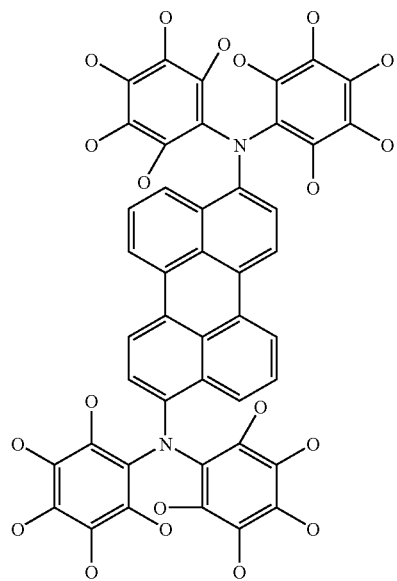
[Compound 125]
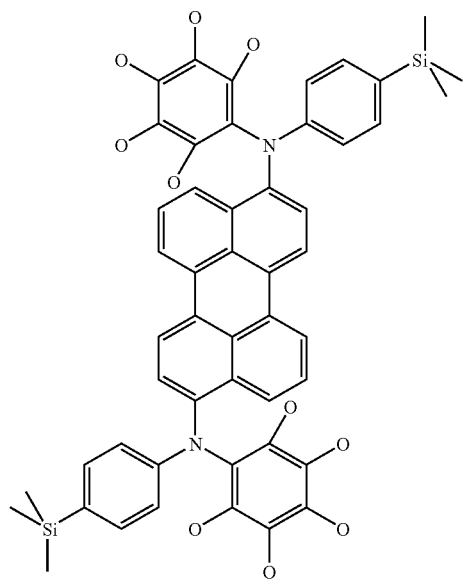

-continued
[Compound 126]
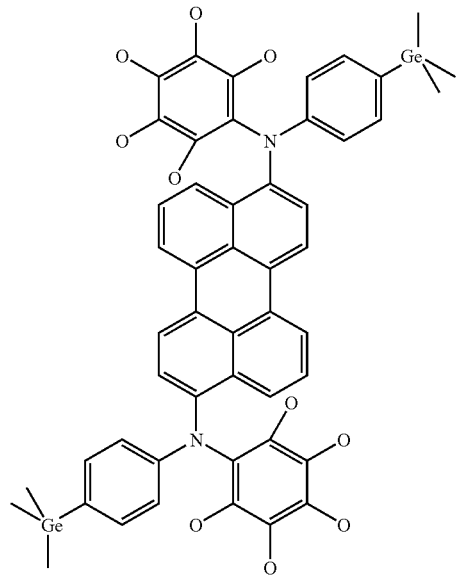
[Compound 127]
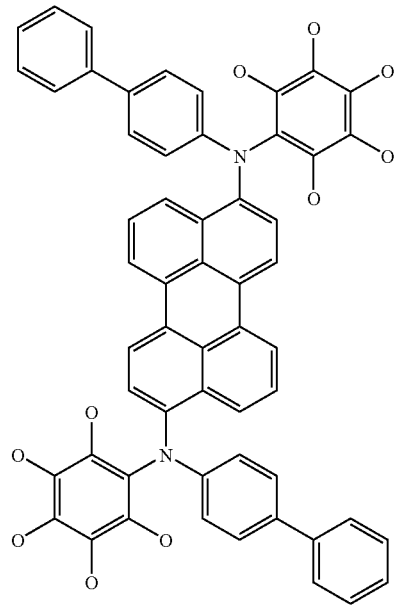
[Compound 128]
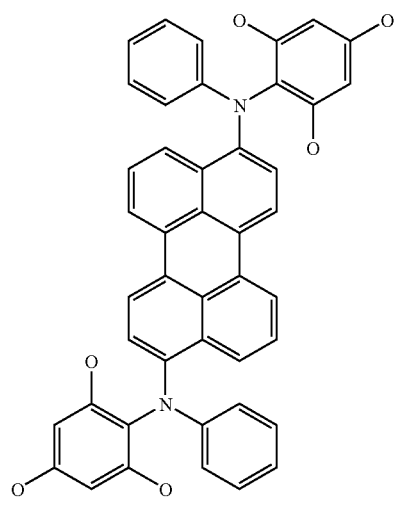
[Compound 129]
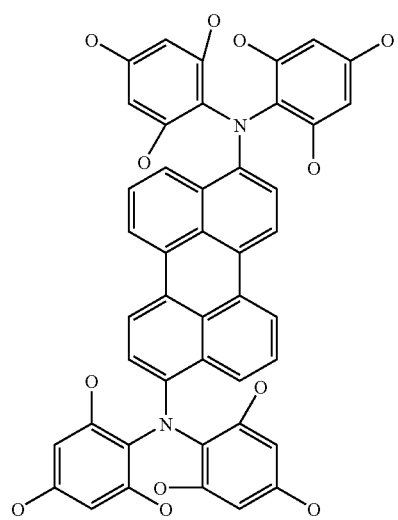

-continued
[Compound 130]
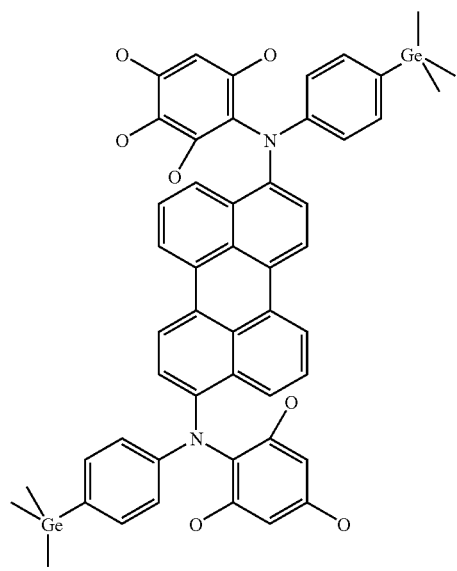
[Compound 131]
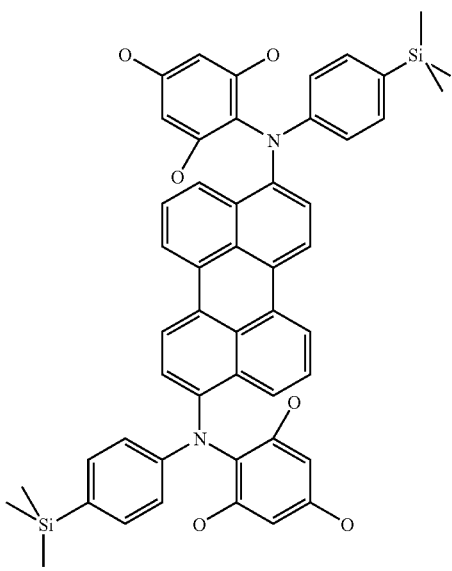
[Compound 132]
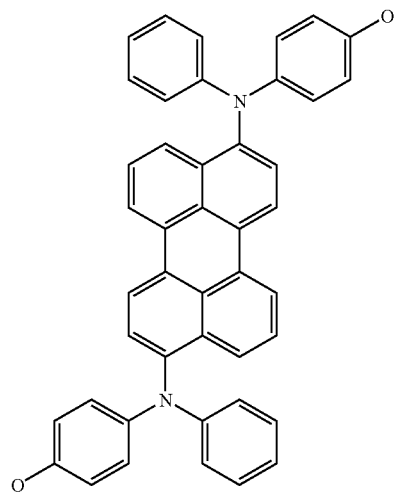
[Compound 133]
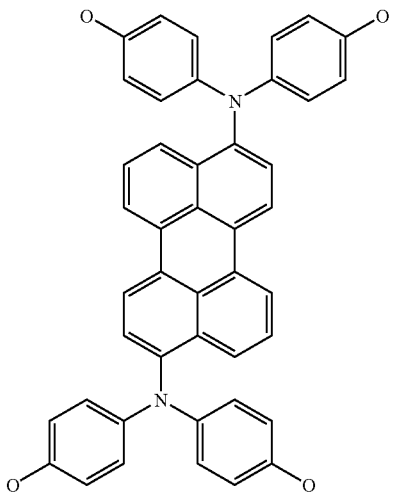
[Compound 134]
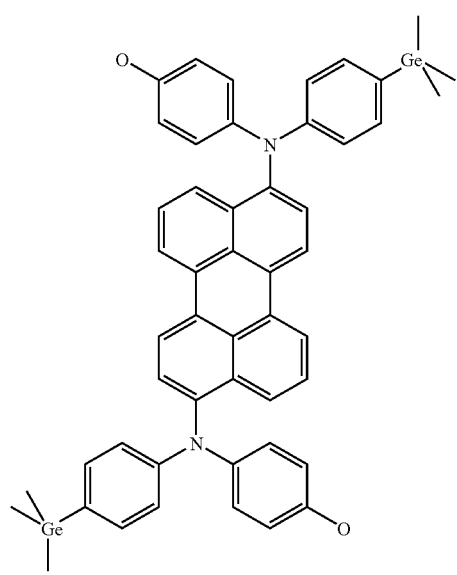
[Compound 135]
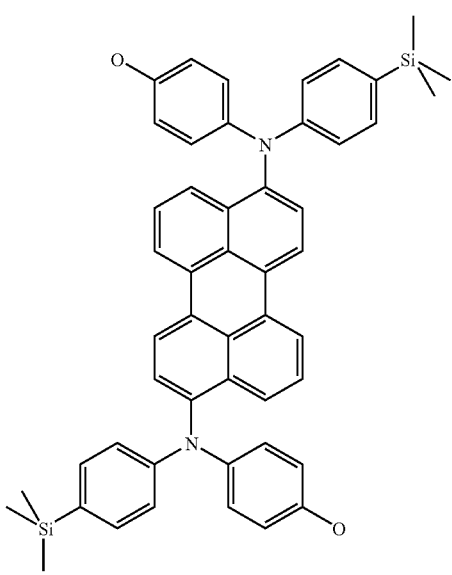

[Compound 136]
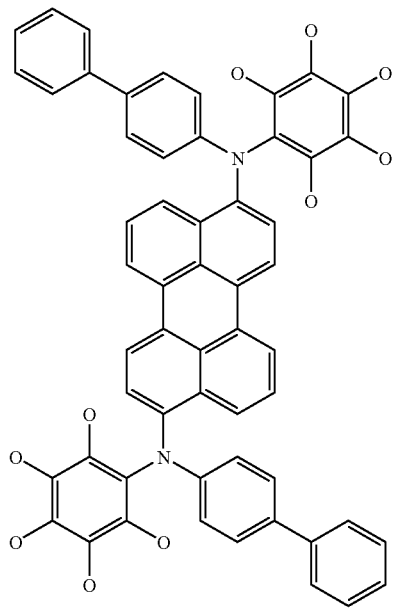
[Compound 137]
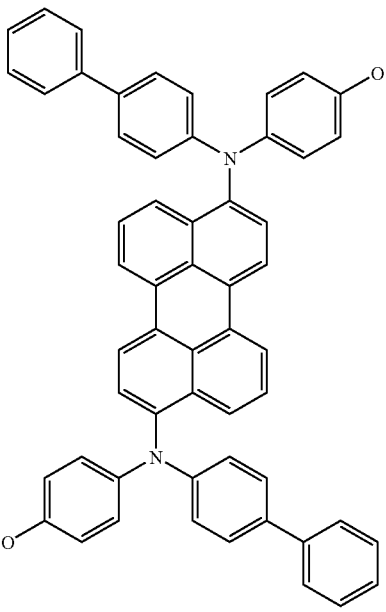
[Compound 138]
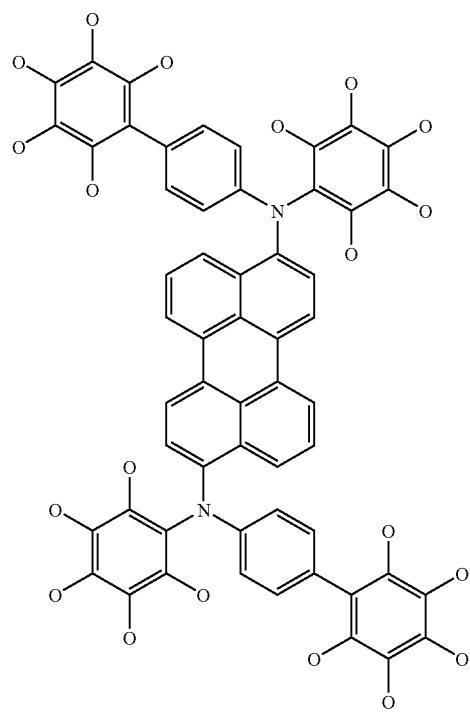
[Compound 139]
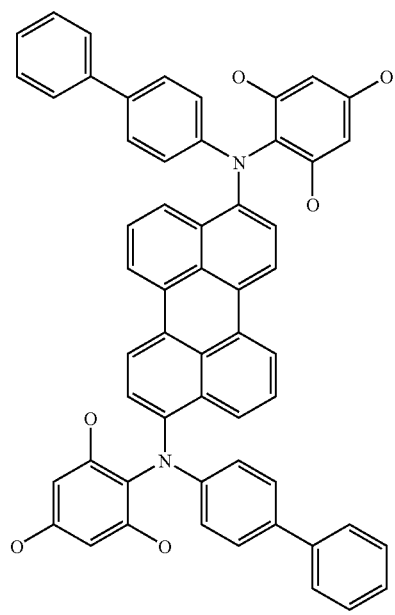
[Compound 140]
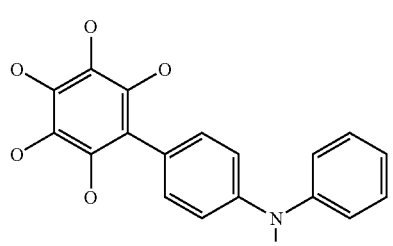
[Compound 141]
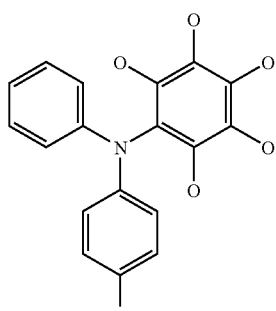

59
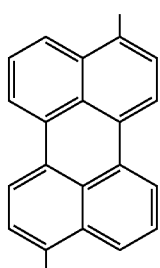
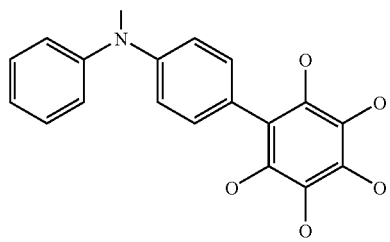
60
-continued
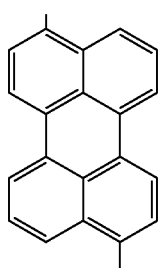
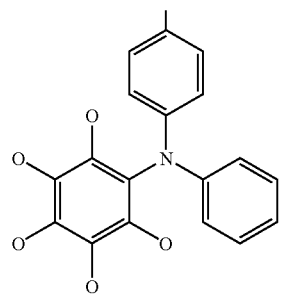
[Compound 142]
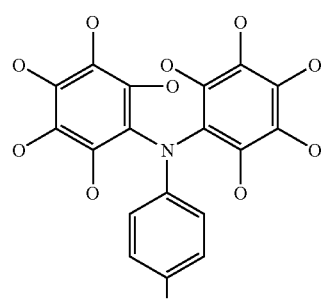
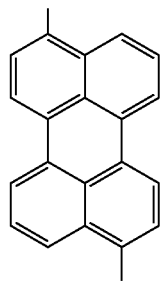
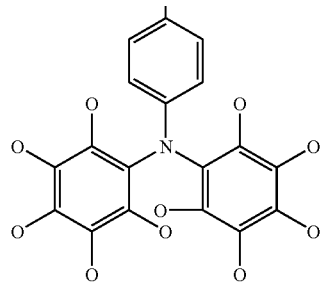
[Compound 143]
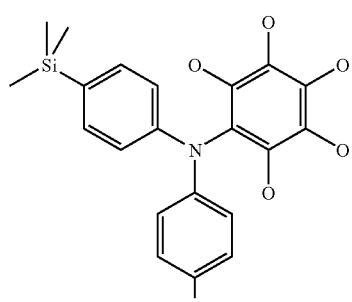
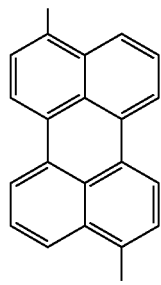
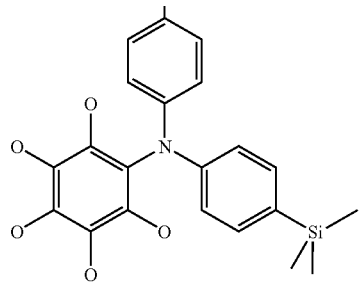

-continued
[Compound 144]
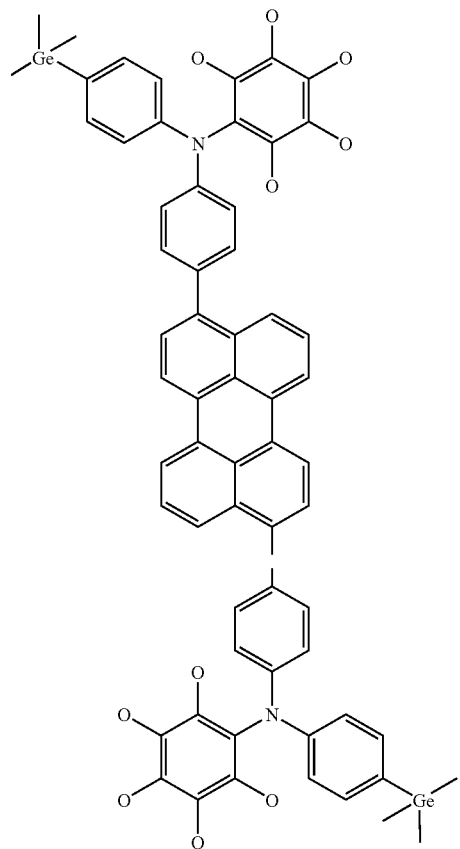
[Compound 145]
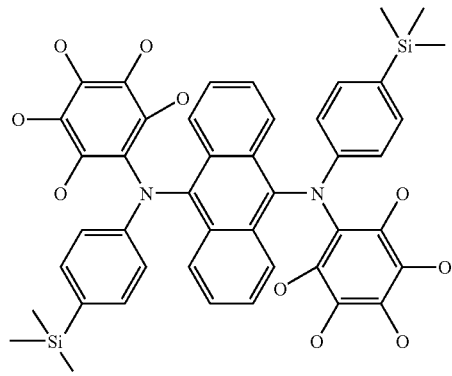
[Compound 146]
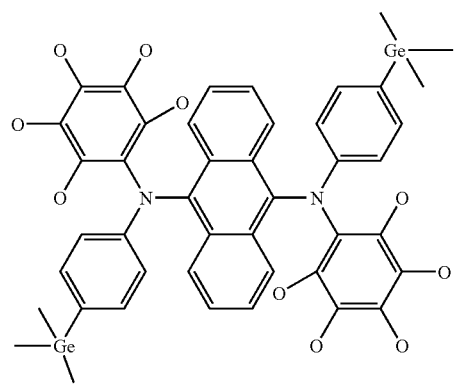
[Compound 147]
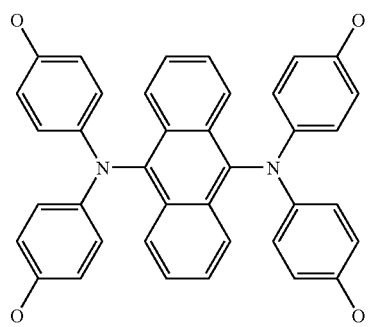
[Compound 148]
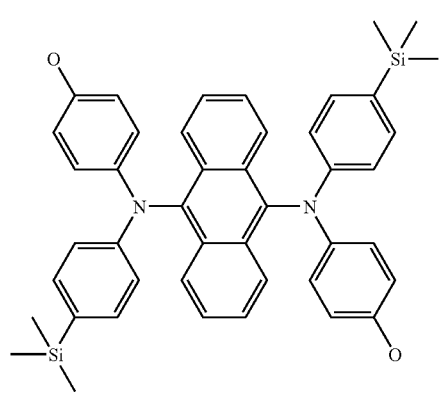
[Compound 149]
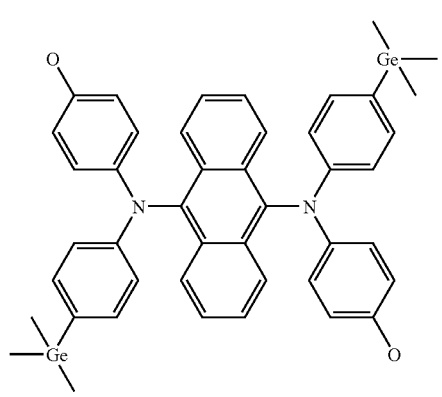

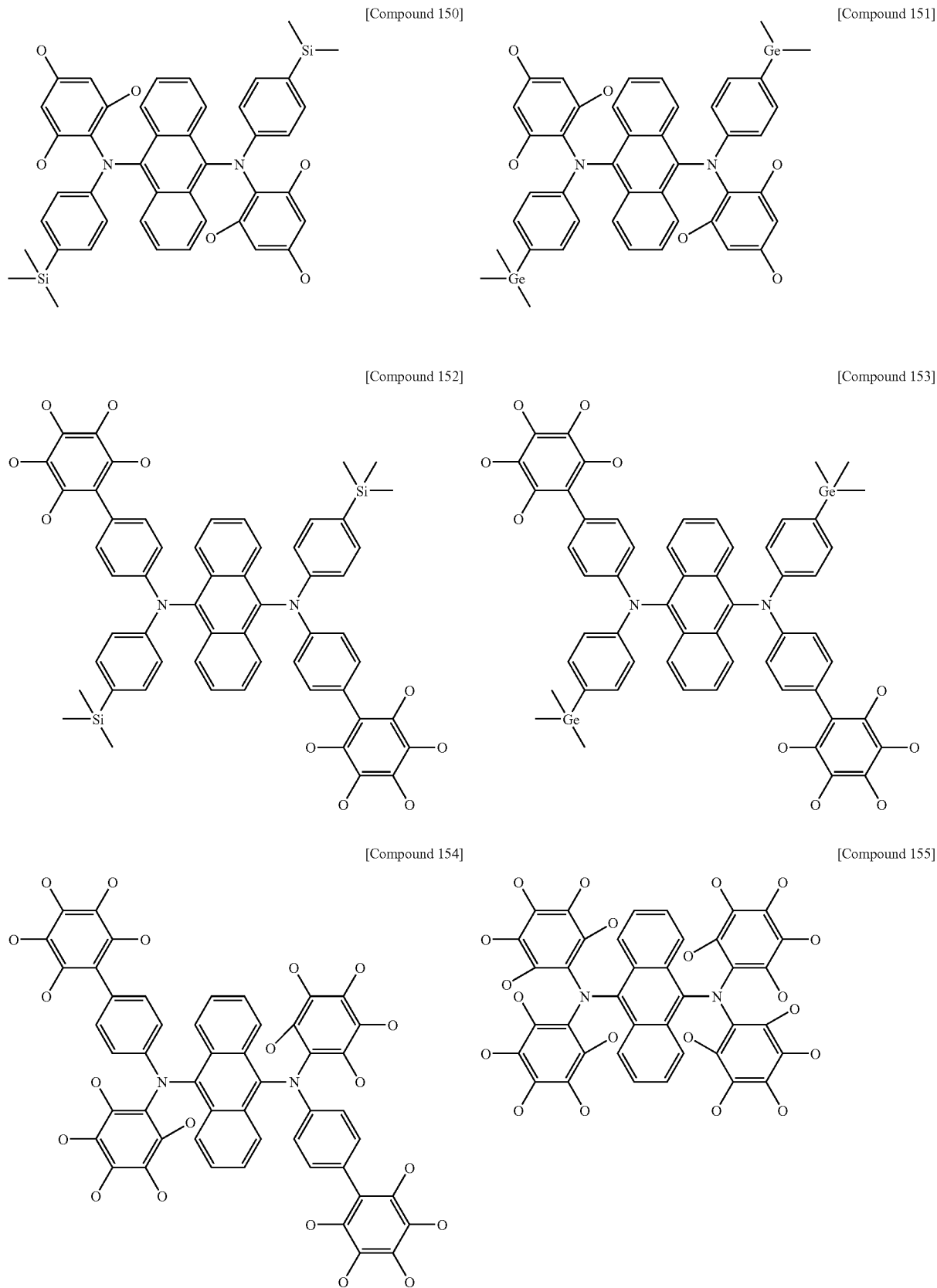

-continued
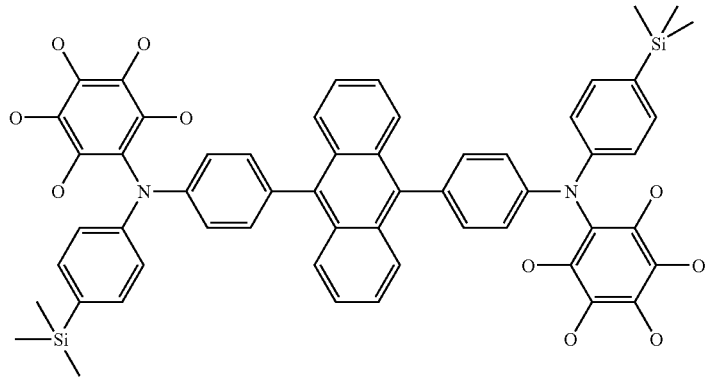
[Compound 156]
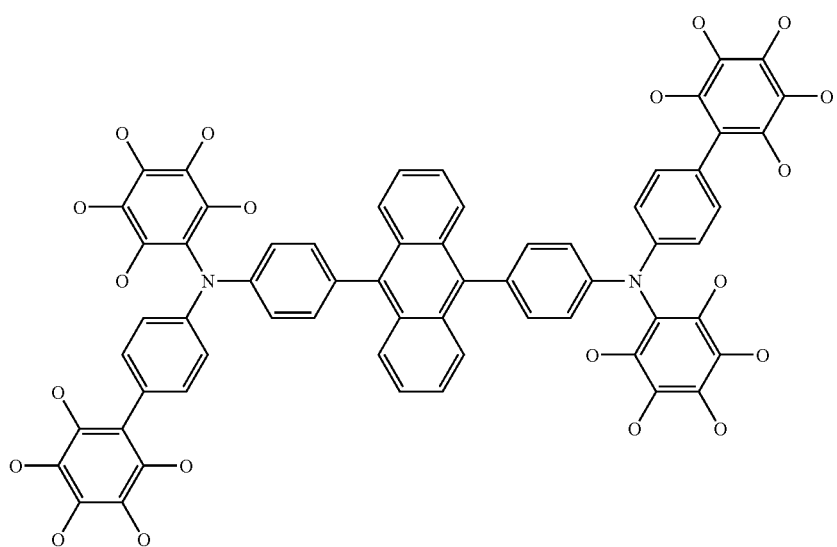
[Compound 157]
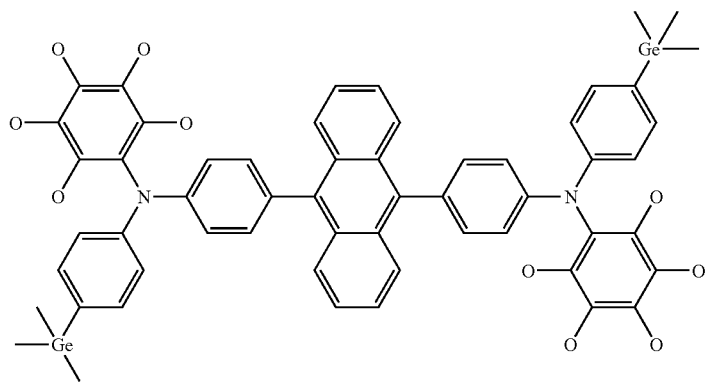
[Compound 158]

[Compound 159]
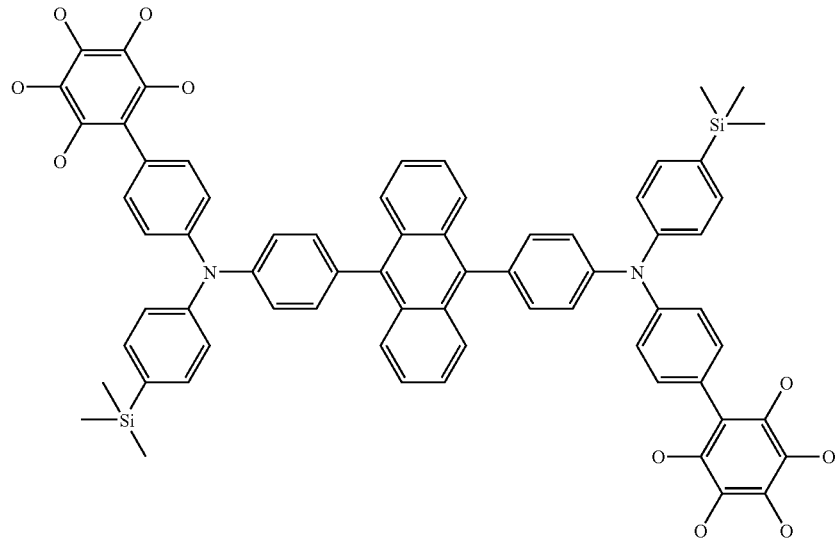
[Compound 160]
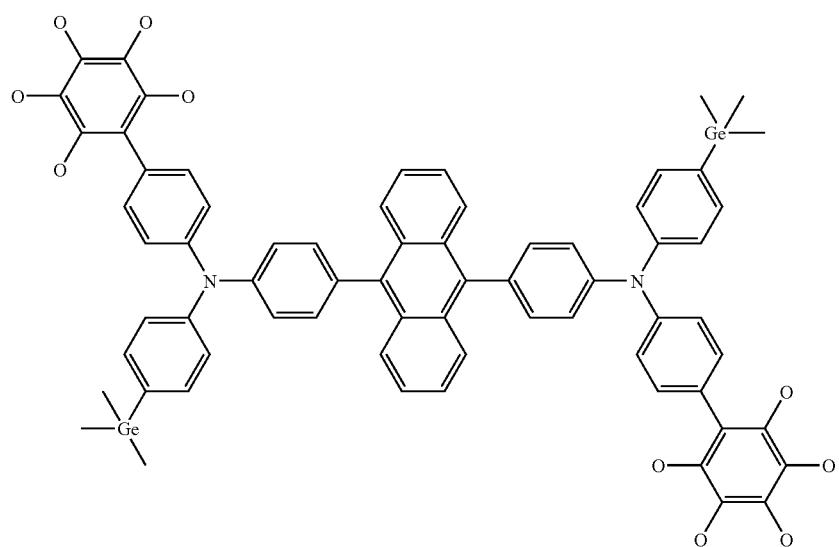
[Compound 161]
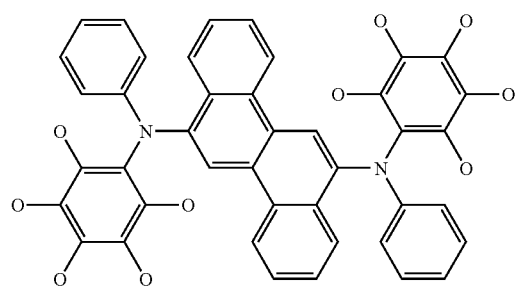
[Compound 162]
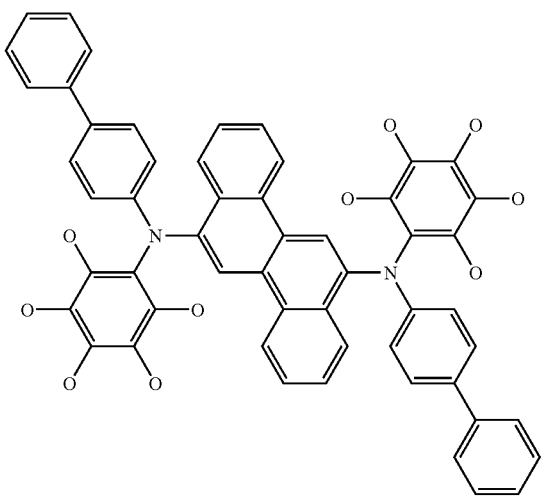

[Compound 163] 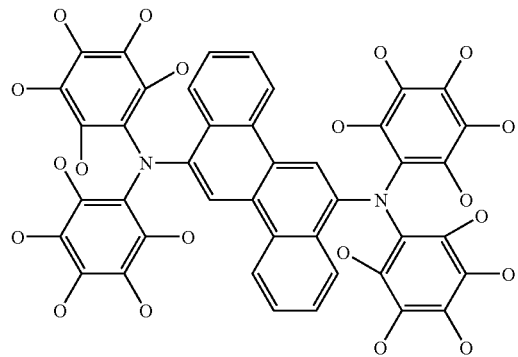
[Compound 164] 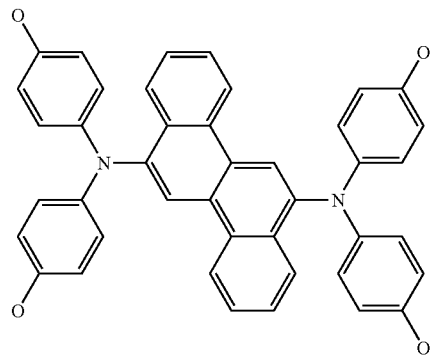
[Compound 165] 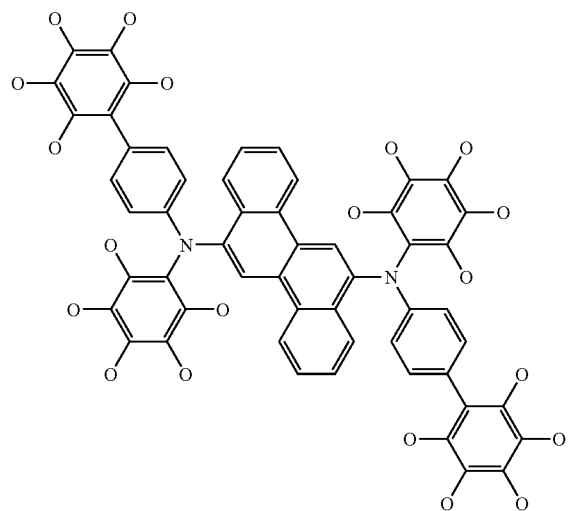
[Compound 166] 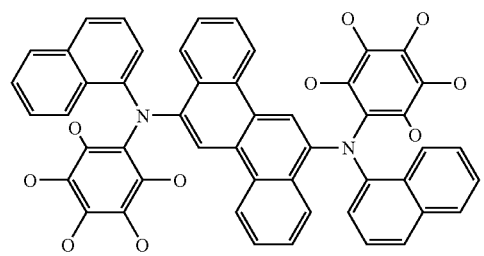
[Compound 167] 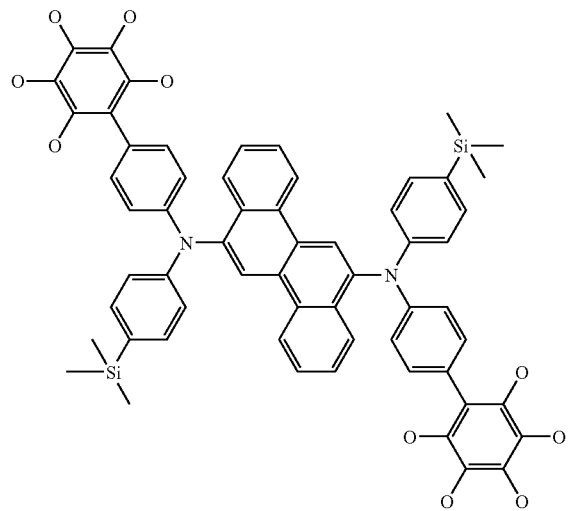
[Compound 168] 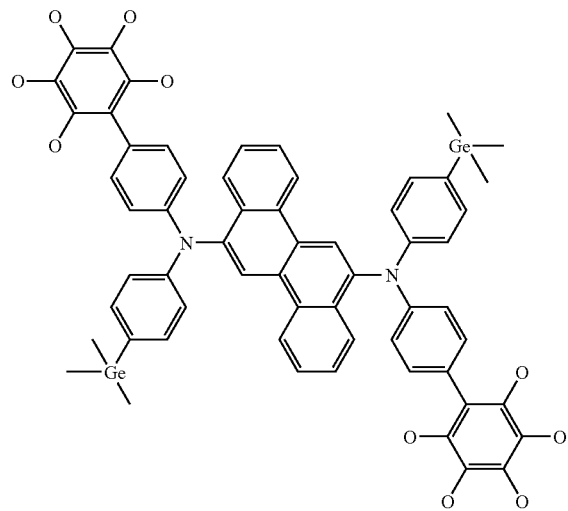

-continued
[Compound 169]
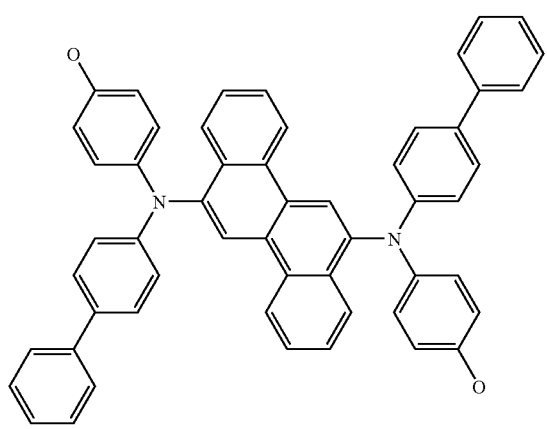
[Compound 170]
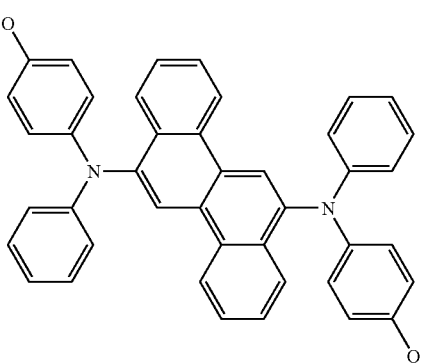
[Compound 171]
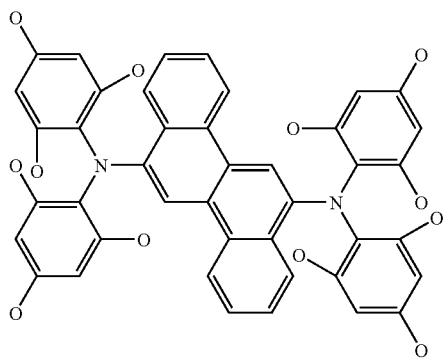
[Compound 172]
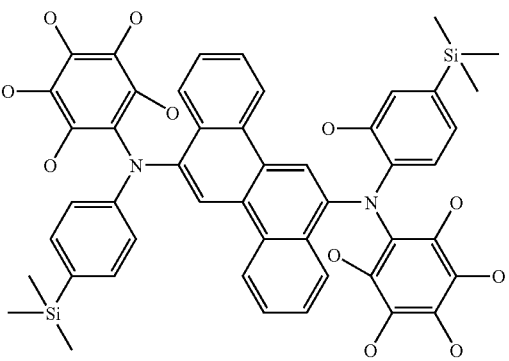
[Compound 173]
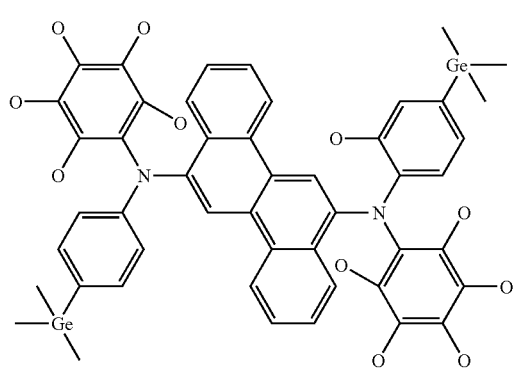
[Compound 174]
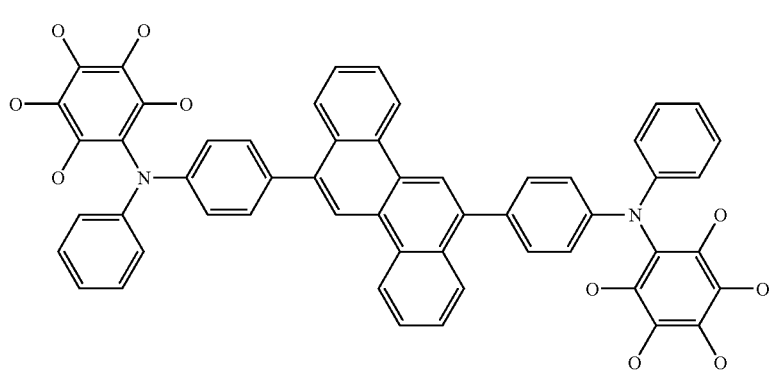

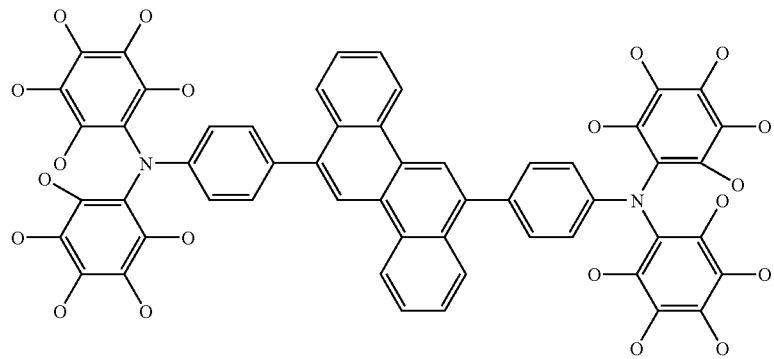
[Compound 175]
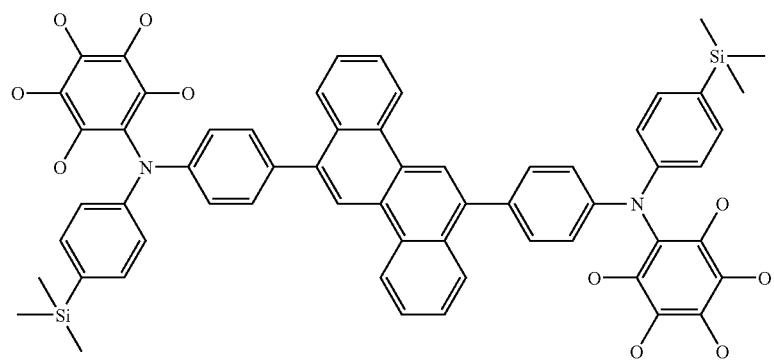
[Compound 176]
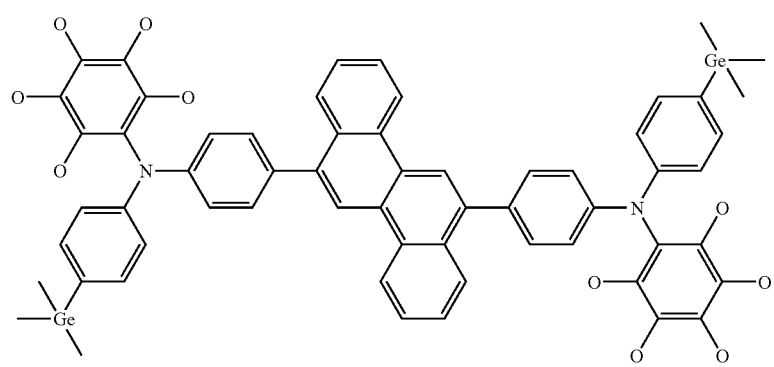
[Compound 177]
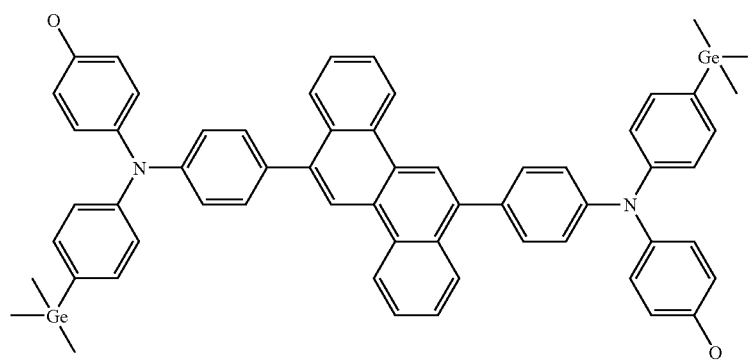
[Compound 178]

[Compound 179]
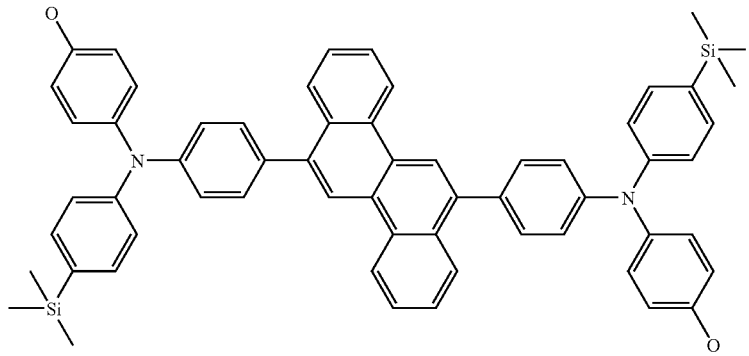
[Compound 180]
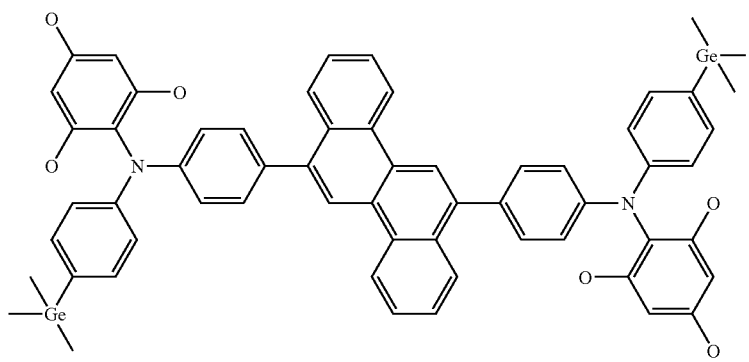
[Compound 181]
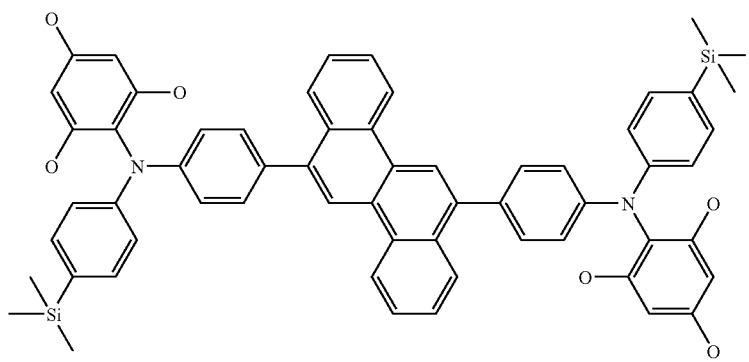
[Compound 182]
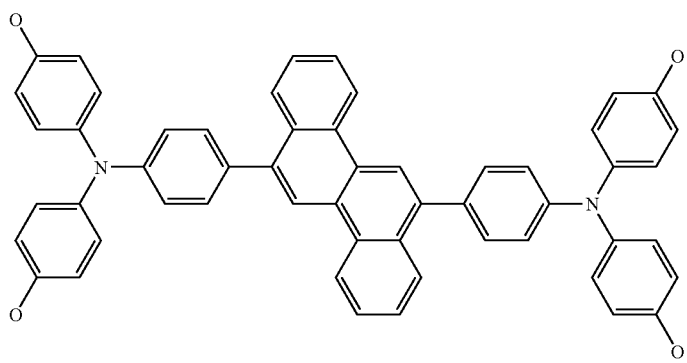

[Compound 183]
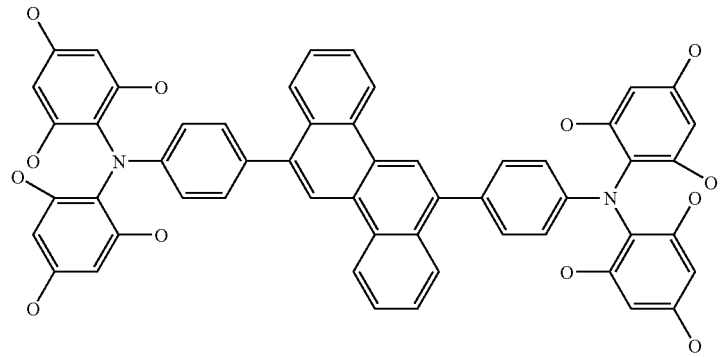
[Compound184]
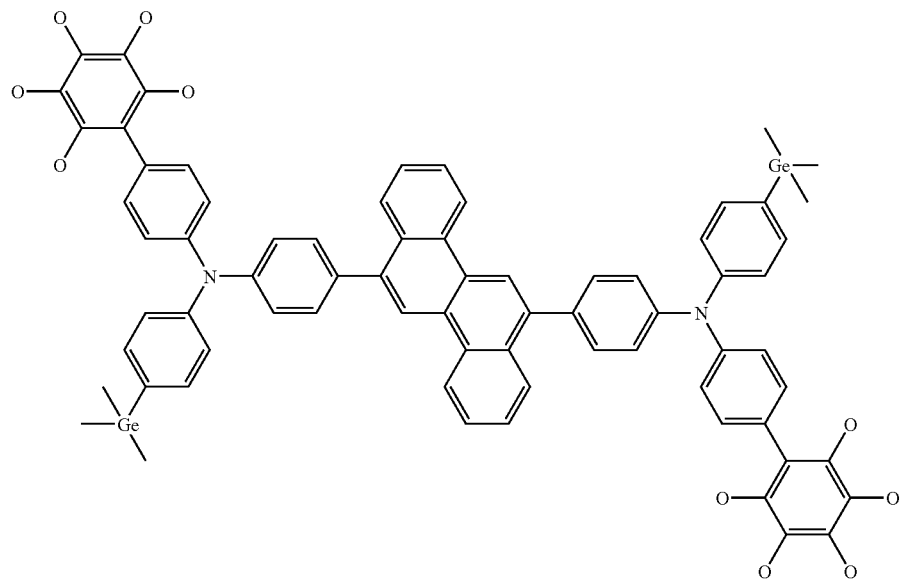
[Compound185]
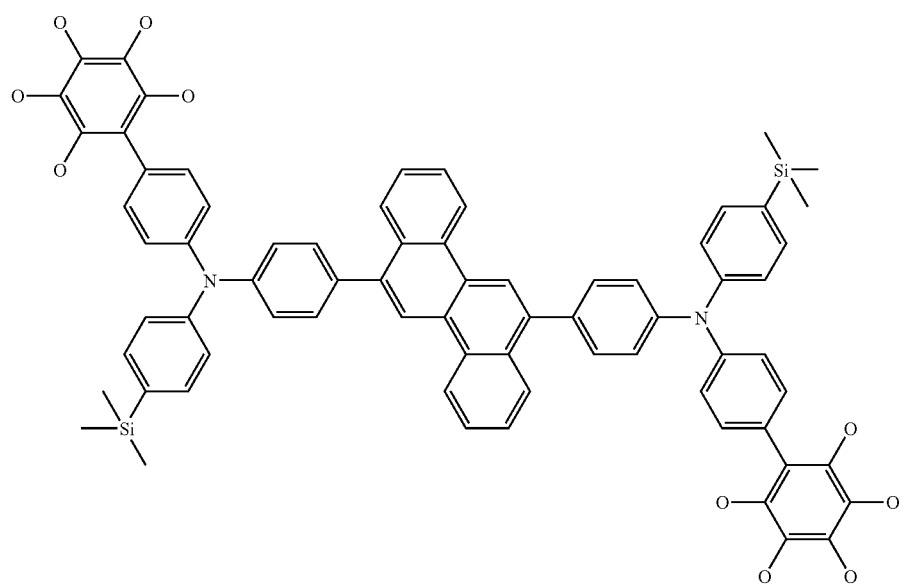

[Compound 186]
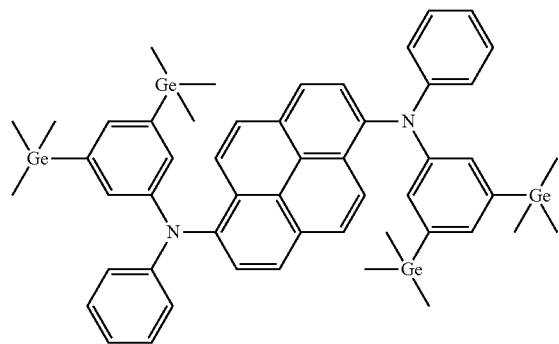
[Compound 187]
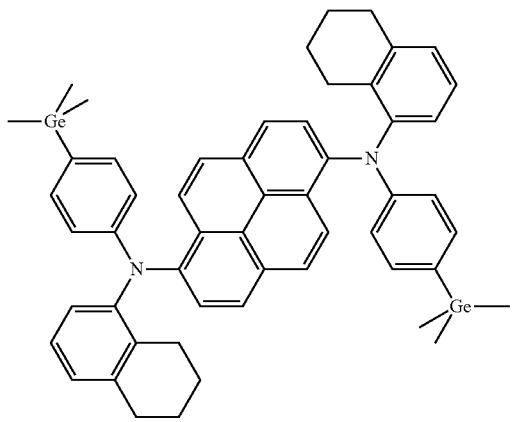
[Compound 188]
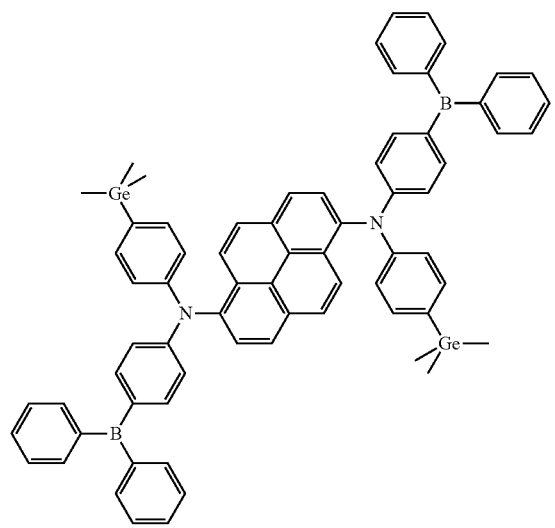
[Compound 189]
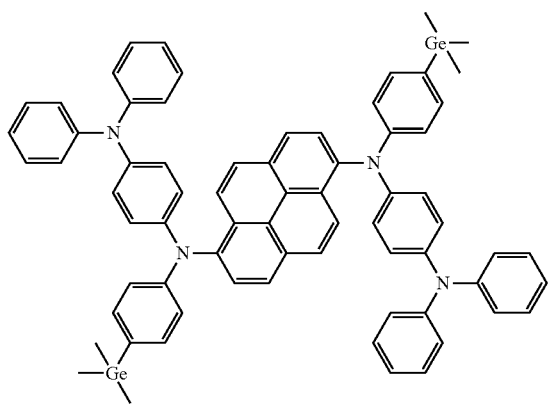
[Compound 190]
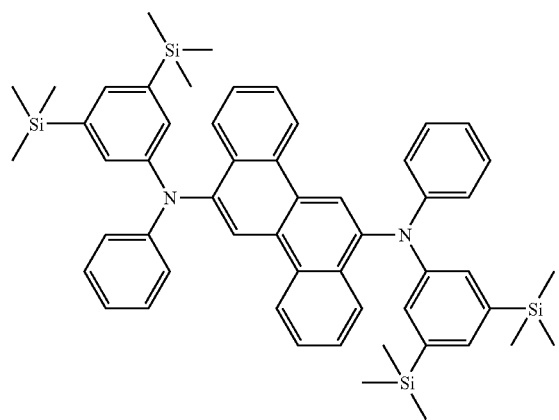
[Compound 191]
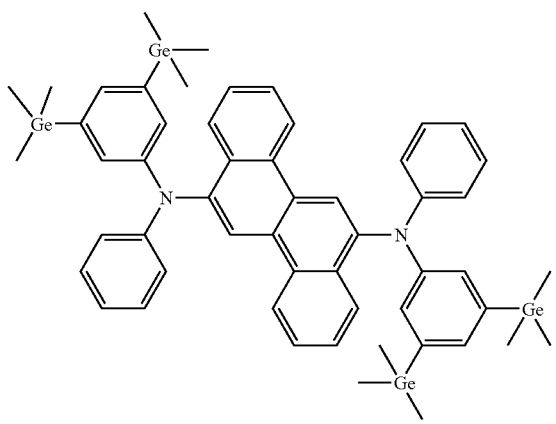

-continued
[Compound 192]
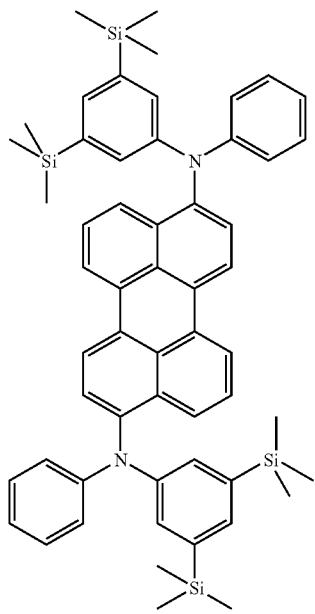
[Compound 193]
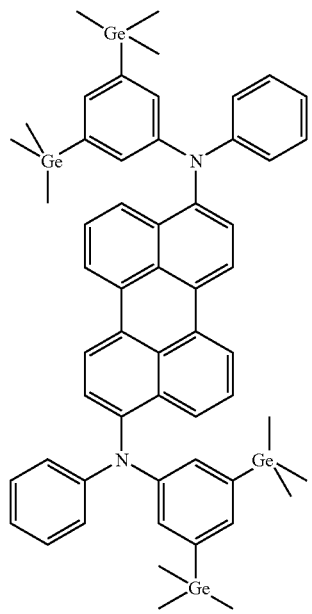
[Compound 194]
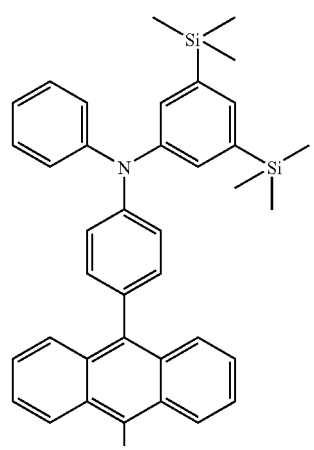
[Compound 195]
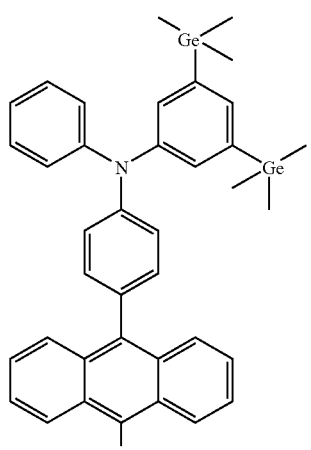
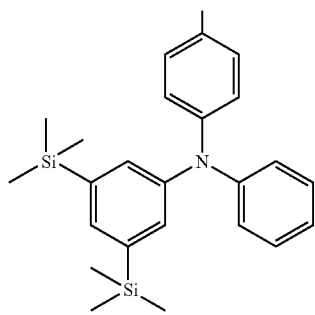
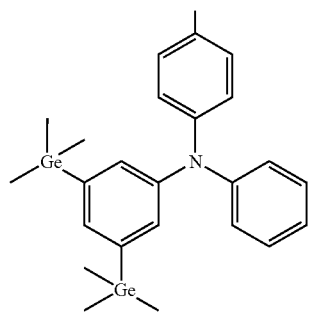

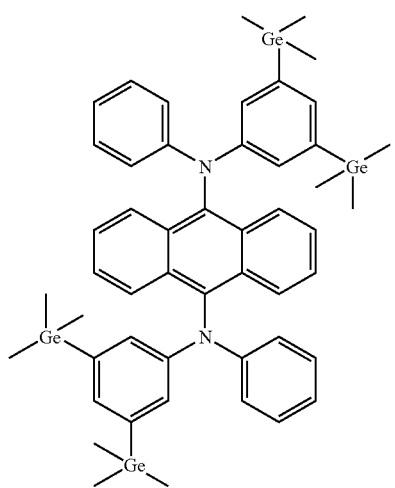

[Compound 196]

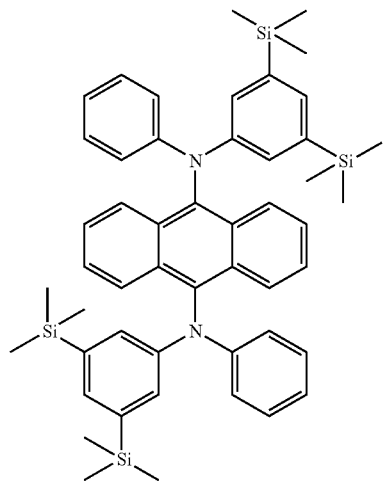

[Compound 197]

Further, the present invention provides a method for preparing the diamine derivative represented by the formula 1.

The diamine derivative according to the present invention can be prepared by reacting a dibromoaryl compound with an arylamine compound in the presence of a palladium catalyst.

The arylamine compound preferably contains at least one selected from a germanium group, a silyl group, and deuterium.

Further, the present invention provides an organic electronic device using the compound of the formula 1.

The organic electronic device of the present invention can be prepared by usual methods and materials for preparing an organic electronic device, except that the above-described compounds are used to form at least one organic material layer.

Hereinbelow, the organic light emitting device will be exemplified.

The above-described compounds can serve as a hole injecting, hole transporting, electron injecting, electron transporting, or light emitting material, and particularly serve as a light emitting material as used alone, as well as a light emitting host with an appropriate light emitting dopant or a light emitting dopant, in particular a blue dopant with an appropriate light emitting host.

In one embodiment of the present invention, the organic light emitting device may have a structure that comprises a first electrode, a second electrode and organic material layers interposed therebetween, and can be prepared by usual methods and materials for preparing an organic light emitting device, except that the above-described compound according to the present invention is used to form at least one of the organic material layers in an organic light emitting device.

The structure of the organic light emitting device according to the present invention is shown in FIG. 1.

For example, the organic light emitting device according to the present invention can be prepared by method using a PVD (physical vapor deposition) process such as sputtering and e-beam evaporation, said method comprising:
depositing a metal, a metal oxide having conductivity or an alloy thereof on a substrate to form an anode; forming an organic material layer comprising a hole injecting layer, a hole transporting layer, a light emitting layer, and an electron transporting layer on said anode; and depositing a material, which can be used as a cathode, thereon. Alternatively, the organic light emitting device can be prepared by sequentially depositing a cathode material, an organic material layer, and an anode material on a substrate.

The organic material layer may be of a multilayer structure containing a hole injecting layer, a hole transporting layer, a light emitting layer, an electron transporting layer, and the like, but not limited thereto, and may be of a monolayer structure. Further, the organic material layer can be produced to have a fewer number of layers, by using a variety of polymeric materials, by means of a solvent process rather than a deposit process, such as spin coating, dip coating, doctor blading, screen printing, ink jet printing, and heat transfer processes.

The anode material is preferably a material having a large work function to facilitate hole injection usually to an organic material layer. Specific examples of the anode material which can be used in the present invention include metals such as vanadium, chromium, copper, zinc and gold, or an alloy thereof; metal oxides such as zinc oxide, indium oxide, indium-tin oxide (ITO), and indium zinc oxide (IZO); a combination of a metal and an oxide such as ZnO:Al and $SnO_2$:Sb; conductive polymers such as poly(3-methylthiophene), poly[3,4-(ethylene-1,2-dioxy)thiophene](PEDT), polypyrrole and polyaniline, but not limited thereto.

The cathode material is preferably a material having a small work function to facilitate electron injection usually to an organic material layer. Specific examples of the cathode material include metals such as magnesium, calcium, sodium, potassium, titanium, indium, yttrium, lithium, gadolinium, aluminum, silver, tin and lead, or an alloy thereof; multilayer structure materials such as LiF/Al and $LiO_2$/Al, but not limited thereto.

The hole injecting material is a material facilitating hole injection from an anode at low voltage. The HOMO (highest occupied molecular orbital) level of the hole injecting material is preferably located between the work function of the anode materials and the HOMO level of its neighboring organic material layer. Specific examples of the hole injecting material include organic materials of metal porphyrin, oligothiophene and arylamine series, organic materials of hexanitrile hexaazatriphenylene and quinacridone series, organic materials of perylene series, and conductive polymers of anthraquinone, polyaniline, and polythiophene series, but are not limited thereto.

The hole transporting material is preferably a material having high hole mobility, which can transfer holes from the anode or the hole injecting layer toward the light emitting layer. Specific examples thereof include organic materials of arylamine series, conductive polymers and block copolymers having both conjugated portions and non-conjugated portions, but are not limited thereto.

The light emitting material are a material capable of emitting visible light by accepting and recombining holes from the hole transporting layer and electrons from the electron transporting layer, preferably a material having high quantum efficiency for fluorescence and phosphorescence. Specific examples thereof include 8-hydroxy-quinoline aluminum complex (Alq$_3$); compounds of carbazole series; dimerized styryl compounds; BAlq; 10-hydroxybenzoquinoline-metal compounds; compounds of benzoxazole, benzthiazole and benzimidazole series; polymers of poly(p-phenylenevinylene) (PPV) series; spiro compounds; and compounds of polyfluorene and rubrene series, but are not limited thereto.

The electron transporting material is suitably a material having high electron mobility, which can transfer electrons from the cathode to the light emitting layer. Specific examples thereof include 8-hydroxyquinoline aluminum complex; complexes including Alq$_3$; organic radical compounds; and hydroxyflavone-metal complexes, but are not limited thereto.

The organic light emitting device according to the invention may be of a front-side, backside or double-side light emission according to the materials used.

The compound according to the invention can function in an organic electronic device including an organic solar cell, an organic photoconductor and an organic transistor, according to a principle similar to that applied to the organic light emitting device.

Mode For Invention

Hereinbelow, the preferred Examples of the present invention will be presented for further understanding the present invention. However, the following Examples are presented merely for illustrative purpose, and thus do not limit the scope of the present invention.

The compound of the formula I according to the present invention can be prepared in multi-step chemical reactions. The preparation of the compound is described by way of Examples below. As will be clear in Examples, a certain intermediate compound is first prepared, and then the intermediate compound is used to prepare the compound of the formula I. Exemplary intermediate compounds are listed below as Compounds A through M. In these compounds, "Br" may be substituted with any other reactive atoms or functional groups.

[Compound A]
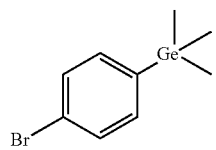

[Compound B]
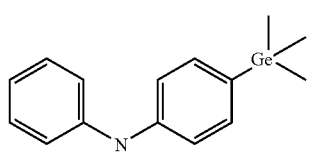

[Compound C]
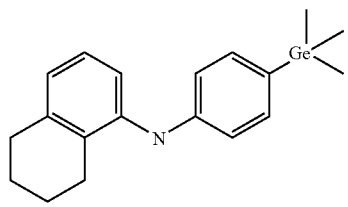

[Compound D]
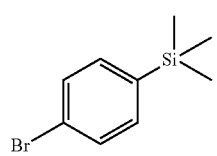

[Compound E]
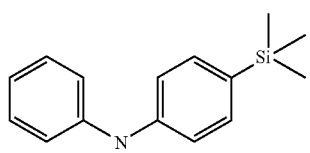

[Compound F]
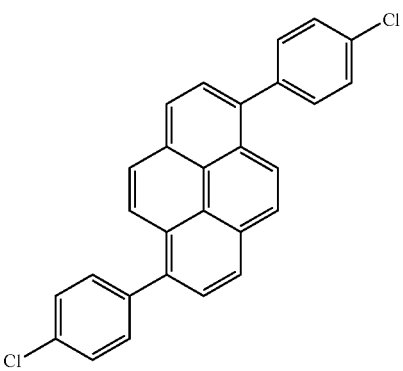

[Compound G]
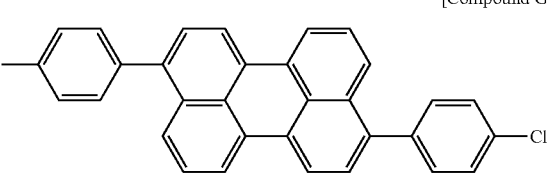

[Compound H]
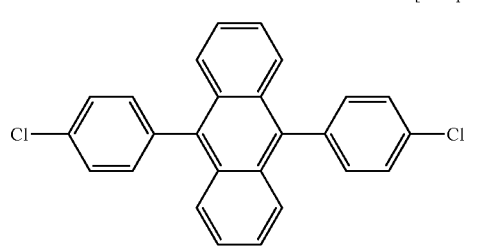

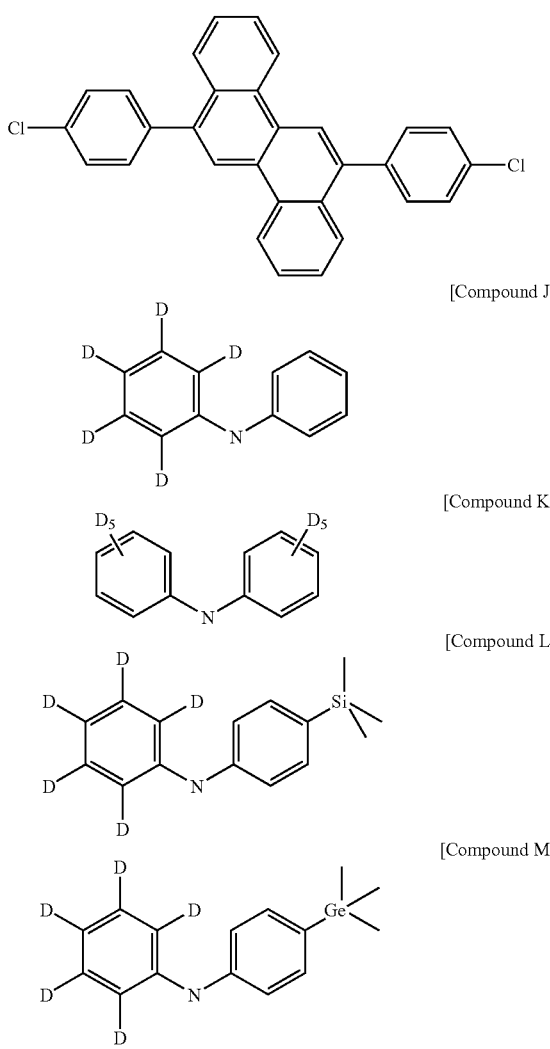

[Compound I]

[Compound J]

[Compound K]

[Compound L]

[Compound M]

PREPARATION EXAMPLE 1

Preparation of Compound A

Dibromobenzene (20 g, 84.78 mmol) was dissolved in anhydrous tetrahydrofuran (THF, 200 mL) at room temperature under nitrogen atmosphere. The solution was cooled to −78° C. n-butyllithium (34 mL, 2.5 M pentane solution) was added slowly to the solution at −78° C., and the temperature of the mixture was slowly raised to 0° C. for about 1 hour. To the mixture, trimethylgerumanium bromide (18 ml, 101.74 mmol) was added, and the temperature of the mixture was raised to room temperature over 1 hour. After confirmation of completion of the reaction, the mixture was extracted from ethyl acetate, dried over magnesium sulfate, and distilled off under reduced pressure to obtain a compound A (20 g, 90%). MS (M+) 273

PREPARATION EXAMPLE 2

Preparation of Compound B

The compound A (18 g, 65.45 mmol), aniline (6.6 ml, 72 mmol), pd(dba)$_2$ (0.125 g, 0.13 mmol), P(t-Bu)$_3$ (0.04 g, 0.2 mmol) and sodium t-butoxide (1.80 g, 18.7 mmol) were added to toluene (200 mL) under nitrogen atmosphere, and the mixture was refluxed for about 3 hours. After completion of the reaction, the mixture was cooled to room temperature, and the reaction mixture was added to a mixed solution of THF and H$_2$O. The organic layer was separated, dried over magnesium sulfate, and then concentrated. The residue was separated by column chromatography to obtain a compound B (16 g, 85%). MS [M]=286

PREPARATION EXAMPLE 3

Preparation of Compound C

A compound C (17 g, 78%) was prepared in the same manner as in Preparation Example 2, except that 5,6,7,8-tetrahydro-1-naphthylamine (10.6 g, 72 mmol) was used instead of aniline (6.6 ml, 72 mmol) in Preparation Example 2. MS [M]=340

PREPARATION EXAMPLE 4

Preparation of Compound D

Dibromobenzene (20 g, 84.78 mmol) was dissolved in anhydrous tetrahydrofuran (THF, 200 mL) at room temperature under nitrogen atmosphere. The solution was cooled to −78° C. n-butyllithium (34 mL, 2.5 M pentane solution) was added slowly to the solution at −78° C., and the temperature of the mixture was slowly raised to 0° C. for about 1 hour. To the mixture, chlorotrimethylsilane (13 ml, 101.74 mmol) was added, and the temperature of the mixture was raised to room temperature over 1 hour. After confirmation of completion of the reaction, the mixture was extracted from ethyl acetate, dried over magnesium sulfate, and distilled off under reduced pressure to obtain a compound D (18 g, 93%). MS (M+)=229

PREPARATION EXAMPLE 5

Preparation of Compound E

The compound D (15 g, 65.45 mmol), aniline (6.6 ml, 72 mmol), pd(dba)$_2$ (0.125 g, 0.13 mmol), P(t-Bu)$_3$ (0.04 g, 0.2 mmol) and sodium t-butoxide (1.80 g, 18.7 mmol) were added to toluene (200 mL) under nitrogen atmosphere, and the mixture was refluxed for about 3 hours. After completion of the reaction, the mixture was cooled to room temperature, and the reaction mixture was added to a mixed solution of THF and H$_2$O. The organic layer was separated, dried over magnesium sulfate, and then concentrated. The residue was separated by column chromatography to obtain a compound E (15 g, 86%). MS [M]=143

PREPARATION EXAMPLE 6

Preparation of Compound F 1,6-Dibromopyrene (3 g, 8.5 mmol), 4-chlorophenylboronic acid (2.9 g, 18.7 mmol), and Pd(PPh$_3$)$_4$ (0.29 g, 0.26 mmol) were added to an aqueous 2 M K$_2$CO$_3$ solution (20 mL) and THF (80 mL) under nitrogen atmosphere. The mixture was refluxed under stirring for about 12 hours. After completing the reaction, the mixture was cooled to room temperature. The organic layer was separated from the reaction mixture, dried over magnesium sulfate, and distilled under reduced pressure. The residue was purified by column chromatography to prepare a compound F (2.5 g, 70%). MS [M+H]+=422

PREPARATION EXAMPLE 7

Preparation of Compound G 3,9-Dibromoperylene (3.5 g, 8.5 mmol), 4-chlorophenylboronic acid (2.9 g, 18.7 mmol), and Pd(PPh$_3$)$_4$ (0.29 g, 0.26 mmol) were added to an aqueous 2 M K$_2$CO$_3$ solution (20 mL) and THF (80 mL) under nitrogen atmosphere. The mixture was refluxed under stirring for about 12 hours. After completing the reaction, the mixture was cooled to room temperature. The organic layer was separated from the reaction mixture, dried over magnesium sulfate, and distilled under reduced pressure. The residue was purified by column chromatography to prepare a compound G (3.0 g, 75%). MS [M+H]+=472

PREPARATION EXAMPLE 8

Preparation of Compound H 9,10-Dibromoanthracene (2.86 g, 8.5 mmol), 4-chlorophenylboronic acid (2.9 g, 18.7 mmol), and Pd(PPh$_3$)$_4$ (0.29 g, 0.26 mmol) were added to an aqueous 2 M K$_2$CO$_3$ solution (20 mL) and THF (80 mL) under nitrogen atmosphere. The mixture was refluxed under stirring for about 12 hours. After completing the reaction, the mixture was cooled to room temperature. The organic layer was separated from the reaction mixture, dried over magnesium sulfate, and distilled under reduced pressure. The residue was purified by column chromatography to prepare a compound H (3.0 g, 90%). MS [M+H]+=398

PREPARATION EXAMPLE 9

Preparation of Compound I 9,10-Dibromochrysene (3.28 g, 8.5 mmol), 4-chlorophenylboronic acid (2.9 g, 18.7 mmol), and Pd(PPh$_3$)$_4$ (0.29 g, 0.26 mmol) were added to an aqueous 2 M K$_2$CO$_3$ solution (20 mL) and THF (80 mL) under nitrogen atmosphere. The mixture was refluxed under stirring for about 12 hours. After completing the reaction, the mixture was cooled to room temperature. The organic layer was separated from the reaction mixture, dried over magnesium sulfate, and distilled under reduced pressure. The residue was purified by column chromatography to prepare a compound I (2.9 g, 75%). MS [M+H]±=448

PREPARATION EXAMPLE 10

Preparation of Compound J

Bromobenzene-d$_5$ (10.6 g, 65.45 mmol), aniline (6.6 ml, 72 mmol), pd(dba)$_2$ (0.125 g, 0.13 mmol), P(t-Bu)$_3$ (0.04 g, 0.2 mmol) and sodium t-butoxide (1.80 g, 18.7 mmol) were added to toluene (80 mL) under nitrogen atmosphere, and the mixture was refluxed for about 3 hours. After completion of the reaction, the mixture was cooled to room temperature, and the reaction mixture was added to a mixed solution of THF and H$_2$O. The organic layer was separated, dried over magnesium sulfate, and then concentrated. The residue was separated by column chromatography to obtain a compound J (16 g, 85%). MS [M]=174

PREPARATION EXAMPLE 11

Preparation of Compound K

Bromobenzene-d$_5$ (10.6 g, 65.45 mmol), aniline-2,3,4,5,6-D5 (6.6 ml, 72 mmol), pd(dba)$_2$ (0.125 g, 0.13 mmol), P(t-Bu)$_3$ (0.04 g, 0.2 mmol) and sodium t-butoxide (1.80 g, 18.7 mmol) were added to toluene (80 mL) under nitrogen atmosphere, and the mixture was refluxed for about 3 hours. After completion of the reaction, the mixture was cooled to room temperature, and the reaction mixture was added to a mixed solution of THF and H$_2$O. The organic layer was separated, dried over magnesium sulfate, and then concentrated. The residue was separated by column chromatography to obtain a compound K (16 g, 85%). MS [M]=179

PREPARATION EXAMPLE 12

Preparation of Compound L

The compound D of Preparation Example 4 (15 g, 65.45 mmol), aniline-2,3,4,5,6-D5 (6.6 ml, 72 mmol), pd(dba)$_2$ (0.125 g, 0.13 mmol), P(t-Bu)$_3$ (0.04 g, 0.2 mmol) and sodium t-butoxide (1.80 g, 18.7 mmol) were added to toluene (80 mL) under nitrogen atmosphere, and the mixture was refluxed for about 3 hours. After completion of the reaction, the mixture was cooled to room temperature, and the reaction mixture was added to a mixed solution of THF and H$_2$O. The organic layer was separated, dried over magnesium sulfate, and then concentrated. The residue was separated by column chromatography to obtain a compound L (16 g, 85%). MS [M]=246

PREPARATION EXAMPLE 13

Preparation of Compound M

The compound A of Preparation Example 1 (18 g, 65.45 mmol), aniline-2,3,4,5,6-D5 (6.6 ml, 72 mmol), pd(dba)$_2$ (0.125 g, 0.13 mmol), P(t-Bu)$_3$ (0.04 g, 0.2 mmol) and sodium t-butoxide (1.80 g, 18.7 mmol) were added to toluene (80 mL) under nitrogen atmosphere, and the mixture was refluxed for about 3 hours. After completion of the reaction, the mixture was cooled to room temperature, and the reaction mixture was added to a mixed solution of THF and H$_2$O. The organic layer was separated, dried over magnesium sulfate, and then concentrated. The residue was separated by column chromatography to obtain a compound M (16 g, 85%). MS [M]=291

EXAMPLE 1

Preparation of Compound 1

1,6-Dibromopyrene (3.0 g, 8.5 mmol), the compound B (5.83 g, 20.4 mmol), Pd(dba)$_2$ (0.097 g, 0.17 mmol), P(t-Bu)$_3$ (0.05 g, 0.255 mmol) and sodium t-butoxide (2.45 g, 25.5 mmol) were added to toluene (100 mL) under nitrogen atmosphere, and the mixture was refluxed for about 2 hours. After completion of the reaction, the mixture was cooled to room temperature, and the reaction mixture was added to a mixed solution of THF and H$_2$O. The organic layer was separated, dried over MgSO$_4$, and then concentrated. The residue was separated by column chromatography to obtain a compound 1 (4.06 g, 62%). MS [M]=770

EXAMPLE 2

Preparation of Compound 21

A compound 21 (4.18 g, 60%) was prepared in the same manner as in Example 1, except that 3,9-dibromoperylene (3.5 g, 8.5 mmol) was used instead of 1,6-dibromopyrene (3.0 g, 8.5 mmol) in Example 1. MS [M]=820

EXAMPLE 3

Preparation of Compound 23

A compound 23 (5.05 g, 64%) was prepared in the same manner as in Example 1, except that 3,9-dibromoperylene (3.5 g, 8.5 mmol) was used instead of 1,6-dibromopyrene (3.0 g, 8.5 mmol), and the compound C (6.94 g, 20.4 mmol) was used instead of the compound B (5.83 g, 20.4 mmol) in Example 1. MS [M]=928

EXAMPLE 4

Preparation of Compound 27

A compound 27 (3.85 g, 62%) was prepared in the same manner as in Example 1, except that 3,9-dibromoperylene (3.5 g, 8.5 mmol) was used instead of 1,6-dibromopyrene (3.0 g, 8.5 mmol), and the compound E (2.92 g, 20.4 mmol) was used instead of the compound B (5.83 g, 20.4 mmol) in Example 1. MS [M]=730

EXAMPLE 5

Preparation of Compound 36

A compound 36 (4.12 g, 65%) was prepared in the same manner as in Example 1, except that 9,10-dibromoanthracene (2.86 g, 8.5 mmol) was used instead of 1,6-dibromopyrene (3.0 g, 8.5 mmol) in Example 1. MS [M]=746

EXAMPLE 6

Preparation of Compound 40

A compound 40 (3.42 g, 65%) was prepared in the same manner as in Example 1, except that 9,10-dibromoanthracene (2.86 g, 8.5 mmol) was used instead of 1,6-dibromopyrene (3.0 g, 8.5 mmol), and the compound C (6.94 g, 20.4 mmol) was used instead of the compound B (5.83 g, 20.4 mmol) in Example 1. MS [M]=620

EXAMPLE 7

Preparation of Compound 45

A compound 45 (3.63 g, 65%) was prepared in the same manner as in Example 1, except that 9,10-dibromoanthracene (2.86 g, 8.5 mmol) was used instead of 1,6-dibromopyrene (3.0 g, 8.5 mmol), and the compound E (4.55 g, 20.4 mmol) was used instead of the compound B (5.83 g, 20.4 mmol) in Example 1. MS [M]=656

EXAMPLE 8

Preparation of Compound 53

A compound 53 (2.00 g, 61%) was prepared in the same manner as in Example 1, except that 9,10-Dibromochrysene (3.28 g, 8.5 mmol) was used instead of 1,6-dibromopyrene (3.0 g, 8.5 mmol), and the compound C (6.94 g, 20.4 mmol) was used instead of the compound B (5.83 g, 20.4 mmol) in Example 1. MS [M]=386

EXAMPLE 9

Preparation of Compound 56

A compound 56 (3.9 g, 65%) was prepared in the same manner as in Example 1, except that 9,10-Dibromochrysene (3.28 g, 8.5 mmol) was used instead of 1,6-dibromopyrene (3.0 g, 8.5 mmol), and the compound E (2.92 g, 20.4 mmol) was used instead of the compound B (5.83 g, 20.4 mmol) in Example 1. MS [M]=706

EXAMPLE 10

Preparation of Compound 64

A compound 64 (4.86 g, 62%) was prepared in the same manner as in Example 1, except that the compound F (3.6 g, 8.5 mmol) synthesized in Preparation Example 6 was used instead of 1,6-dibromopyrene (3.0 g, 8.5 mmol) in Example 1. MS [M]=922

EXAMPLE 11

Preparation of Compound 73

A compound 73 (5.37 g, 65%) was prepared in the same manner as in Example 1, except that the compound G (4.0 g, 8.5 mmol) synthesized in Preparation Example 7 was used instead of 1,6-dibromopyrene (3.0 g, 8.5 mmol) in Example 1. MS [M]=972

EXAMPLE 12

Preparation of Compound 77

A compound 77 (4.87 g, 65%) was prepared in the same manner as in Example 1, except that the compound G (4.0 g, 8.5 mmol) synthesized in Preparation Example 7 was used instead of 1,6-dibromopyrene (3.0 g, 8.5 mmol), and the compound E (2.92 g, 20.4 mmol) was used instead of the compound B (5.83 g, 20.4 mmol) in Example 1. MS [M]=882

EXAMPLE 13

Preparation of Compound 81

A compound 81 (4.96 g, 65%) was prepared in the same manner as in Example 1, except that the compound H (3.4 g, 8.5 mmol) synthesized in Preparation Example 8 was used instead of 1,6-dibromopyrene (3.0 g, 8.5 mmol) in Example 1. MS [M]=898

EXAMPLE 14

Preparation of Compound 86

A compound 86 (4.46 g, 65%) was prepared in the same manner as in Example 1, except that the compound H (3.4 g, 8.5 mmol) synthesized in Preparation Example 8 was used instead of 1,6-dibromopyrene (3.0 g, 8.5 mmol), and the compound E (2.92 g, 20.4 mmol) was used instead of the compound B (5.83 g, 20.4 mmol) in Example 1. MS [M]=808

EXAMPLE 15

Preparation of Compound 90

A compound 90 (5.24 g, 65%) was prepared in the same manner as in Example 1, except that the compound I (3.4 g, 8.5 mmol) synthesized in Preparation Example 9 was used instead of 1,6-dibromopyrene (3.0 g, 8.5 mmol) in Example 1. MS [M]=948

EXAMPLE 16

Preparation of Compound 94

A compound 94 (4.74 g, 65%) was prepared in the same manner as in Example 1, except that the compound I (3.4 g, 8.5 mmol) synthesized in Preparation Example 9 was used instead of 1,6-dibromopyrene (3.0 g, 8.5 mmol), and the compound E (2.92 g, 20.4 mmol) was used instead of the compound B (5.83 g, 20.4 mmol) in Example 1. MS [M]=858

EXAMPLE 17

Preparation of Compound 98

A compound 98 (3.02 g, 65%) was prepared in the same manner as in Example 1, except that the compound J (3.55 g, 20.4 mmol) was used instead of the compound B (5.83 g, 20.4 mmol) in Example 1. MS [M]=546

EXAMPLE 18

Preparation of Compound 103

A compound 103 (2.93 g, 62%) was prepared in the same manner as in Example 1, except that the compound K (3.66 g, 20.4 mmol) was used instead of the compound B (5.83 g, 20.4 mmol) in Example 1. MS [M]=556

EXAMPLE 19

Preparation of Compound 110

A compound 110 (3.046 g, 59%) was prepared in the same manner as in Example 1, except that the compound L (5.07 g, 20.4 mmol) was used instead of the compound B (5.83 g, 20.4 mmol) in Example 1. MS [M]=690

EXAMPLE 20

Preparation of Compound 111

A compound 111 (4.04 g, 61%) was prepared in the same manner as in Example 1, except that the compound M (5.94 g, 20.4 mmol) was used instead of the compound B (5.83 g, 20.4 mmol) in Example 1. MS [M]=780

EXAMPLE 21

Preparation of Compound 119

A compound 119 (3.68 g, 62%) was prepared in the same manner as in Example 1, except that the compound F (3.6 g, 8.5 mmol) synthesized in Preparation Example 6 was used instead of 1,6-dibromopyrene (3.0 g, 8.5 mmol), and the compound J (3.55 g, 20.4 mmol) was used instead of the compound B (5.83 g, 20.4 mmol) in Example 1. MS [M]=698

EXAMPLE 22

Preparation of Compound 120

A compound 120 (3.61 g, 60%) was prepared in the same manner as in Example 1, except that the compound F (3.6 g, 8.5 mmol) synthesized in Preparation Example 6 was used instead of 1,6-dibromopyrene (3.0 g, 8.5 mmol), and the compound K (3.66 g, 20.4 mmol) was used instead of the compound B (5.83 g, 20.4 mmol) in Example 1. MS [M]=708

EXAMPLE 23

Preparation of Compound 121

A compound 121 (4.43 g, 62%) was prepared in the same manner as in Example 1, except that the compound F (3.6 g, 8.5 mmol) synthesized in Preparation Example 6 was used instead of 1,6-dibromopyrene (3.0 g, 8.5 mmol), and the compound L (5.07 g, 20.4 mmol) was used instead of the compound B (5.83 g, 20.4 mmol) in Example 1. MS [M]=842

EXAMPLE 24

Preparation of Compound 122

A compound 122 (4.75 g, 60%) was prepared in the same manner as in Example 1, except that the compound F (3.6 g, 8.5 mmol) synthesized in Preparation Example 6 was used instead of 1,6-dibromopyrene (3.0 g, 8.5 mmol), and the compound M (5.94 g, 20.4 mmol) was used instead of the compound B (5.83 g, 20.4 mmol) in Example 1. MS [M]=932

EXAMPLE 25

Preparation of Compound 123

A compound 123 (3.14 g, 62%) was prepared in the same manner as in Example 1, except that 3,9-dibromoperylene (3.5 g, 8.5 mmol) was used instead of 1,6-dibromopyrene (3.0 g, 8.5 mmol), and the compound J (3.55 g, 20.4 mmol) was used instead of the compound B (5.83 g, 20.4 mmol) in Example 1. MS [M]=596

EXAMPLE 26

Preparation of Compound 124

A compound 124 (2.63 g, 60%) was prepared in the same manner as in Example 1, except that 3,9-dibromoperylene (3.5 g, 8.5 mmol) was used instead of 1,6-dibromopyrene (3.0 g, 8.5 mmol), and the compound K (3.66 g, 20.4 mmol) was used instead of the compound B (5.83 g, 20.4 mmol) in Example 1. MS [M]=606

EXAMPLE 27

Preparation of Compound 125

A compound 125 (3.96 g, 63%) was prepared in the same manner as in Example 1, except that 3,9-dibromoperylene (3.5 g, 8.5 mmol) was used instead of 1,6-dibromopyrene (3.0 g, 8.5 mmol), and the compound L (5.07 g, 20.4 mmol) was used instead of the compound B (5.83 g, 20.4 mmol) in Example 1. MS [M]=740

EXAMPLE 28

Preparation of Compound 126

A compound 126 (4.23 g, 60%) was prepared in the same manner as in Example 1, except that 3,9-dibromoperylene (3.5 g, 8.5 mmol) was used instead of 1,6-dibromopyrene (3.0 g, 8.5 mmol), and the compound M (5.94 g, 20.4 mmol) was used instead of the compound B (5.83 g, 20.4 mmol) in Example 1. MS [M]=830

EXAMPLE 29

Preparation of Compound 141

A compound 141 (3.94 g, 62%) was prepared in the same manner as in Example 1, except that the compound G (4.0 g, 8.5 mmol) synthesized in Preparation Example 7 was used instead of 1,6-dibromopyrene (3.0 g, 8.5 mmol), and the compound J (3.55 g, 20.4 mmol) was used instead of the compound B (5.83 g, 20.4 mmol) in Example 1. MS [M]=748

EXAMPLE 30

Preparation of Compound 142

A compound 142 (3.87 g, 60%) was prepared in the same manner as in Example 1, except that the compound G (4.0 g, 8.5 mmol) synthesized in Preparation Example 7 was used instead of 1,6-dibromopyrene (3.0 g, 8.5 mmol), and the compound K (3.66 g, 20.4 mmol) was used instead of the compound B (5.83 g, 20.4 mmol) in Example 1. MS [M]=758

EXAMPLE 31

Preparation of Compound 143

A compound 143 (4.78 g, 63%) was prepared in the same manner as in Example 1, except that the compound G (4.0 g, 8.5 mmol) synthesized in Preparation Example 7 was used instead of 1,6-dibromopyrene (3.0 g, 8.5 mmol), and the compound L (5.07 g, 20.4 mmol) was used instead of the compound B (5.83 g, 20.4 mmol) in Example 1. MS [M]=892

EXAMPLE 32

Preparation of Compound 144

A compound 144 (5.00 g, 60%) was prepared in the same manner as in Example 1, except that the compound G (4.0 g, 8.5 mmol) synthesized in Preparation Example 7 was used instead of 1,6-dibromopyrene (3.0 g, 8.5 mmol), and the compound M (5.94 g, 20.4 mmol) was used instead of the compound B (5.83 g, 20.4 mmol) in Example 1. MS [M]=982

EXAMPLE 33

Preparation of Compound 145

A compound 145 (3.57 g, 63%) was prepared in the same manner as in Example 1, except that 9,10-dibromoanthracene (2.86 g, 8.5 mmol) was used instead of 1,6-dibromopyrene (3.0 g, 8.5 mmol), and the compound L (5.07 g, 20.4 mmol) was used instead of the compound B (5.83 g, 20.4 mmol) in Example 1. MS [M]=666

EXAMPLE 34

Preparation of Compound 146

A compound 146 (3.86 g, 60%) was prepared in the same manner as in Example 1, except that 9,10-dibromoanthracene (2.86 g, 8.5 mmol) was used instead of 1,6-dibromopyrene (3.0 g, 8.5 mmol), and the compound M (5.94 g, 20.4 mmol) was used instead of the compound B (5.83 g, 20.4 mmol) in Example 1. MS [M]=756

EXAMPLE 35

Preparation of Compound 156

A compound 156 (4.39 g, 63%) was prepared in the same manner as in Example 1, except that the compound H (3.4 g, 8.5 mmol) synthesized in Preparation Example 8 was used instead of 1,6-dibromopyrene (3.0 g, 8.5 mmol), and the compound L (5.07 g, 20.4 mmol) was used instead of the compound B (5.83 g, 20.4 mmol) in Example 1. MS [M]=818

EXAMPLE 36

Preparation of Compound 158

A compound 158 (4.86 g, 63%) was prepared in the same manner as in Example 1, except that the compound H (3.4 g, 8.5 mmol) synthesized in Preparation Example 8 was used instead of 1,6-dibromopyrene (3.0 g, 8.5 mmol), and the compound M (5.94 g, 20.4 mmol) was used instead of the compound B (5.83 g, 20.4 mmol) in Example 1. MS [M]=908

EXAMPLE 37

Preparation of Compound 161

A compound 161 (3.01 g, 62%) was prepared in the same manner as in Example 1, except that 9,10-Dibromochrysene (3.28 g, 8.5 mmol) was used instead of 1,6-dibromopyrene (3.0 g, 8.5 mmol), and the compound J (3.55 g, 20.4 mmol) was used instead of the compound B (5.83 g, 20.4 mmol) in Example 1. MS [M]=572

EXAMPLE 38

Preparation of Compound 163

A compound 163 (2.97 g, 60%) was prepared in the same manner as in Example 1, except that 9,10-Dibromochrysene (3.28 g, 8.5 mmol) was used instead of 1,6- dibromopyrene (3.0 g, 8.5 mmol), and the compound K (3.66 g, 20.4 mmol) was used instead of the compound B (5.83 g, 20.4 mmol) in Example 1. MS [M]=582

EXAMPLE 39

Preparation of Compound 172

A compound 172 (3.83 g, 63%) was prepared in the same manner as in Example 1, except that 9,10-Dibromochrysene (3.28 g, 8.5 mmol) was used instead of 1,6-dibromopyrene (3.0 g, 8.5 mmol), and the compound L (5.07 g, 20.4 mmol) was used instead of the compound B (5.83 g, 20.4 mmol) in Example 1. MS [M]=716

EXAMPLE 40

Preparation of Compound 173

A compound 173 (4.11 g, 60%) was prepared in the same manner as in Example 1, except that 9,10-Dibromochrysene (3.28 g, 8.5 mmol) was used instead of 1,6-dibromopyrene (3.0 g, 8.5 mmol), and the compound M (5.94 g, 20.4 mmol) was used instead of the compound B (5.83 g, 20.4 mmol) in Example 1. MS [M]=806

EXAMPLE 41

Preparation of Compound 174

A compound 174 (3.82 g, 62%) was prepared in the same manner as in Example 1, except that the compound I (3.4 g, 8.5 mmol) synthesized in Preparation Example 9 was used instead of 1,6-dibromopyrene (3.0 g, 8.5 mmol), and the compound J (3.55 g, 20.4 mmol) was used instead of the compound B (5.83 g, 20.4 mmol) in Example 1. MS [M]=724

EXAMPLE 42

Preparation of Compound 175

A compound 175 (4.00 g, 60%) was prepared in the same manner as in Example 1, except that the compound I (3.4 g, 8.5 mmol) synthesized in Preparation Example 9 was used instead of 1,6-dibromopyrene (3.0 g, 8.5 mmol), and the compound K (3.66 g, 20.4 mmol) was used instead of the compound B (5.83 g, 20.4 mmol) in Example 1. MS [M]=734

EXAMPLE 43

Preparation of Compound 176

A compound 176 (4.65 g, 63%) was prepared in the same manner as in Example 1, except that the compound I (3.4 g, 8.5 mmol) synthesized in Preparation Example 9 was used instead of 1,6-dibromopyrene (3.0 g, 8.5 mmol), and the compound L (5.07 g, 20.4 mmol) was used instead of the compound B (5.83 g, 20.4 mmol) in Example 1. MS [M]=868

EXAMPLE 44

Preparation of Compound 177

A compound 177 (4.89 g, 60%) was prepared in the same manner as in Example 1, except that the compound I (3.4 g, 8.5 mmol) synthesized in Preparation Example 9 was used instead of 1,6-dibromopyrene (3.0 g, 8.5 mmol), and the compound M (5.94 g, 20.4 mmol) was used instead of the compound B (5.83 g, 20.4 mmol) in Example 1. MS [M]=958

EXPERIMENTAL EXAMPLE 1

A glass substrate (Corning 7059 glass), on which a thin film of ITO (indium tin oxide) was coated to a thickness of 1000 Å, was immersed in distilled water having a detergent dissolved therein to wash the substrate with ultrasonic waves. The detergent as used herein was a product commercially available from Fisher Co. and the distilled water was one which had been twice filtered by using a filter commercially available from Millipore Co. ITO was washed for 30 minutes, and then washing with ultrasonic waves was repeated twice for 10 minutes by using distilled water. After the completion of washing with distilled water, washing with ultrasonic waves was carried out by using solvents such as isopropyl alcohol, acetone and methanol. The resultant product was dried, and then transported to a plasma washing machine. The substrate was washed for 5 minutes using an oxygen plasma, and then transported to a vacuum depositing machine.

On the ITO electrode, 3,6-bis-2-naphthylphenylamino-N-[4-(2-naphthylphenyl)aminophenyl]carbazole (800 Å), and 4,4'-bis[N-(1-naphthyl)-N-phenyl amino]biphenyl (NPB) (300 Å) were sequentially deposited to form a hole injecting layer and a hole transporting layer, respectively. The compound 1 (2 wt %) prepared in the Example 1 was deposited thereon with the following compound N (300 Å) to form a light emitting layer, and then 9,10-bis-2-naphthyl-2-[4-(N-phenylbenzoimidazoyl)phenyl]anthracene (300 Å) was coated by thermal vacuum deposition to form an electron transporting layer.

Lithium fluoride (LiF) and aluminum were sequentially deposited on the electron transporting layer to thicknesses of 12 Å and 2000 Å respectively, to form a cathode, thereby obtaining an organic light emitting device. In the above process, the deposition rate of the organic material was maintained at 0.4 to 0.7 Å/sec and the deposition rate of lithium fluoride on the cathode was maintained at 0.3 Å/sec and the deposition rate of aluminum was maintained at 2 Å/sec. The degree of vacuum upon deposition was maintained at $2 \times 10^{-7}$ to $5 \times 10^{-8}$ torr.

When a forward electric field of 7.8 V was applied to the organic light emitting device as prepared above, blue light emission of 4.9 cd/A, which corresponds to x=0.170, and y=0.150 based on the 1931 CIE color coordinate, was observed at a current density of 100 mA/cm².

[Compound N]

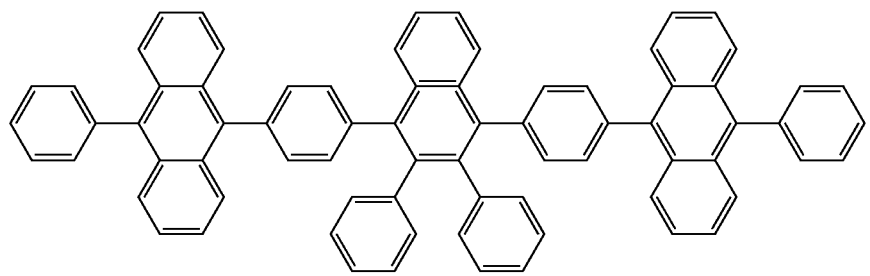

EXPERIMENTAL EXAMPLE 2

An organic light emitting device was prepared in the same manner as in Experimental Example 1, except that the compound 56 was used instead of the compound 1 in Experimental Example 1.

When a forward electric field of 7.9 V was applied to the organic light emitting device as prepared above, blue light emission of 4.7 cd/A, which corresponds to x=0.170, and y=0.151 based on the 1931 CIE color coordinate, was observed at a current density of 100 mA/cm².

EXPERIMENTAL EXAMPLE 3

An organic light emitting device was prepared in the same manner as in Experimental Example 1, except that the compound 86 was used instead of the compound 1 in Experimental Example 1.

When a forward electric field of 7.7 V was applied to the organic light emitting device as prepared above, blue light emission of 4.8 cd/A, which corresponds to x=0.171, and y=0.153 based on the 1931 CIE color coordinate, was observed at a current density of 100 mA/cm².

EXPERIMENTAL EXAMPLE 4

An organic light emitting device was prepared in the same manner as in Experimental Example 1, except that the compound 111 was used instead of the compound 1 in Experimental Example 1.

When a forward electric field of 7.7 V was applied to the organic light emitting device as prepared above, blue light emission of 4.9 cd/A, which corresponds to x=0.171, and y=0.153 based on the 1931 CIE color coordinate, was observed at a current density of 100 mA/cm².

EXPERIMENTAL EXAMPLE 5

An organic light emitting device was prepared in the same manner as in Experimental Example 1, except that the compound 156 was used instead of the compound 1 in Experimental Example 1.

When a forward electric field of 7.8 V was applied to the organic light emitting device as prepared above, blue light emission of 4.8 cd/A, which corresponds to x=0.172, and y=0.153 based on the 1931 CIE color coordinate, was observed at a current density of 100 mA/cm².

EXPERIMENTAL EXAMPLE 6

An organic light emitting device was prepared in the same manner as in Experimental Example 1, except that the compound 173 was used instead of the compound 1 in Experimental Example 1.

When a forward electric field of 7.9 V was applied to the organic light emitting device as prepared above, blue light emission of 4.9 cd/A, which corresponds to x=0.173, and y=0.152 based on the 1931 CIE color coordinate, was observed at a current density of 100 mA/cm².

The invention claimed is:

1. A diamine derivative represented by the following formula 1:

[Formula 1]

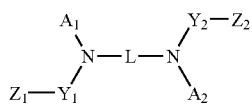

wherein

L is from the group consisting of anthracenyl, perylenyl, chrysenyl,

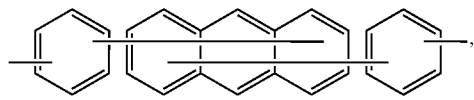

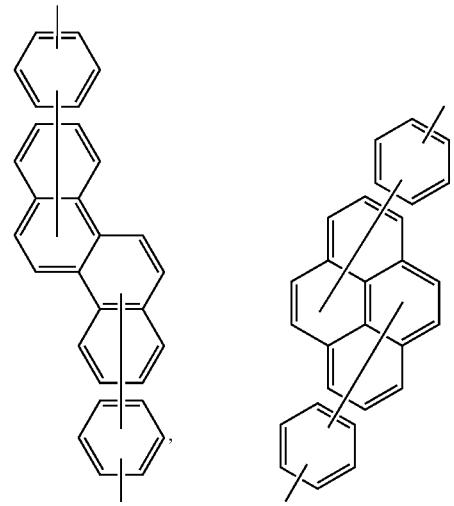

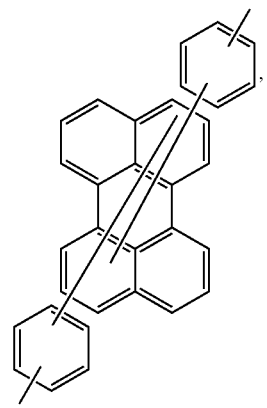

when L is anthracenyl,

A1 and A2 are the same or different from each other, and are each

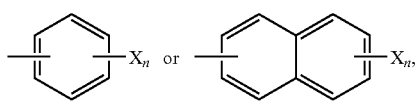

wherein n is an integer from 1 to 5, and at least one of Xs is selected from the group consisting of —GeRR'R" and deuterium (D), and the others are each independently selected from the group consisting of hydrogen, CN, NO$_2$, a C$_6$ to C$_{20}$ arylamine group, a C$_6$ to C$_{20}$ arylthiophene group, a C$_3$ to C$_{20}$ cycloalkyl group, —OR, —SR, —SeR, —TeR, —BRR', —AIRR', —SnRR'R", a C$_6$ to C$_{20}$ aryl group, a C$_8$ to C$_{20}$ arylalkenyl group, and a C$_4$ to C$_{20}$ alkylene group which formed a fused ring with the phenyl group or the naphthyl group, Y$_1$ and Y$_2$ are the same or different from each other, and are each a C$_6$ to C$_{20}$ arylene group or a divalent C$_5$ to C$_{20}$ heterocyclic group, Z$_1$ and Z$_2$ are the same or different from each other, and are each hydrogen, halogen, deuterium, CN, NO$_2$, a C$_1$ to C$_{20}$ alkyl group, a C$_1$ to C$_{20}$ alkoxy group, a C$_6$ to C$_{20}$ aryl group, a C$_6$ to C$_{20}$ arylamine group, a C$_6$ to C$_{20}$ arylthiophene group, a C$_3$ to C$_{20}$ cycloalkyl group, —OR, —SR, —SeR, —TeR, —BRR', —AIRR', —GeRR'R", -SnRR'R", a C$_6$ to C$_{20}$ aryl group, a C$_8$ to C$_{20}$ arylalkenyl group, and a C$_4$ to C$_{20}$ alkylene group which formed a fused ring with the phenyl group or the naphthyl group, and R, R' and R" are the same or different from each other, and are each hydrogen, a C$_1$ to C$_{20}$ alkyl group, a C$_3$ to C$_{20}$ cycloalkyl group, a C$_6$ to C$_{20}$ aryl group, or a C$_5$ to C$_{20}$ heterocyclic group;

when L is phenanthrenyl, perylenyl, chrysenyl,

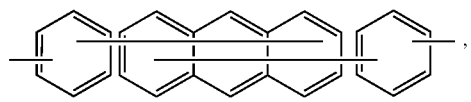,

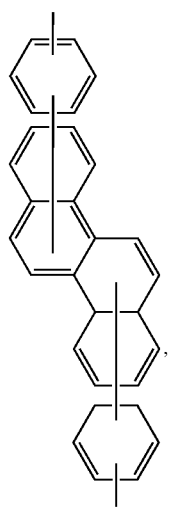

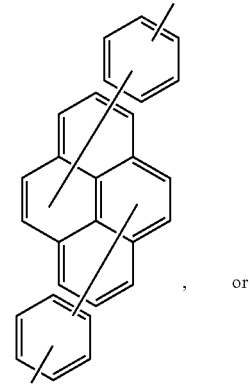 or

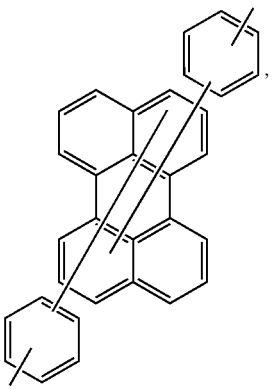,

A$_1$ and A$_2$, are the same or different from each other, and are each

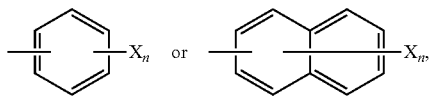

wherein n is an integer from 1 to 5, and at least one of Xs is selected from the group consisting of —GeRR'R", —SiRR'R" and deuterium (D), and the others are each independently selected from the group consisting of hydrogen, CN, NO$_2$, a C$_6$ to C$_{20}$ arylamine group, a C$_6$ to C$_{20}$ arylthiophene group, a C$_3$ to C$_{20}$ cycloalkyl group, —OR, —SR, —SeR, —TeR, —BRR', —AIRR', —SnRR'R", a C$_6$ to C$_{20}$ aryl group, a C$_8$ to C$_{20}$ arylalkenyl group, and a C$_4$ to C$_{20}$ alkylene group which formed a fused ring with the phenyl group or the naphthyl group, Y$_1$ and Y$_2$ are the same or different from each other, and are each a C$_6$ to C$_{20}$ arylene group or a divalent C$_5$ to C$_{20}$ heterocyclic group, Z$_1$, and Z$_2$ are the same or different from each other, and are each hydrogen, halogen, deuterium, CN, NO$_2$, a C$_1$ to C$_{20}$ alkyl group, a C$_1$ to C$_{20}$ alkoxy group, a C$_6$ to C$_{20}$ aryl group, a C$_6$ to C$_{20}$ arylamine group, a C$_6$ to C$_{20}$ arylthiophene group, a C$_3$ to C$_{20}$ cycloalkyl group, —OR, —SR, —SeR, —TeR, —BRR', —AIRR', —SiRR'R", —GeRR'R", —SnRR'R", a C$_6$ to C$_{20}$ aryl group, a C$_8$ to C$_{20}$ arylalkenyl group, and a C$_4$ to C$_{20}$ alkylene group which formed a fused ring with the phenyl group or the naphthyl group, and R, R' and R" are the same or different from each other, and are each hydrogen, a C$_1$ to C$_{20}$ alkyl group, a C$_3$ to C$_{20}$ cycloalkyl group, a C$_6$ to C$_{20}$ aryl group, or a C$_5$ to C$_{20}$ heterocyclic group.

2. The diamine derivative according to claim 1, wherein Y$_1$ and Y$_2$ are selected from the group consisting of phenyl, biphenyl, naphthalenyl, tetralinyl, anthracenyl, stilbenyl, phenanthrenyl, pyrenyl, perylenyl, chrysenyl, and carbazolyl.

3. The diamine derivative according to claim 1, wherein the compound of the formula 1 is selected from the group consisting of the following compounds:

[Compound 20]
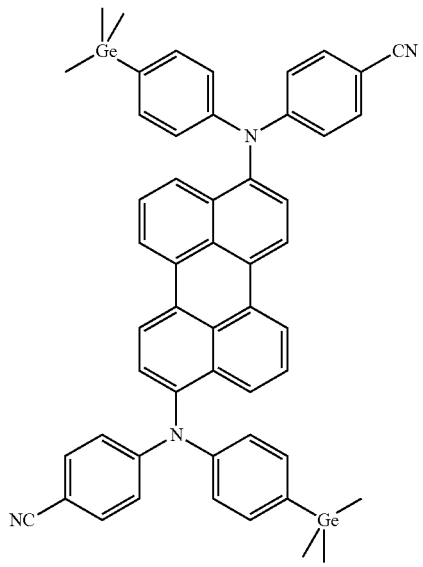
[Compound 21]
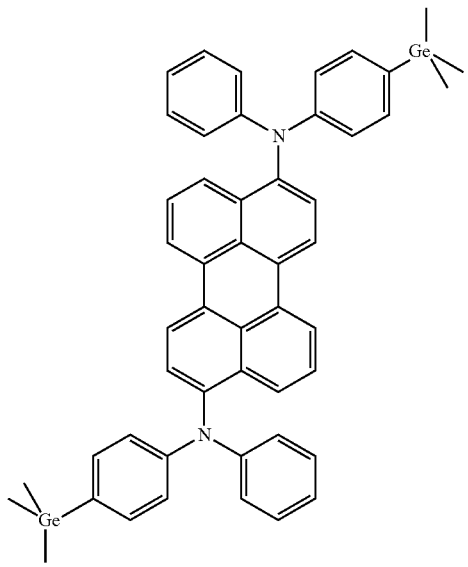
[Compound 22]
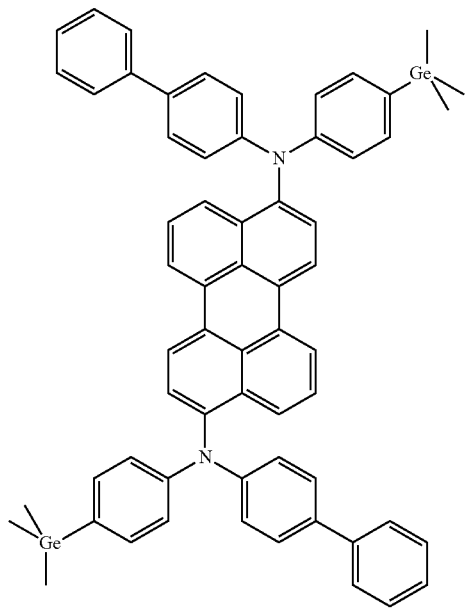
[Compound 23]
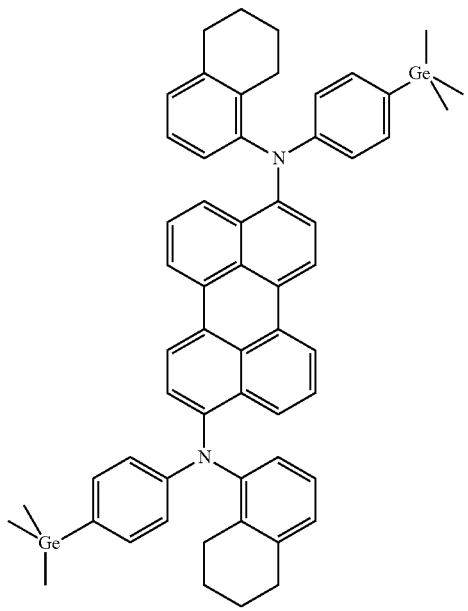

[Compound 24]
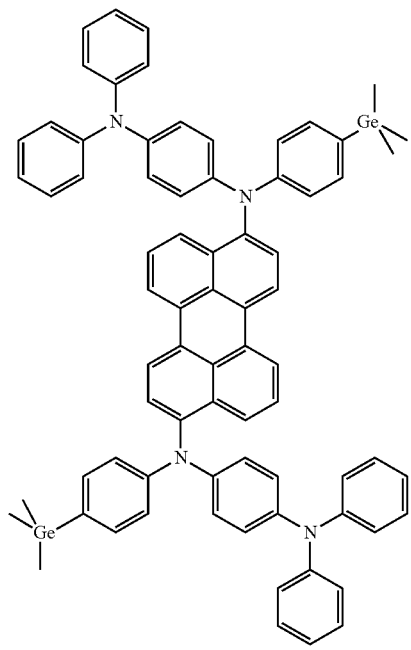
[Compound 25]
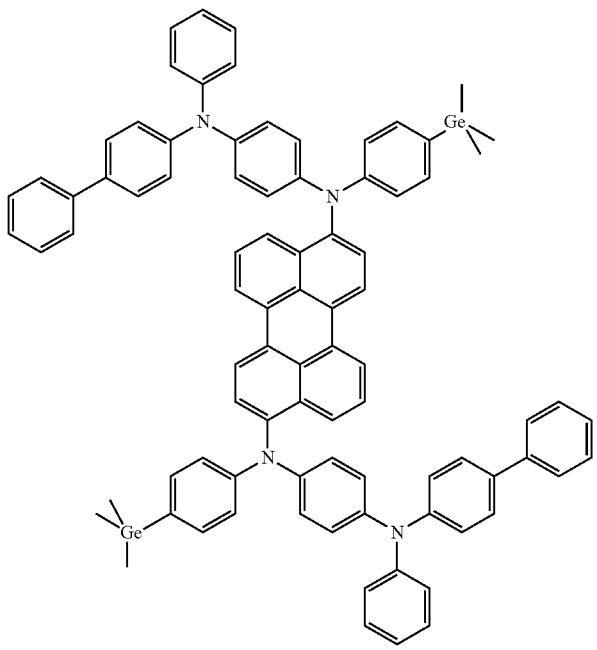
[Compound 26]
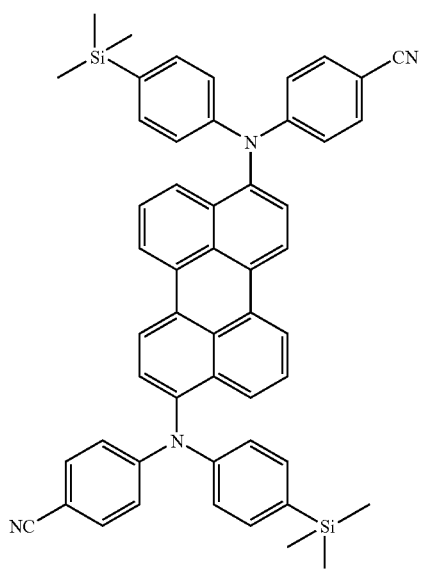
[Compound 27]
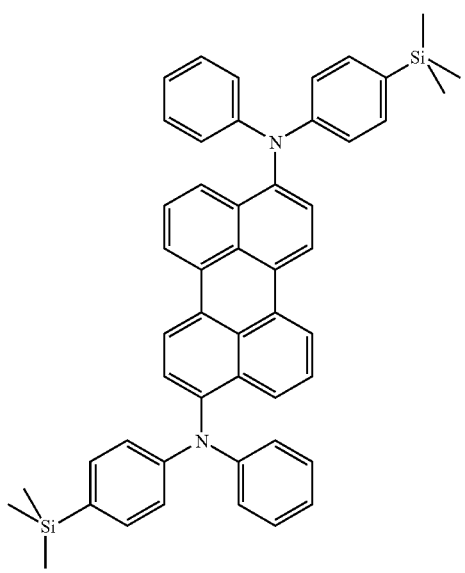

-continued
[Compound 28]
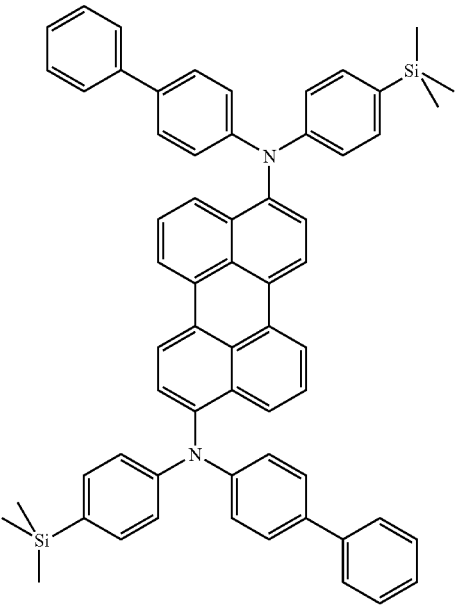
[Compound 29]
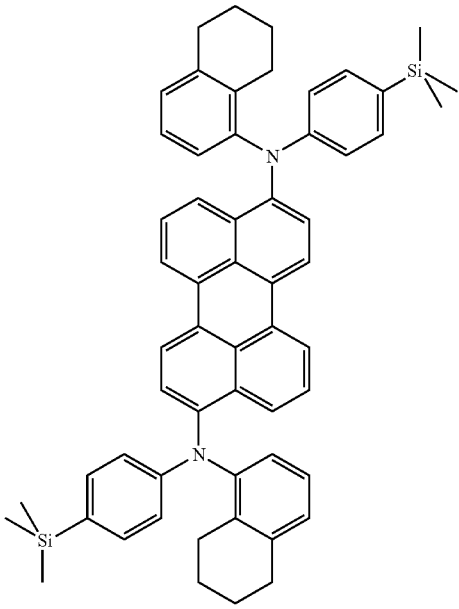
[Compound 30]
[Compound 31]
[Compound 32]
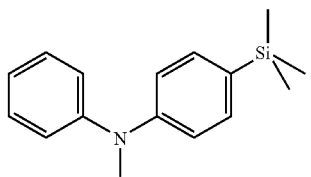
[Compound 33]
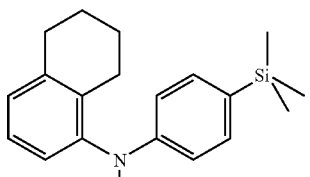

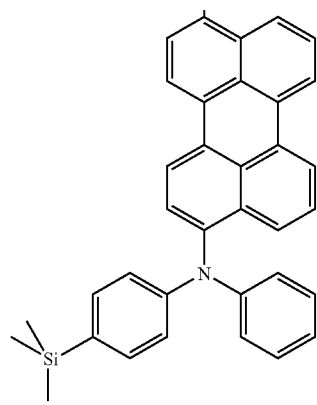
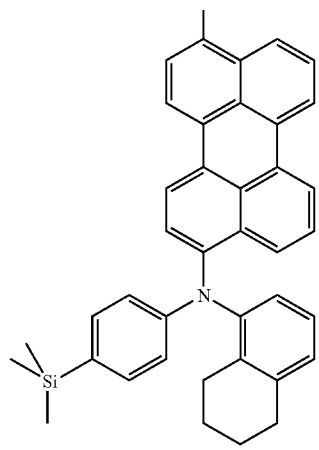
[Compound 34]
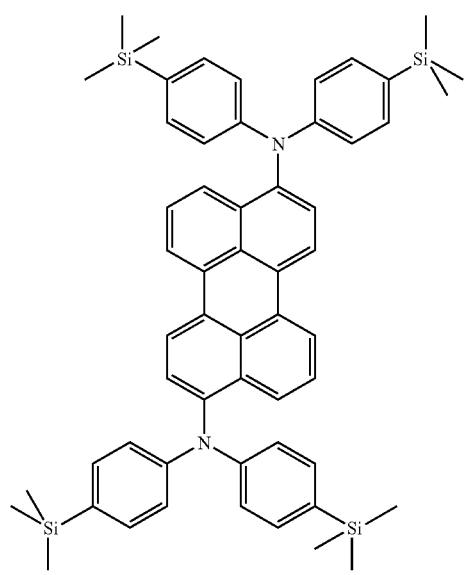
[Compound 35]
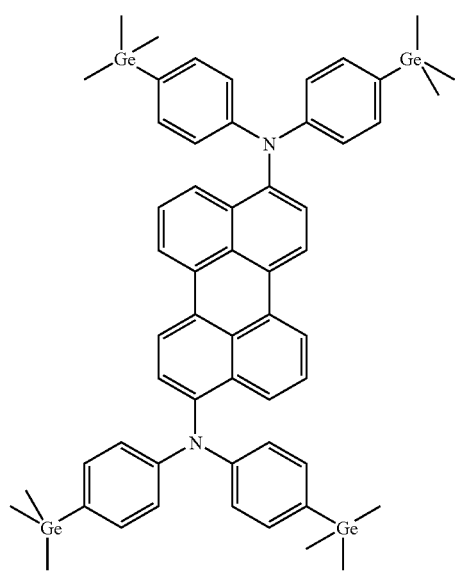
[Compound 36]
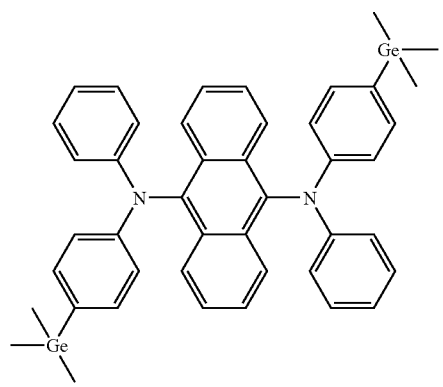
[Compound 37]
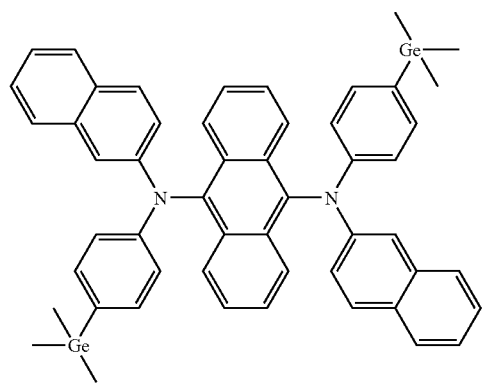

-continued
[Compound 38]
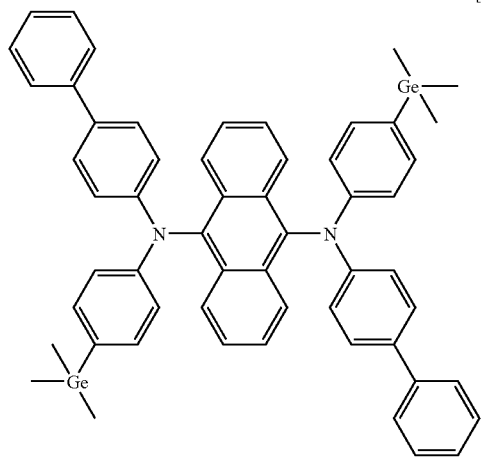
[Compound 39]
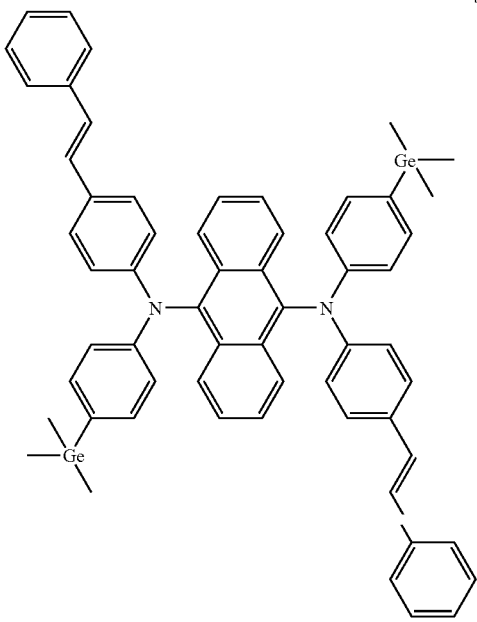
[Compound 40]
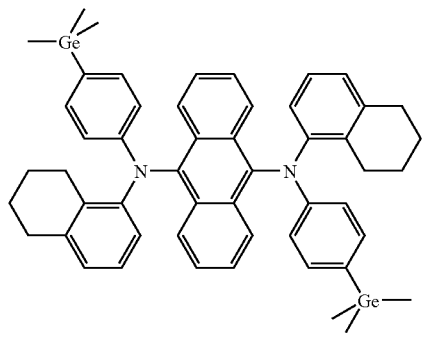
[Compound 41]
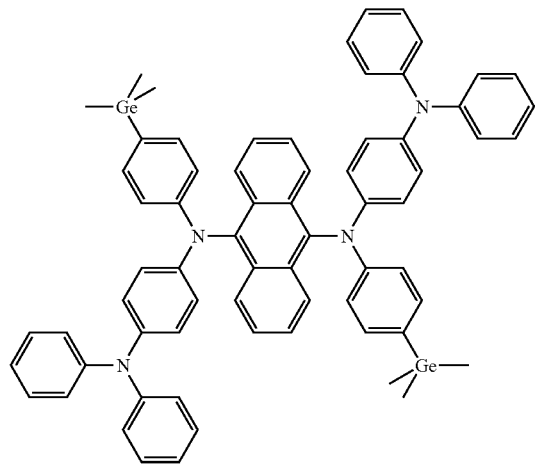
[Compound 42]
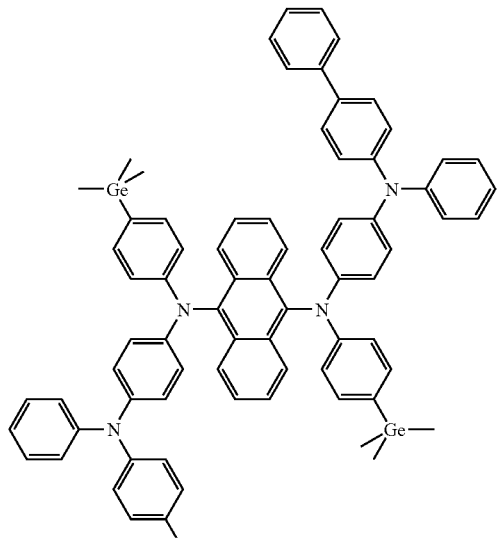
[Compound 43]
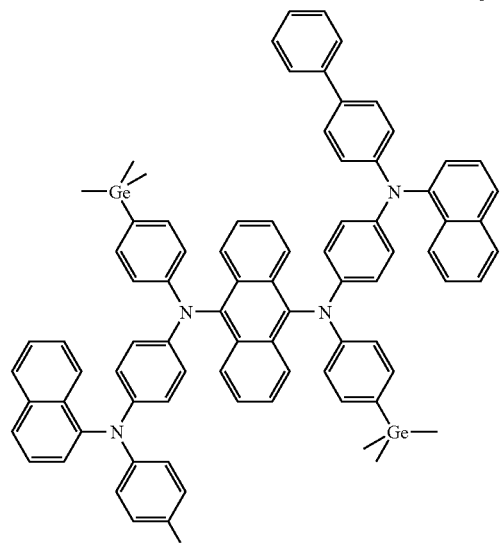

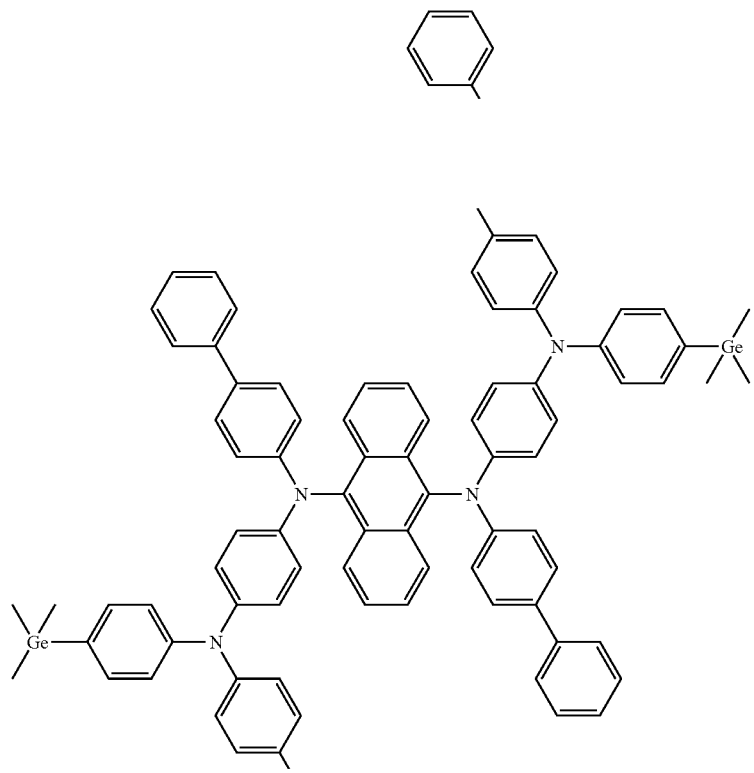
[Compound 44]
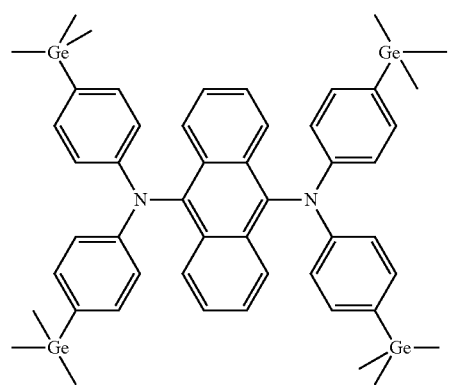
[Compound 51]
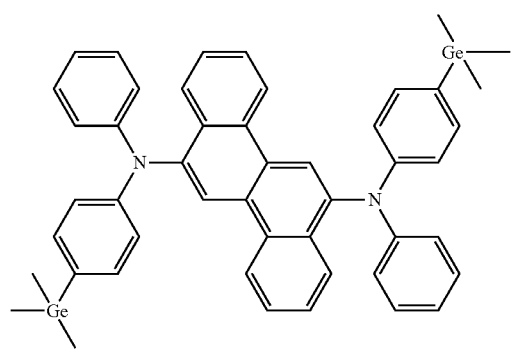
[Compound 52]

[Compound 53]
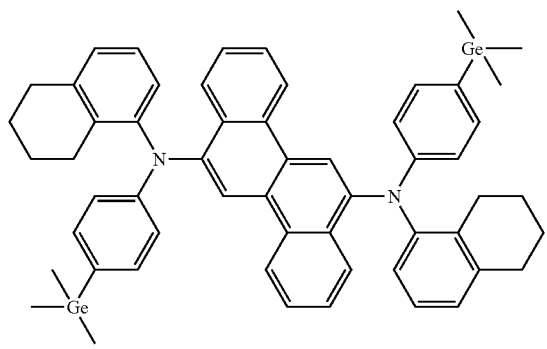
[Compound 54]
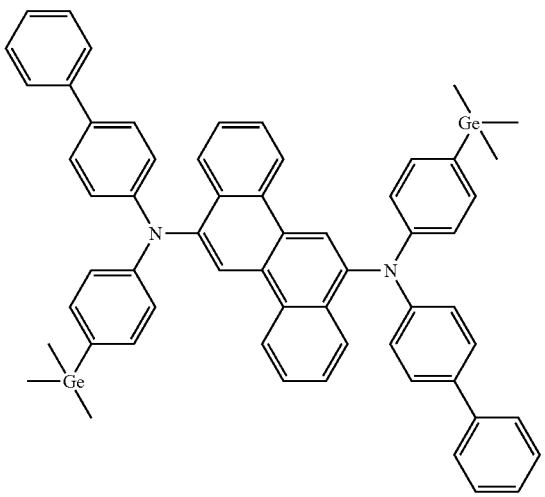
[Compound 55]
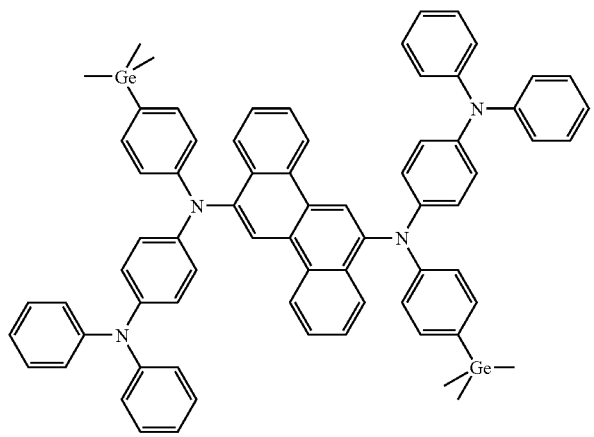
[Compound 56]
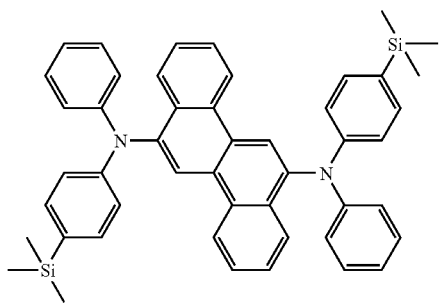
[Compound 57]
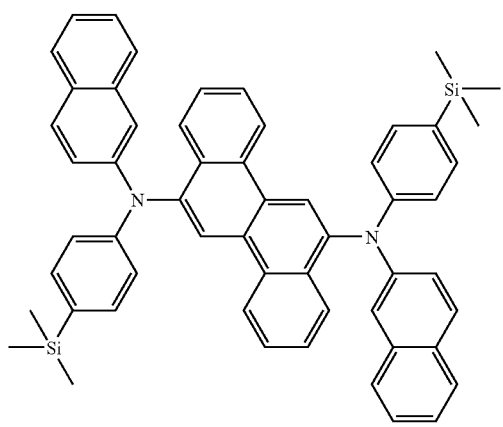
[Compound 58]
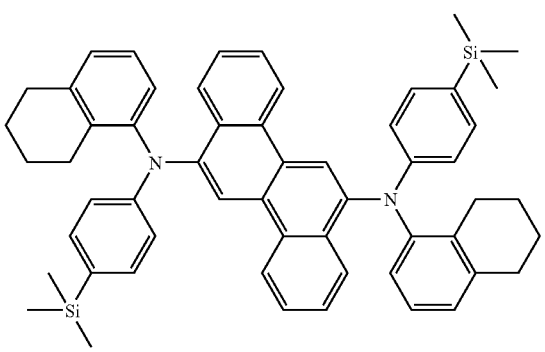

-continued
[Compound 59]
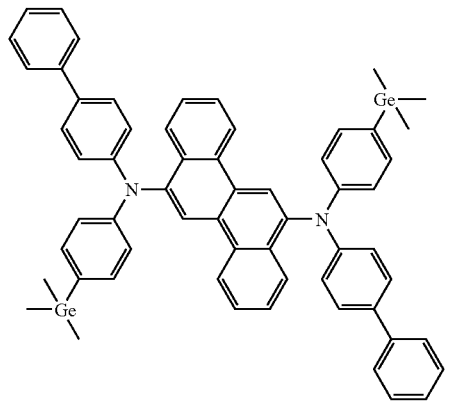
[Compound 60]
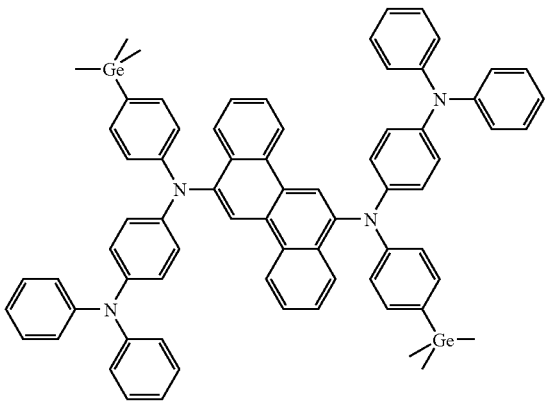
[Compound 61]
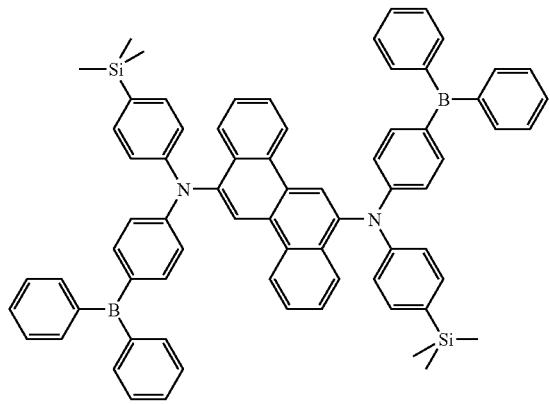
[Compound 62]
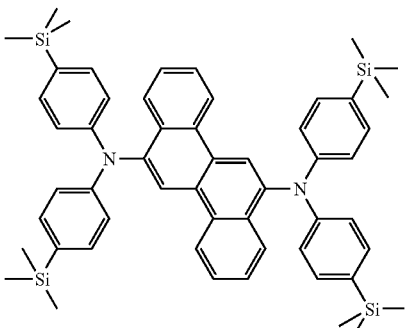
[Compound 63]
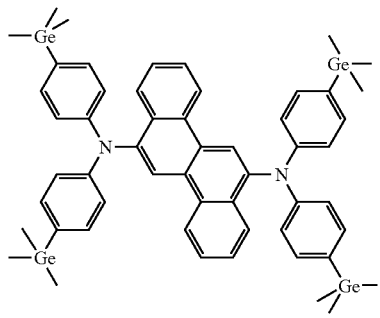
[Compound 64]
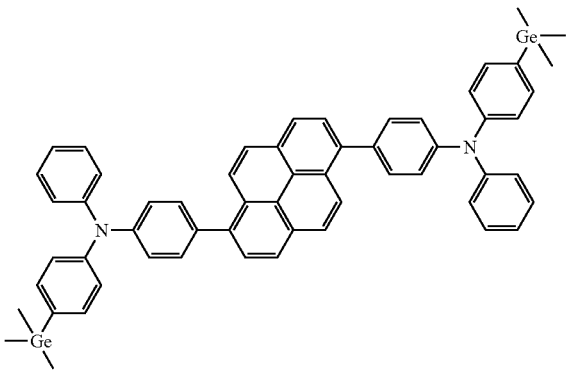
[Compound 65]
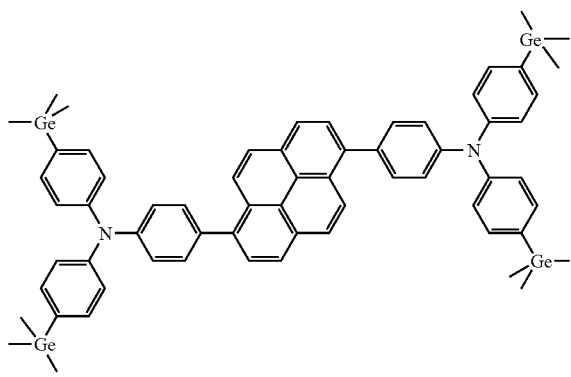
[Compound 66]
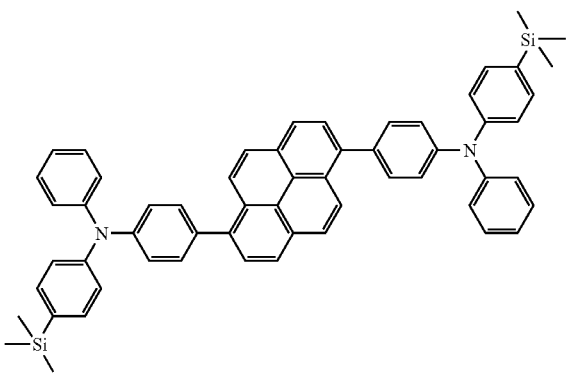

[Compound 67]
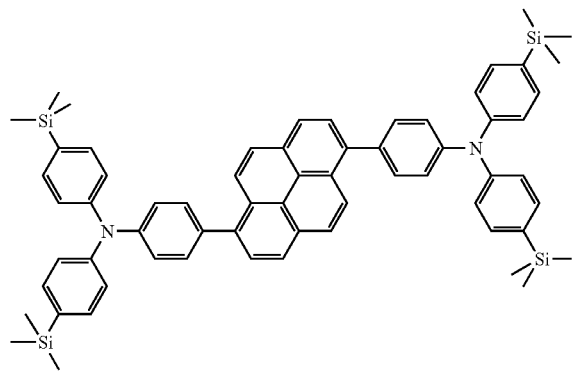
[Compound 68]
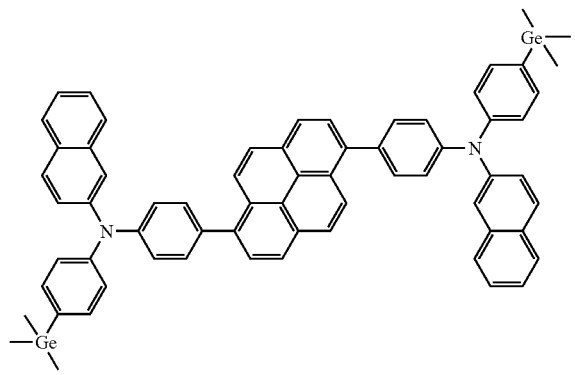
[Compound 69]
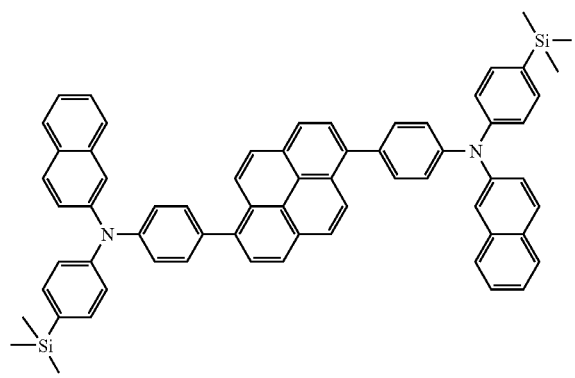
[Compound 70]
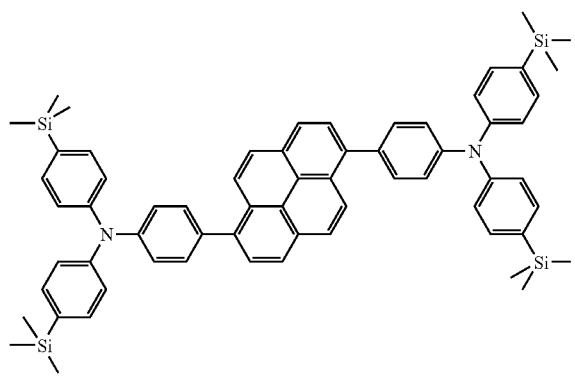
[Compound 71]
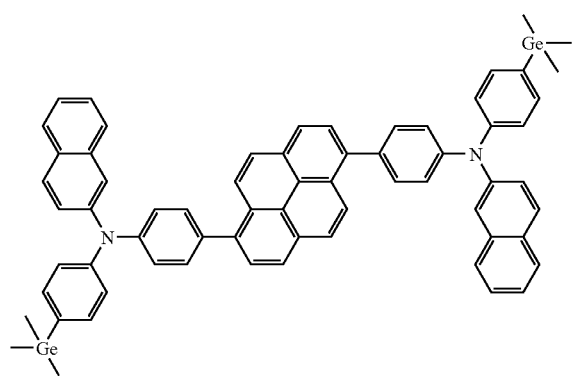
[Compound 72]
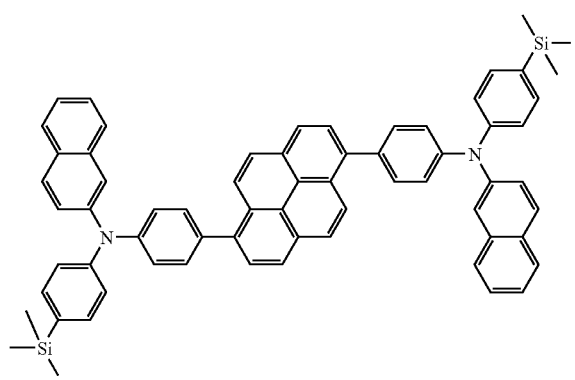

-continued
[Compound 73]
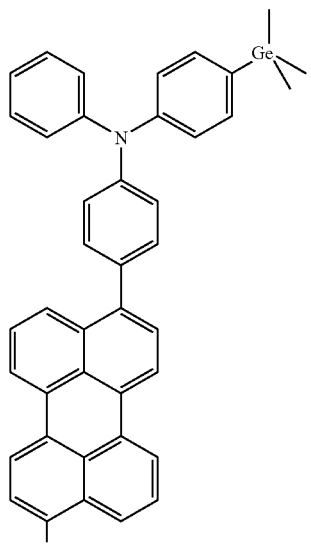
[Compound 74]
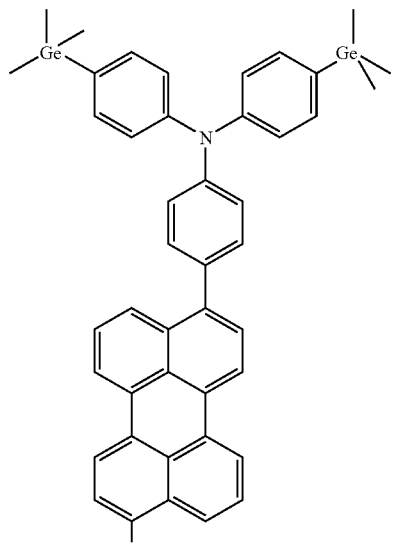
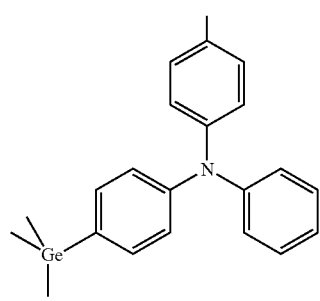
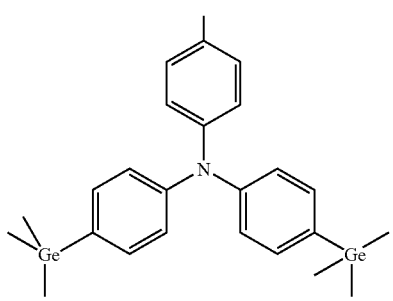
[Compound 75]
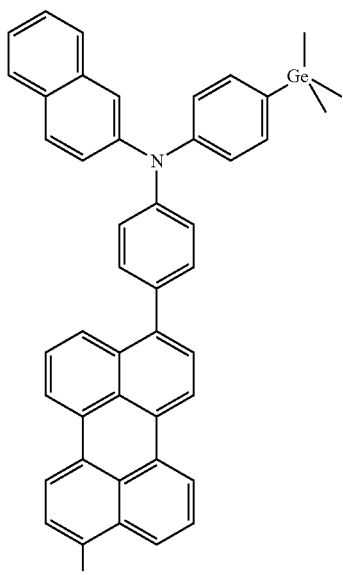
[Compound 76]
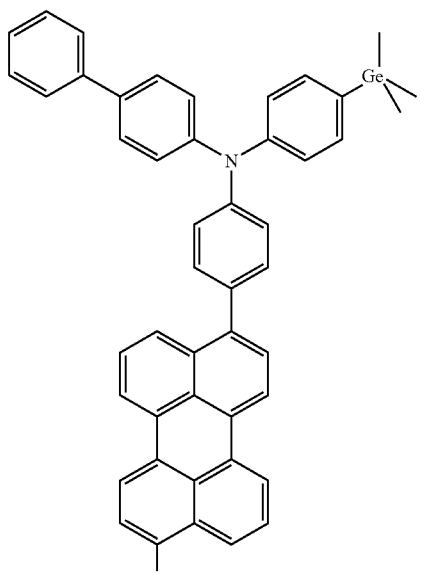

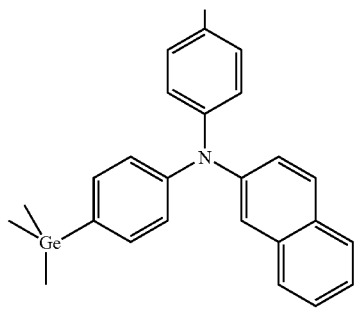
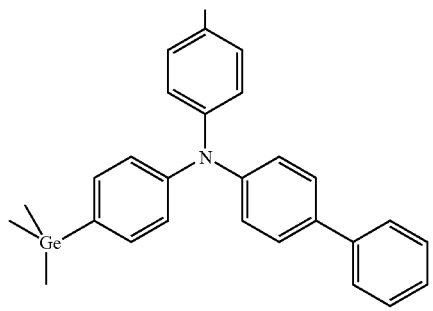
[Compound 77]
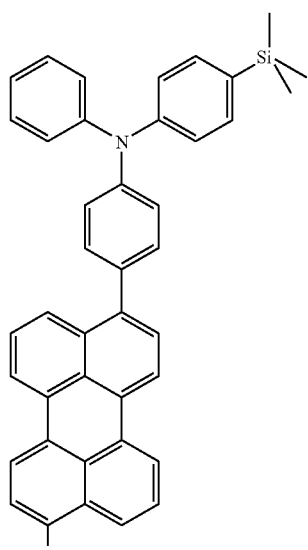
[Compound 78]
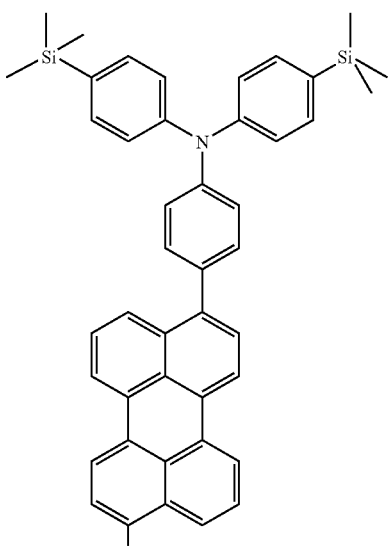
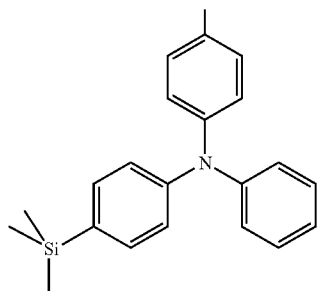
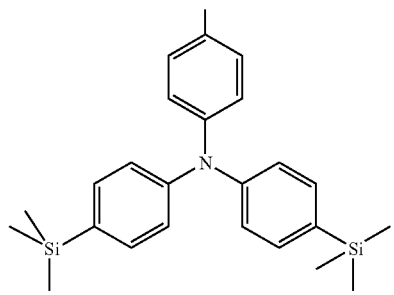

-continued
[Compound 79]
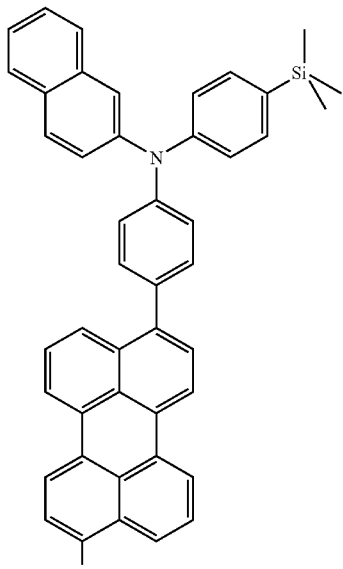
[Compound 80]
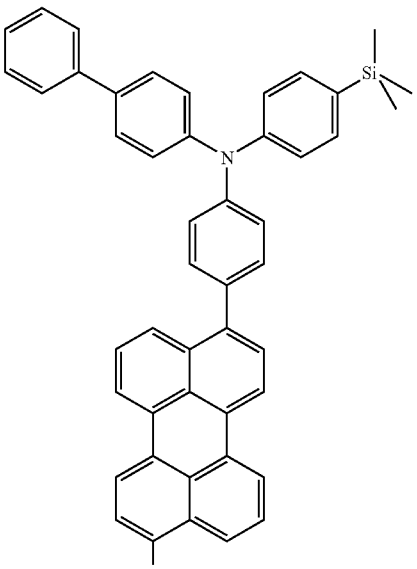
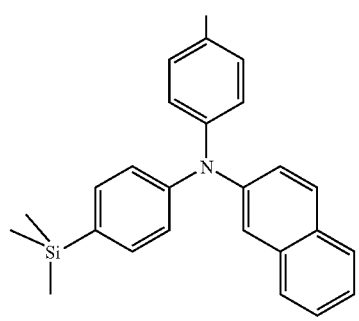
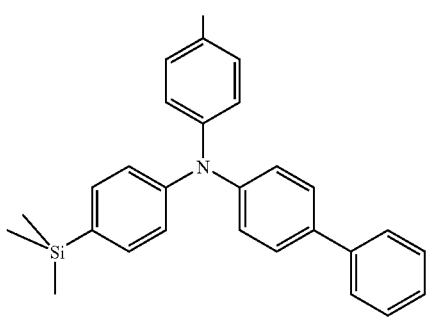
[Compound 81]
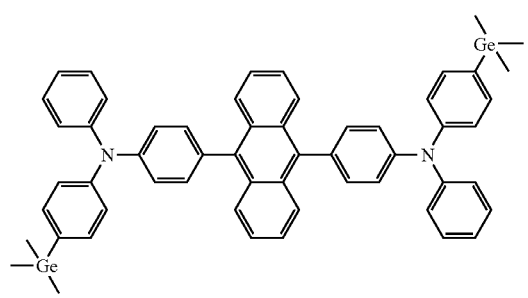
[Compound 82]
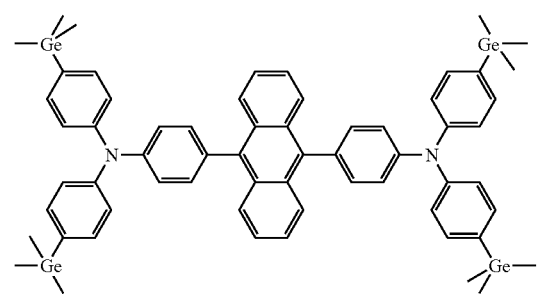
[Compound 83]
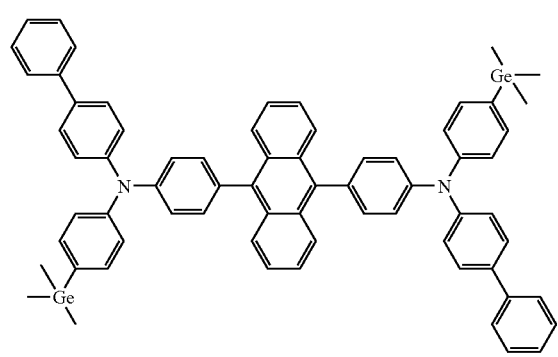
[Compound 84]
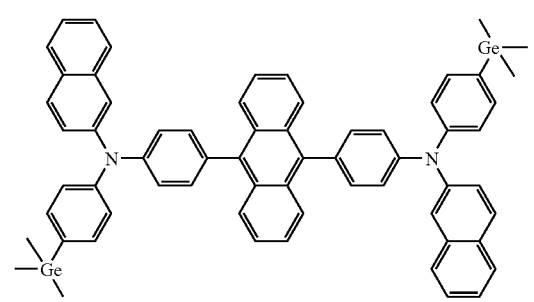

-continued
[Compound 85]
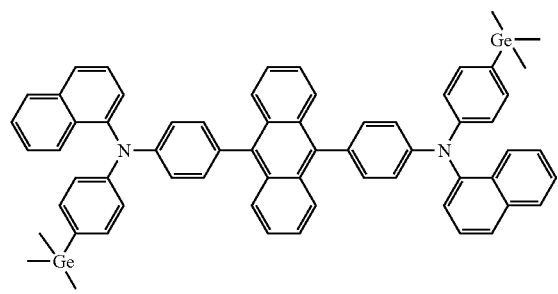
[Compound 86]
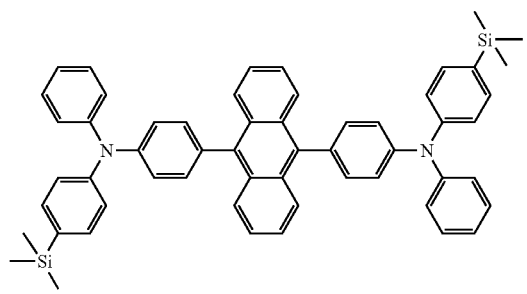
[Compound 87]
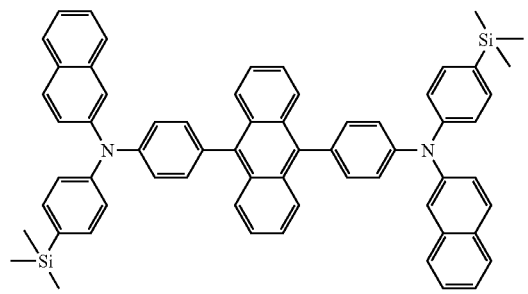
[Compound 88]
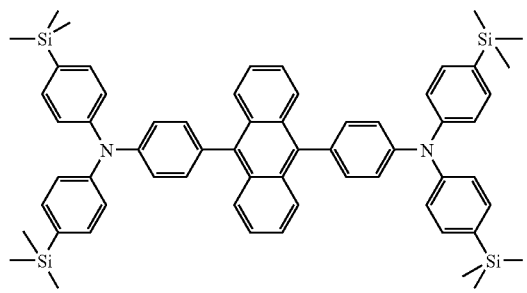
[Compound 89]
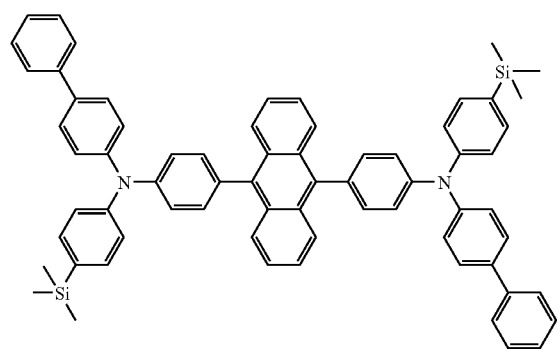
[Compound 90]
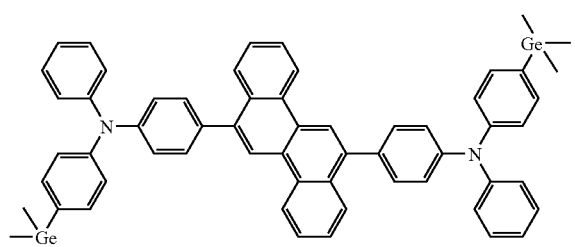
[Compound 91]
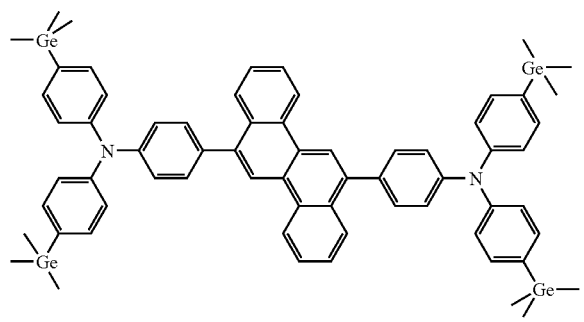
[Compound 92]
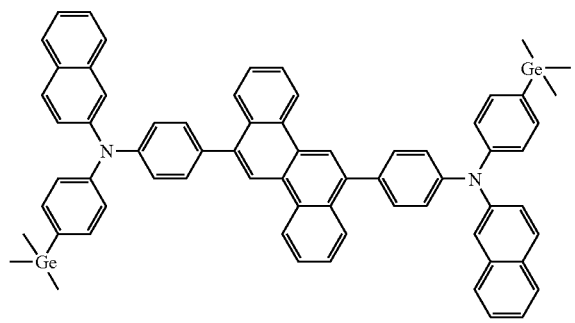

[Compound 93]
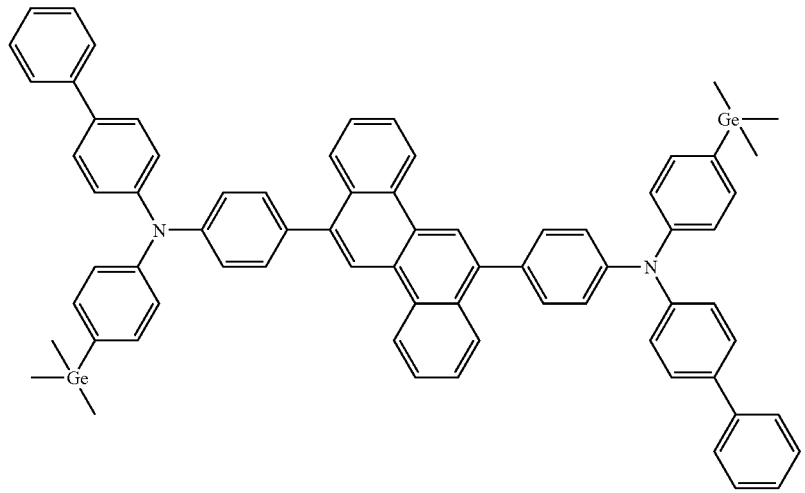
[Compound 94]
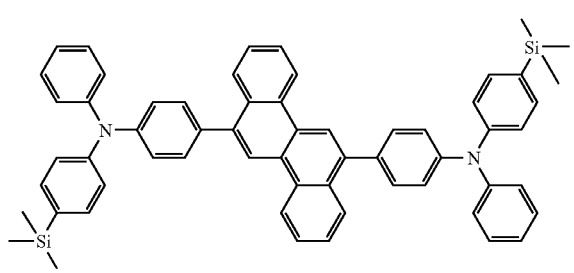
[Compound 95]
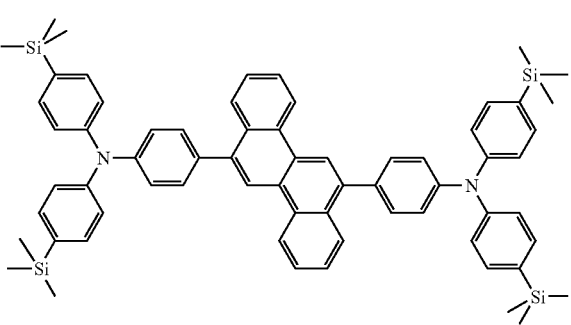
[Compound 96]
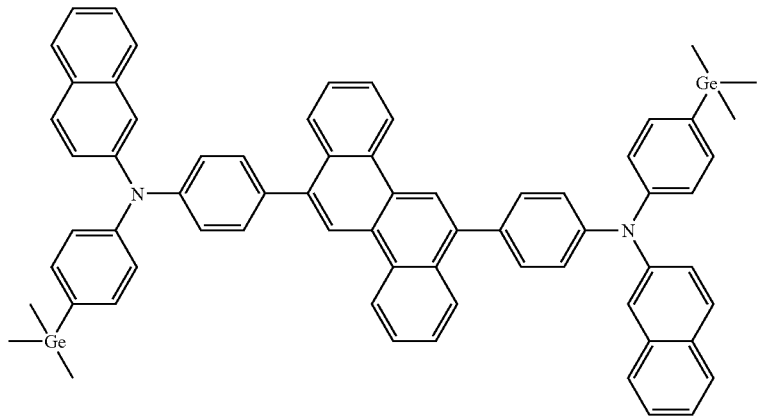

[Compound 97]
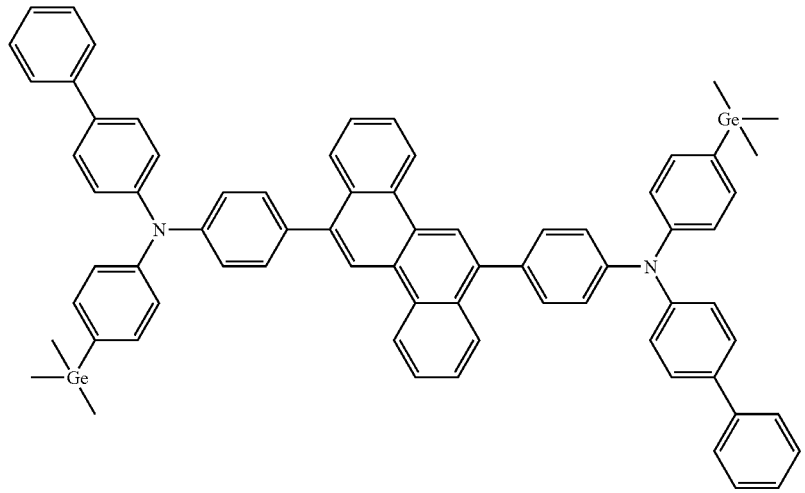
[Compound 119]
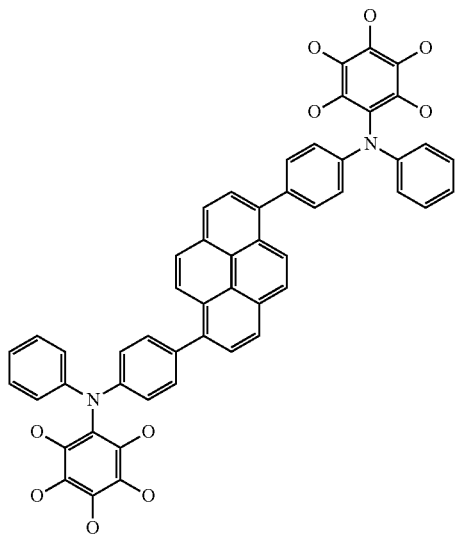
[Compound 120]
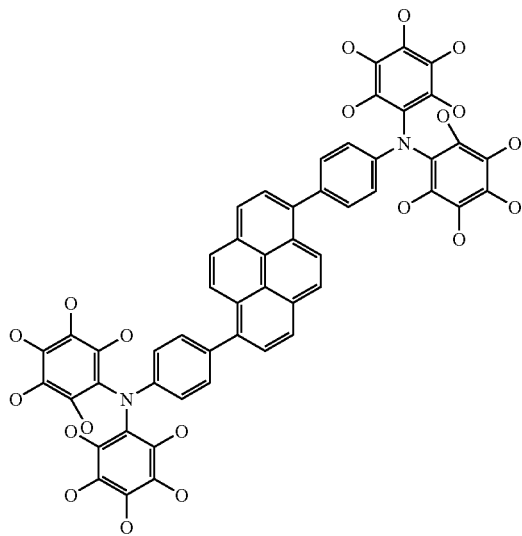
[Compound 121]
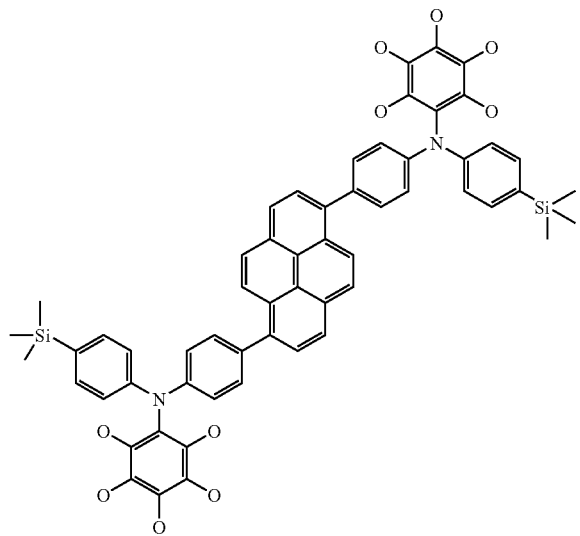

[Compound 122]
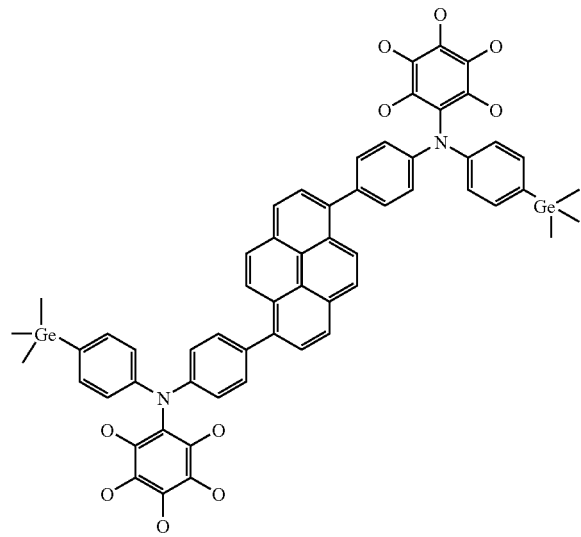
[Compound 123]
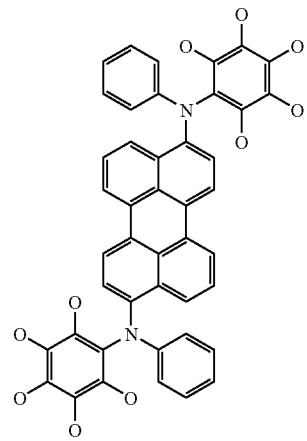
[Compound 124]
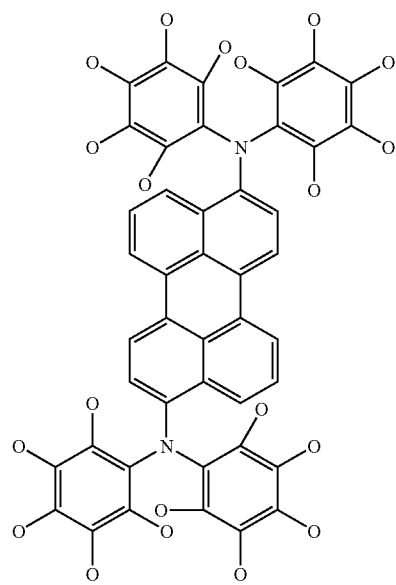
[Compound 125]
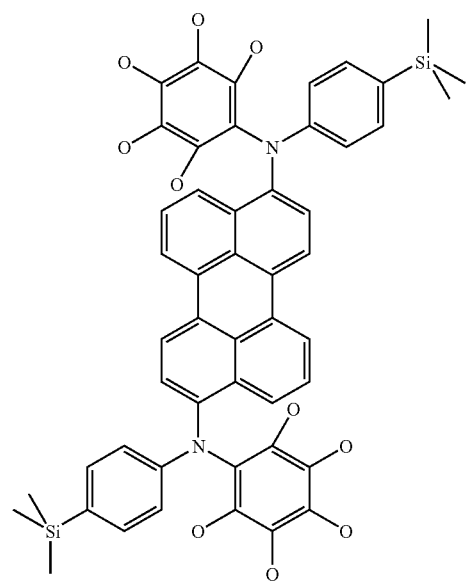

-continued
[Compound 126]
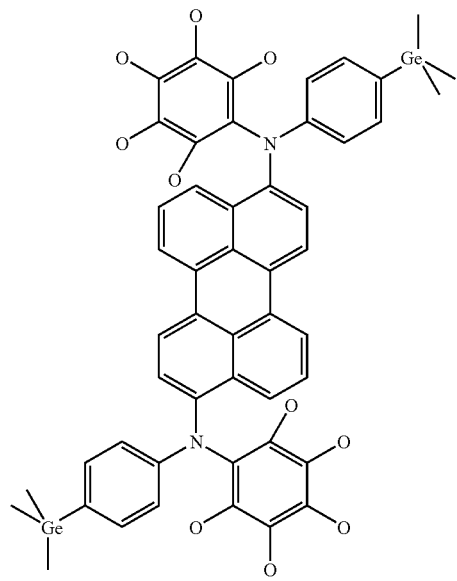
[Compound 127]
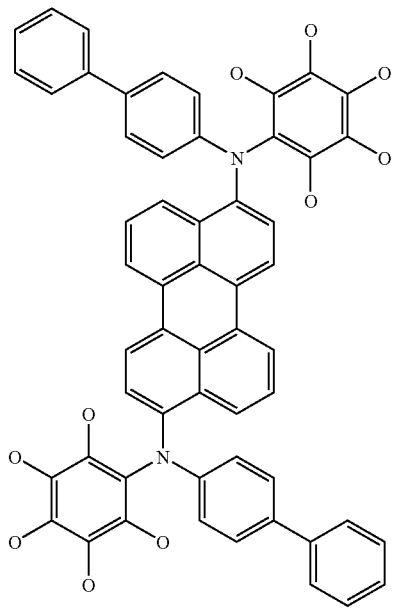
[Compound 128]
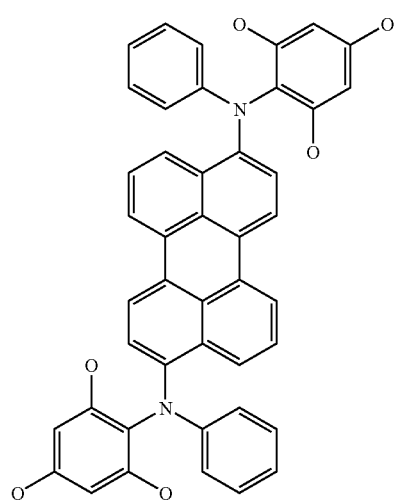
[Compound 129]
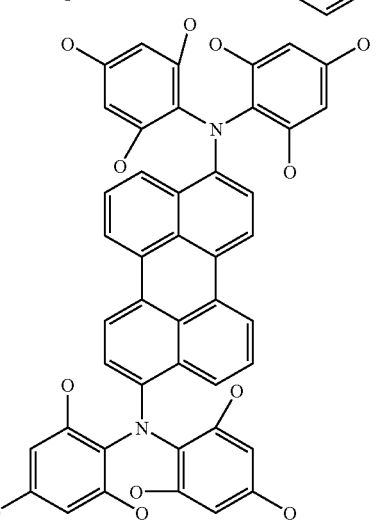
[Compound 130]
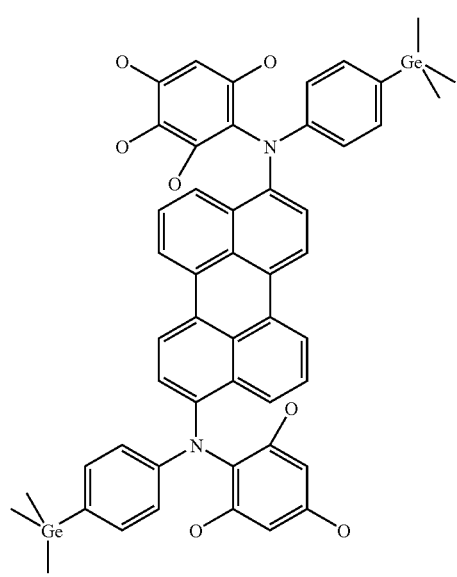
[Compound 131]
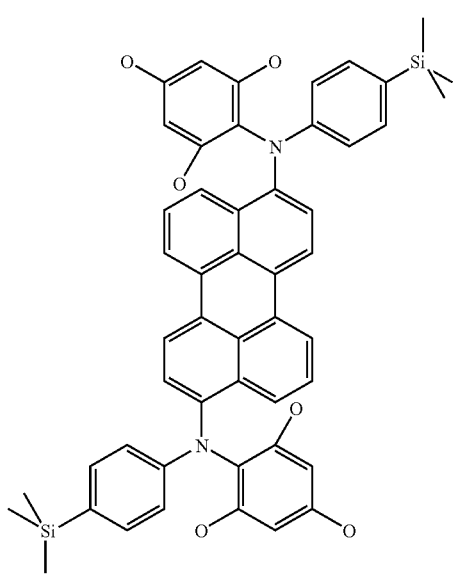

[Compound 132]
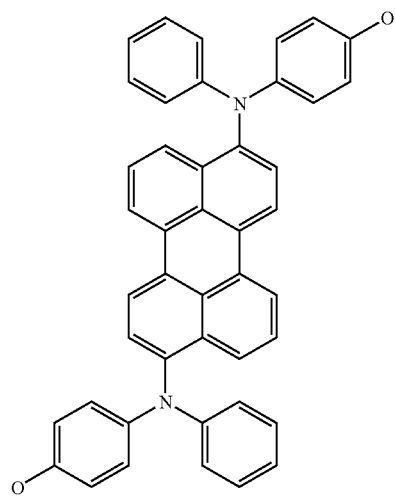
[Compound 133]
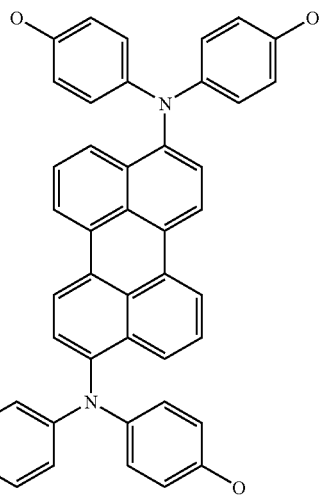
[Compound 134]
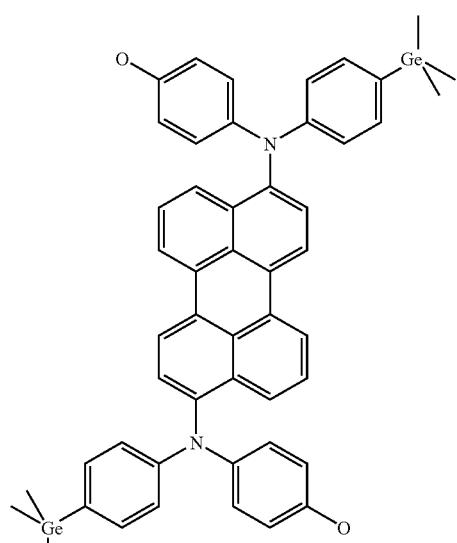
[Compound 135]
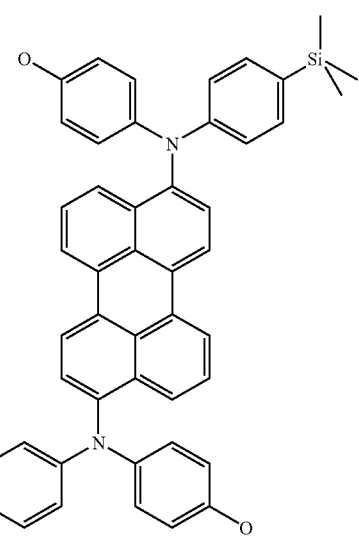
[Compound 136]
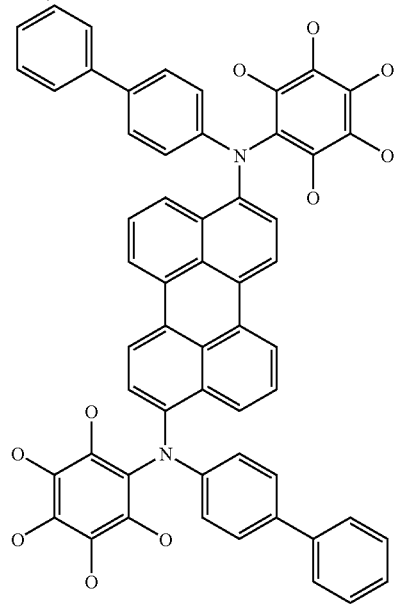
[Compound 137]
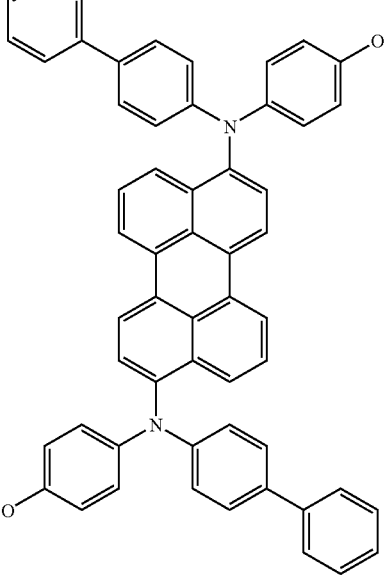

-continued
[Compound 138]
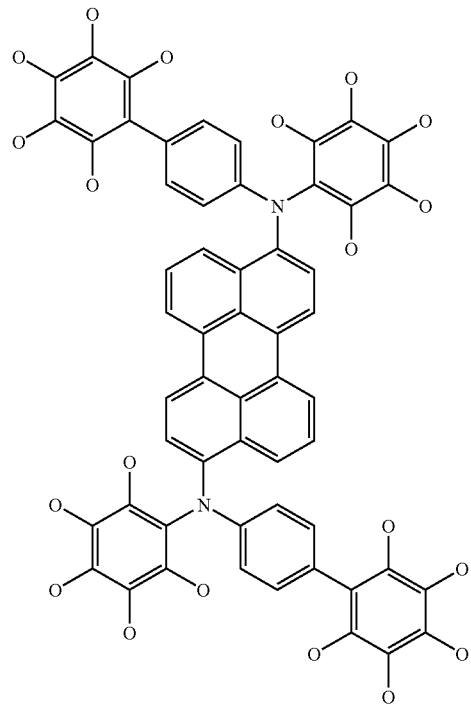
[Compound 139]
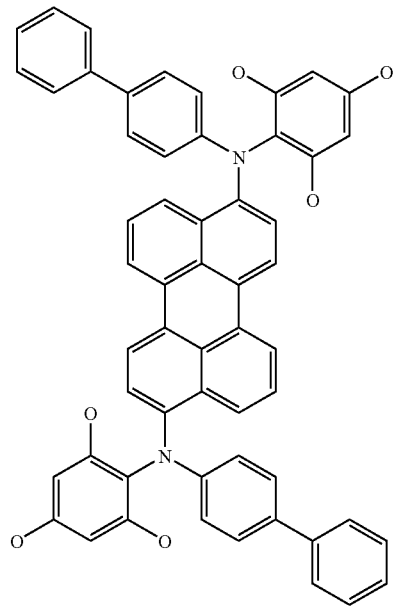
[Compound 140]
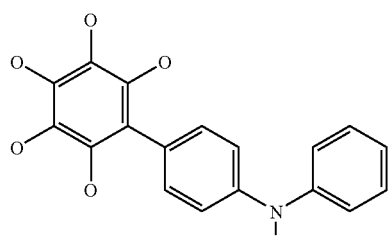
[Compound 141]
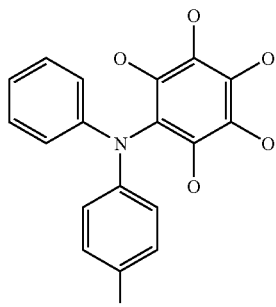
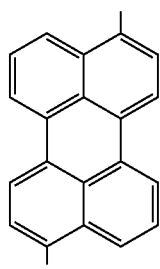
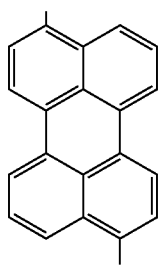
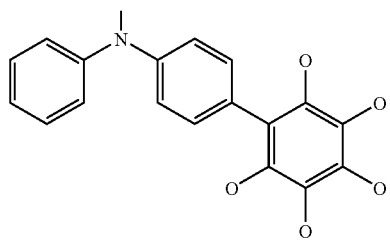
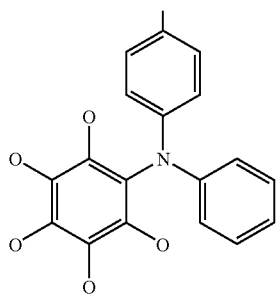

-continued
[Compound 142]
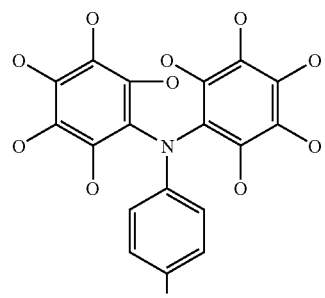
[Compound 143]
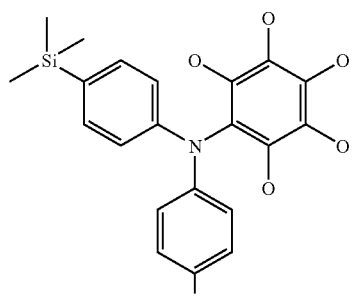
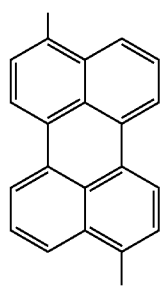
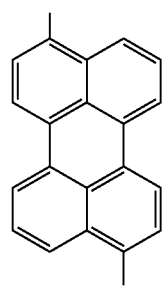
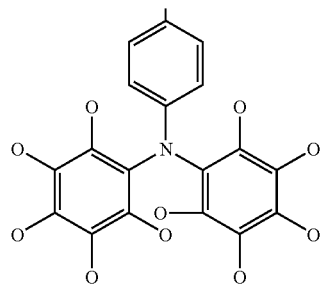
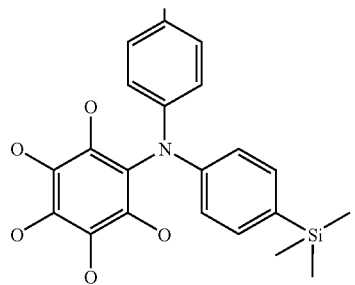
[Compound 144]
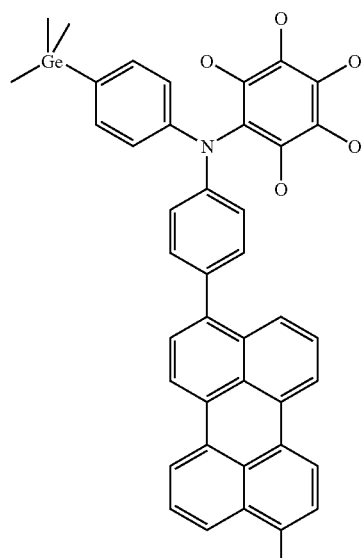
[Compound 145]
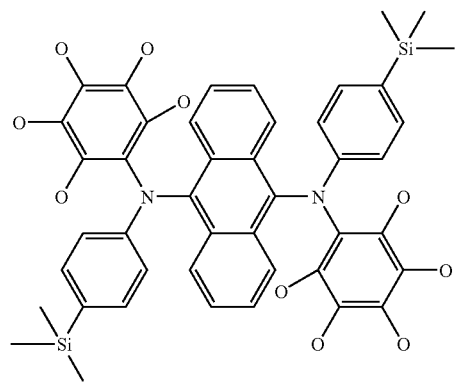

-continued
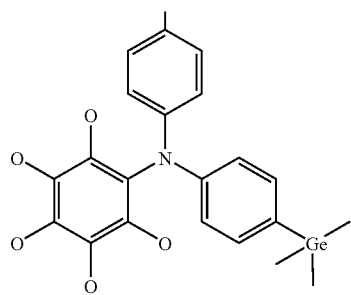
[Compound 146]
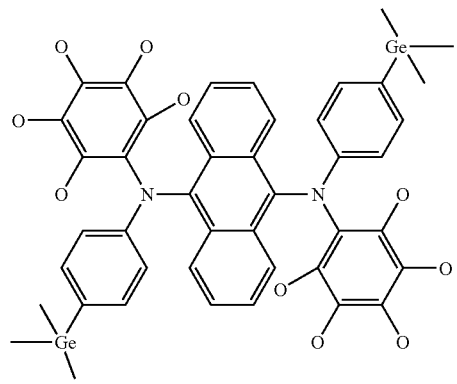
[Compound 147]
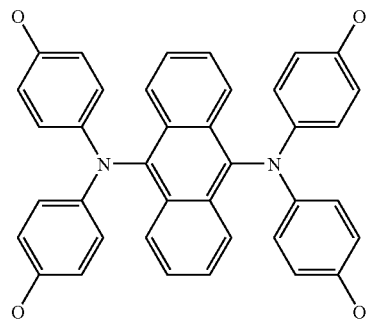
[Compound 149]
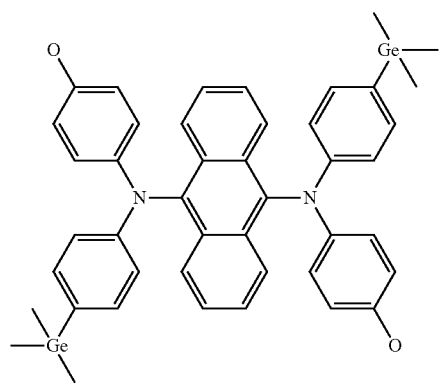
[Compound 151]
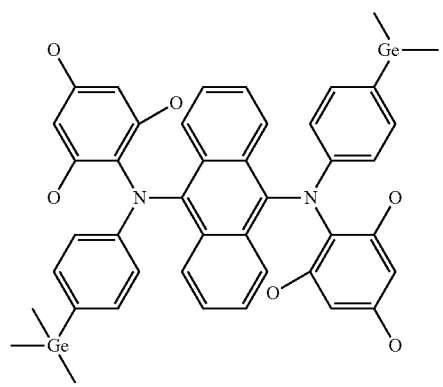
[Compound 153]
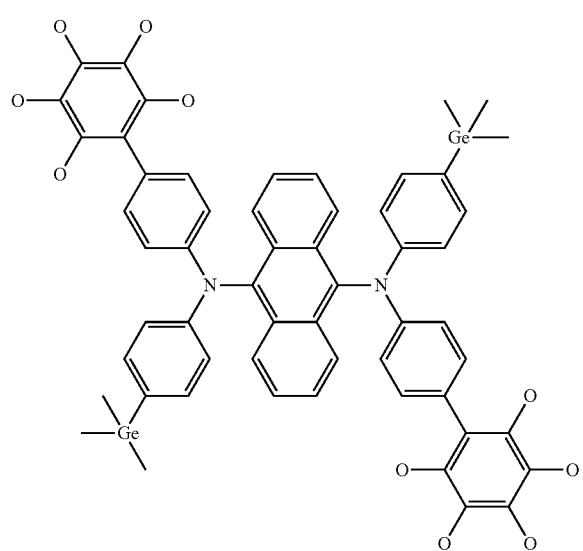
[Compound 154]
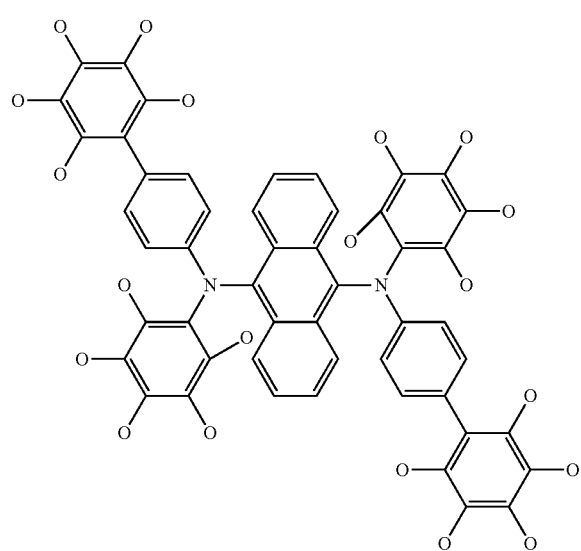

[Compound 155]
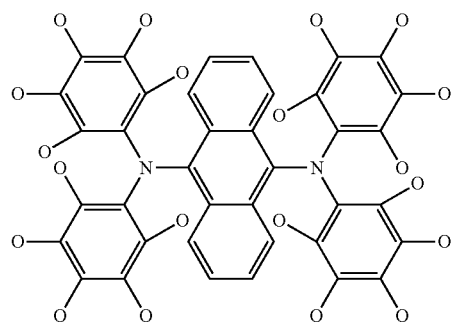
[Compound 156]
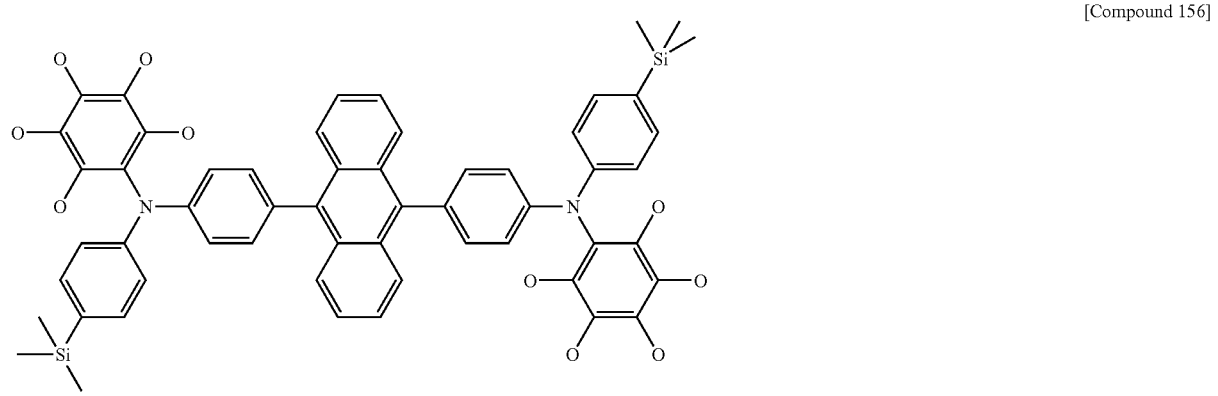
[Compound 157]
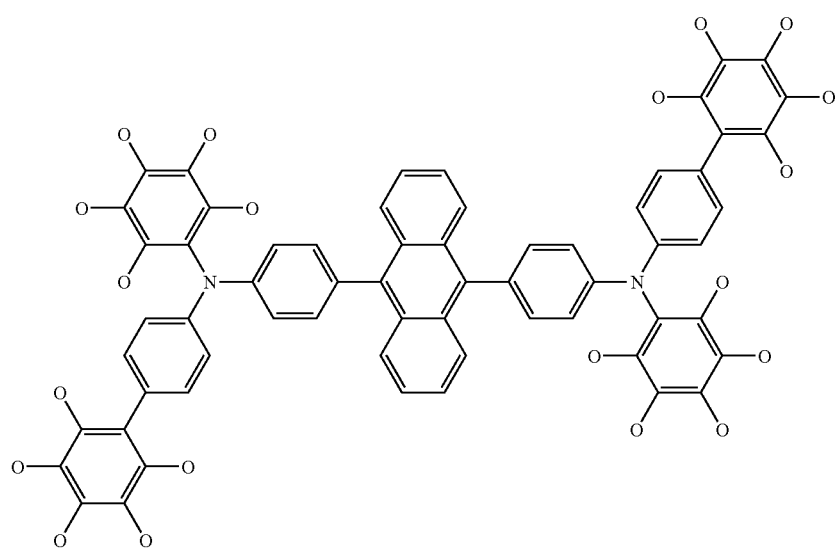
[Compound 158]
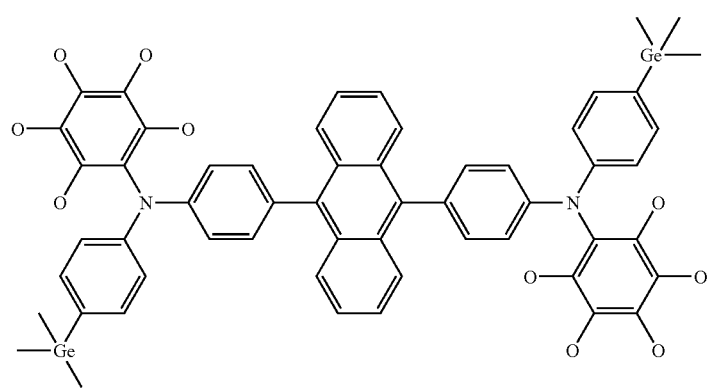

[Compound 159]
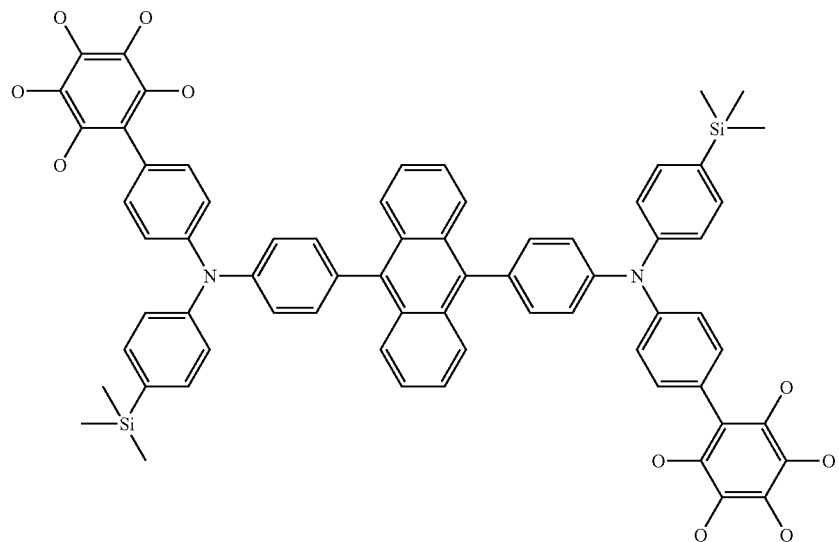
[Compound 160]
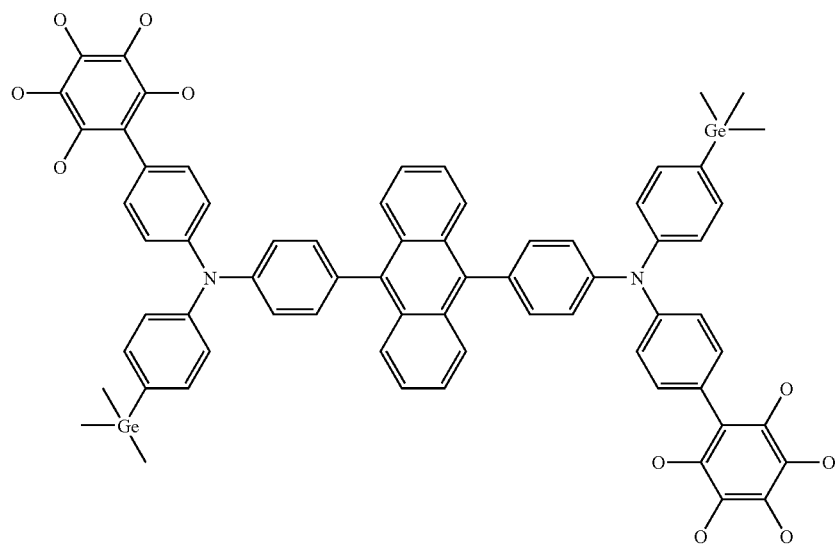
[Compound 161]
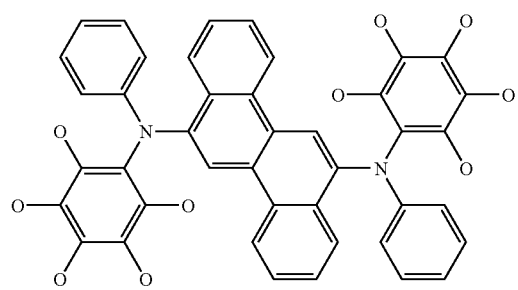
[Compound 162]
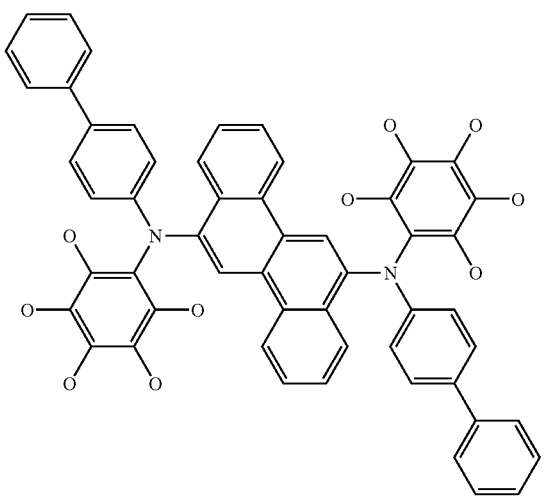

[Compound 163]
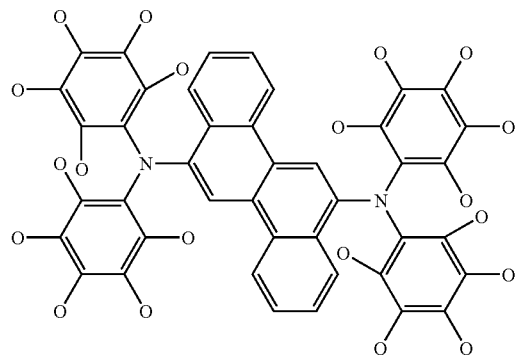
[Compound 164]
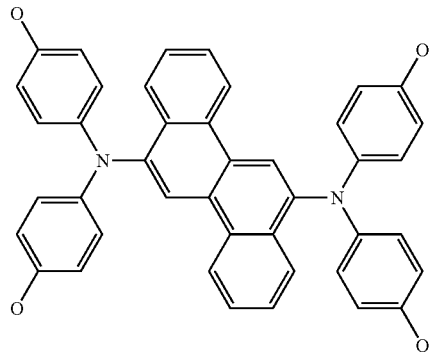
[Compound 165]
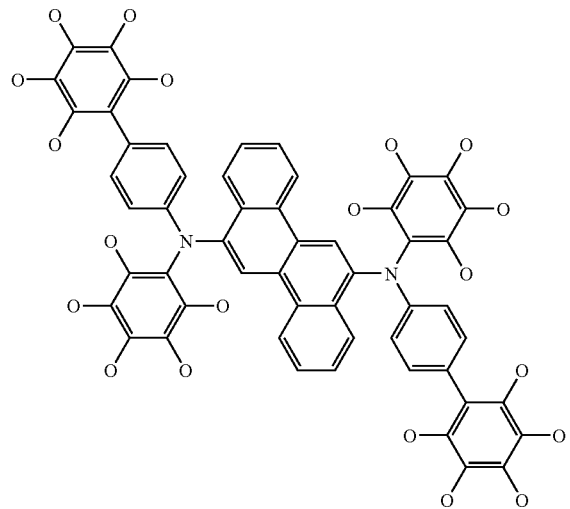
[Compound 166]
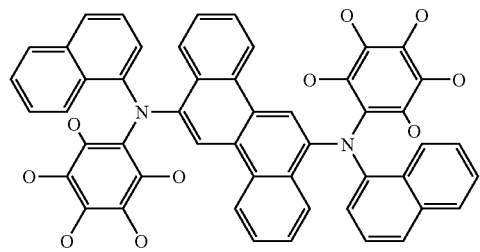
[Compound 167]
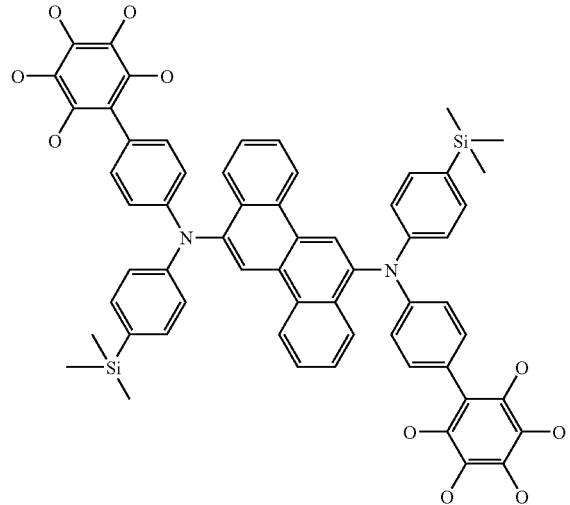
[Compound 168]
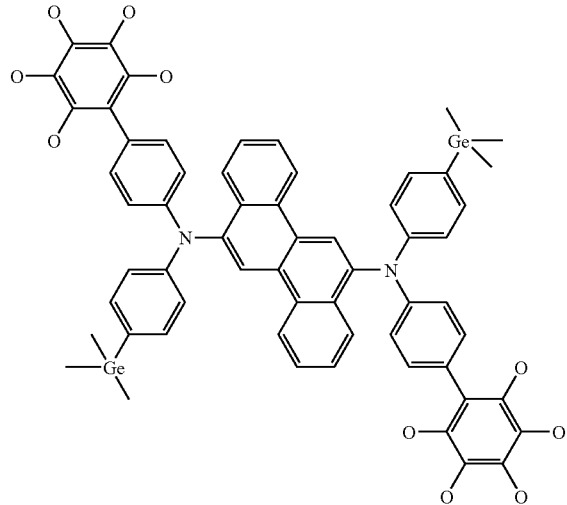

[Compound 169]
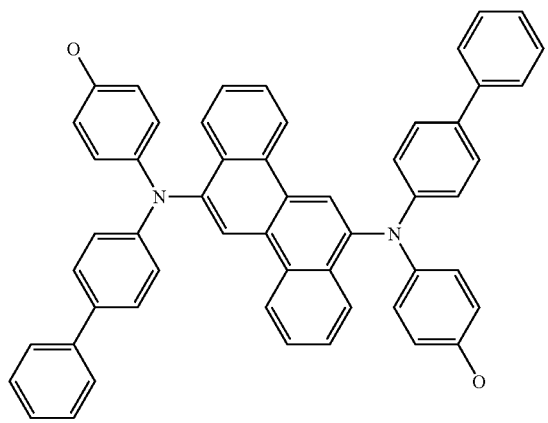
[Compound 170]
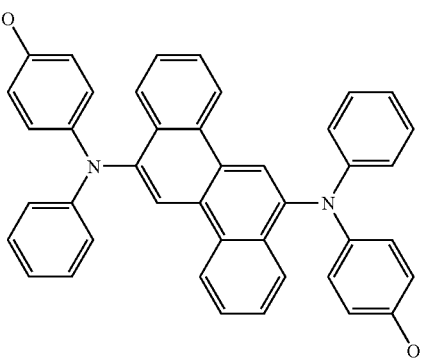
[Compound 171]
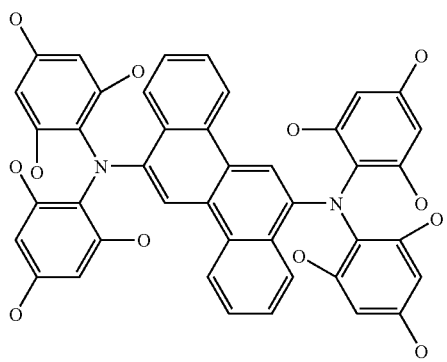
[Compound 172]
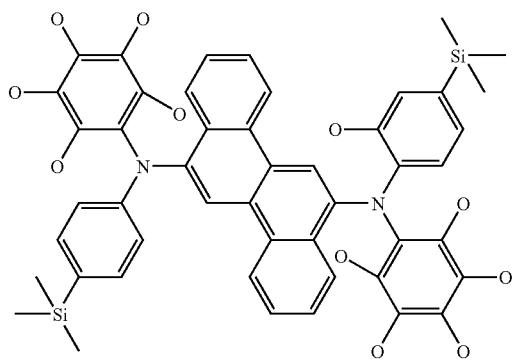
[Compound 173]
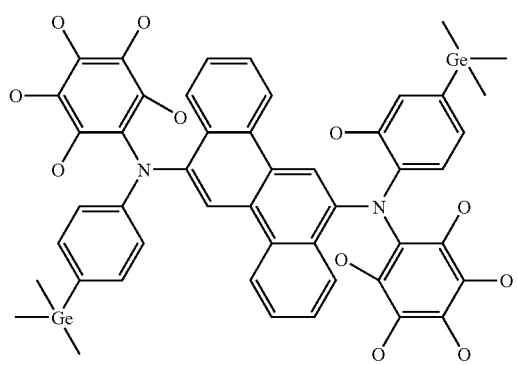
[Compound 174]
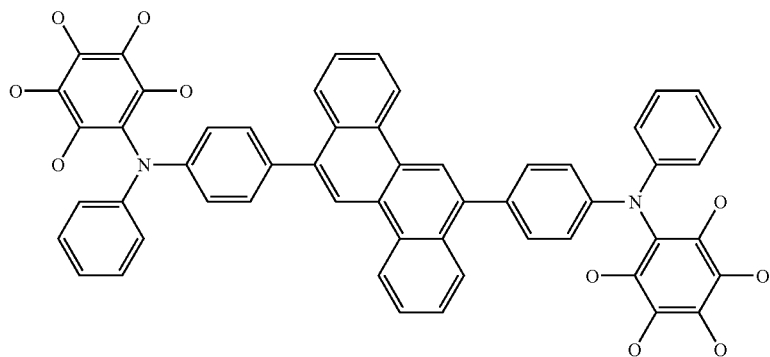

[Compound 175]
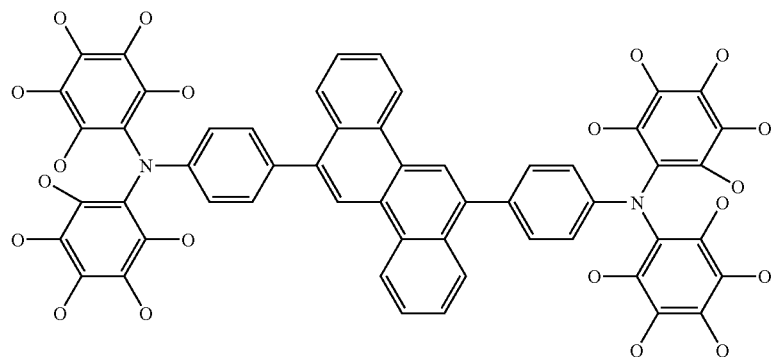
[Compound 176]
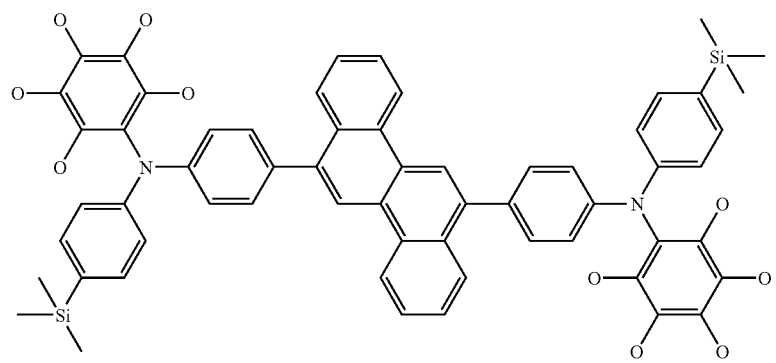
[Compound 177]
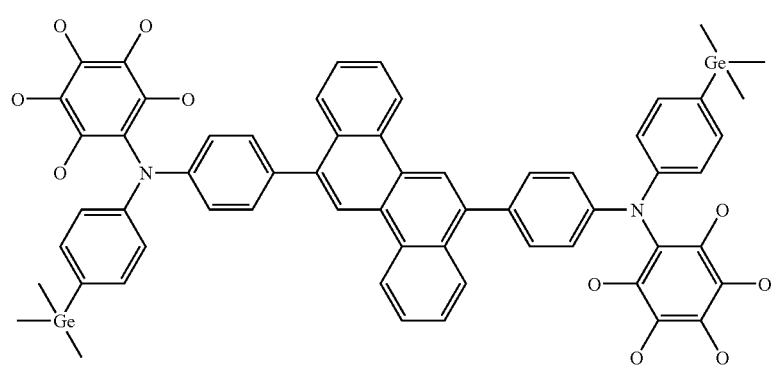
[Compound 178]
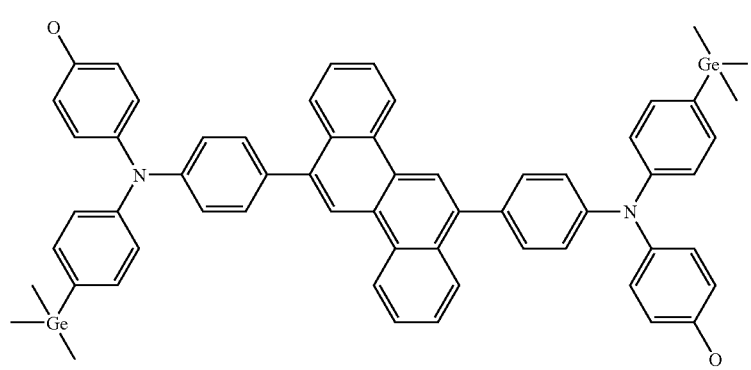

[Compound 179]
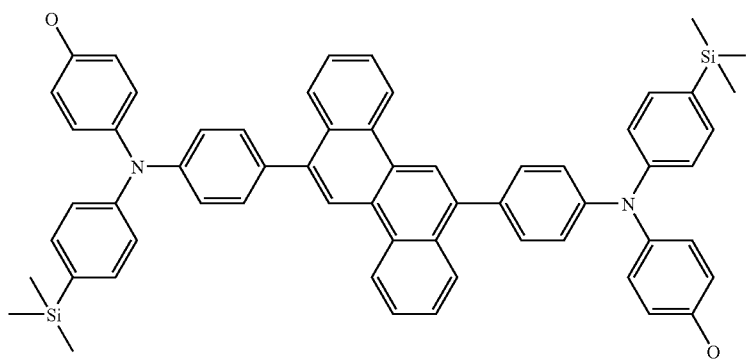
[Compound 180]
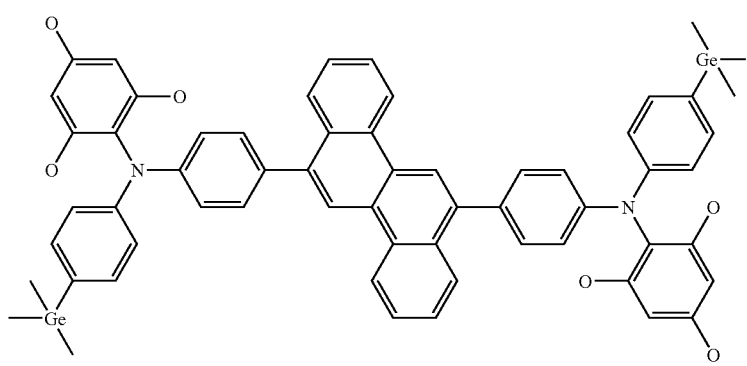
[Compound 181]
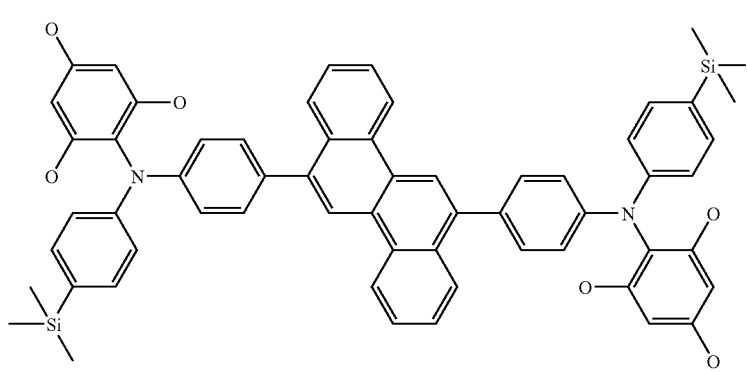
[Compound 182]
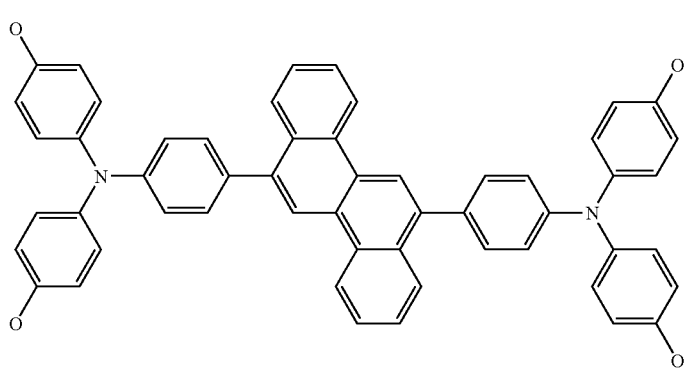

[Compound 183]
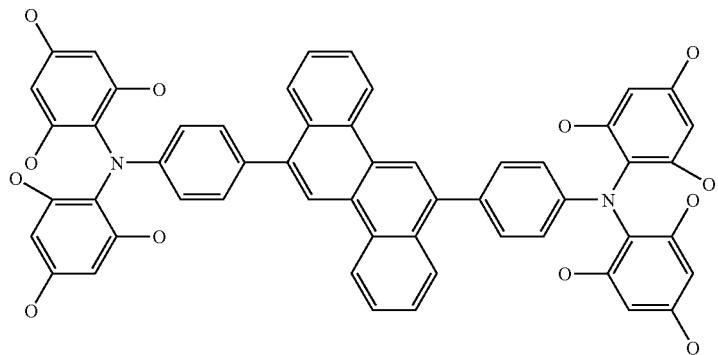
[Compound184]
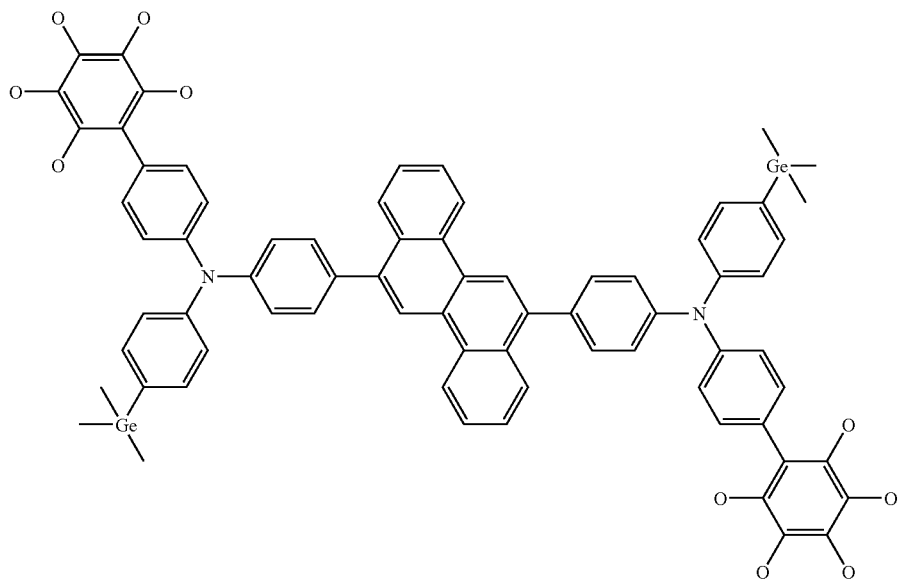
[Compound185]
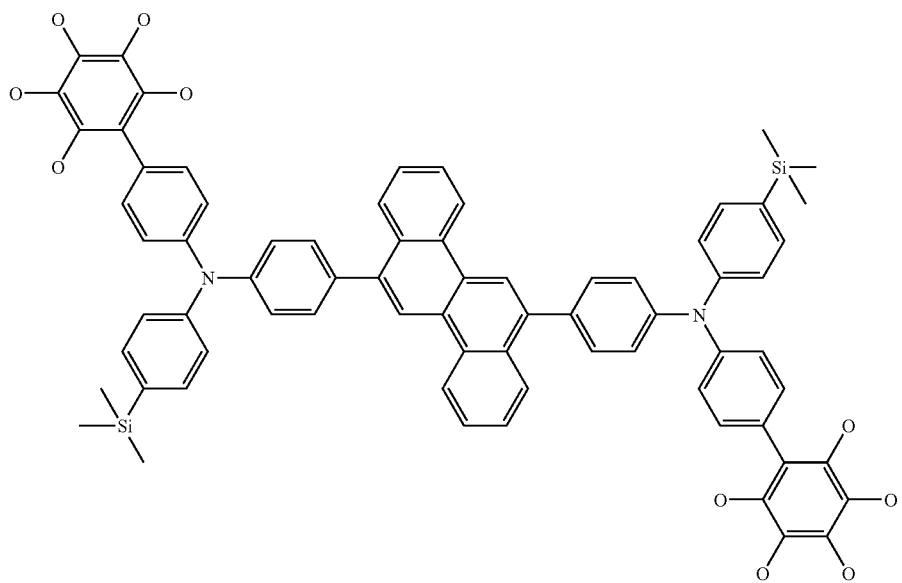

[Compound 190] 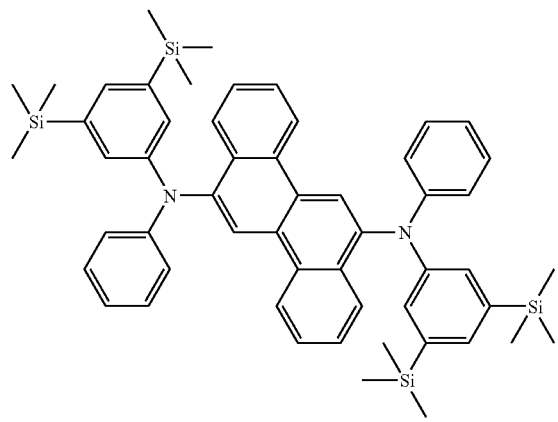
[Compound 191] 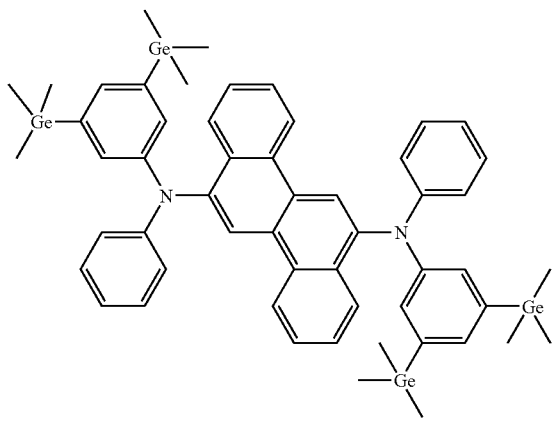
[Compound 192] 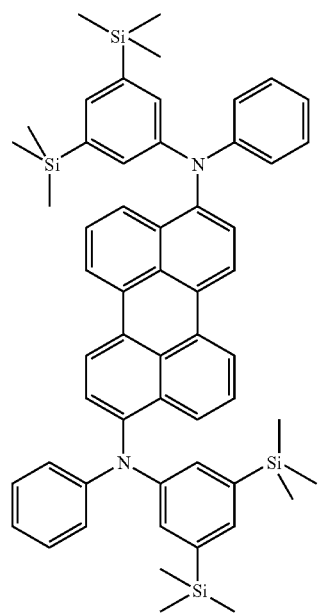
[Compound 193] 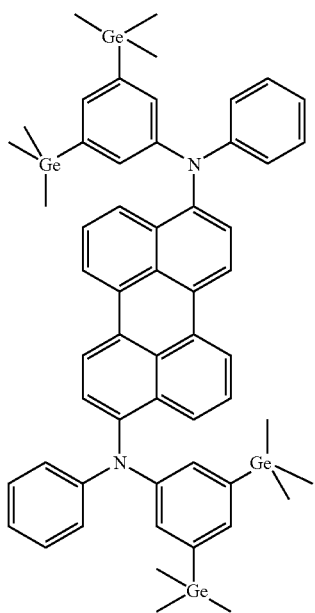
[Compound 194] 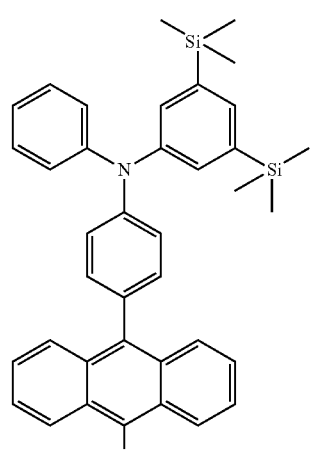
[Compound 195] 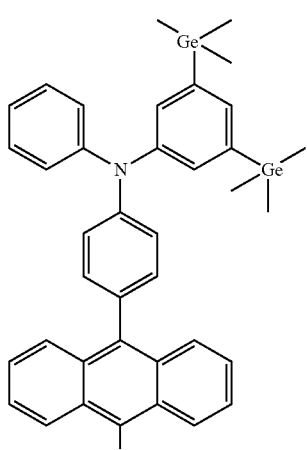

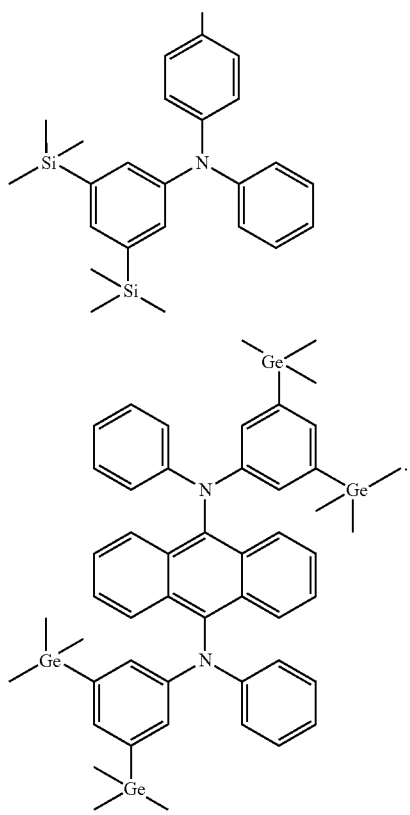

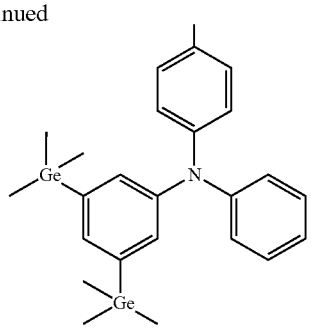

[Compound 196]

4. A method for preparing the diamine derivatie of claim 1, comprising the step of reacting a dibromoaryl compound with an arylamine compound in the presence of a palladium catalyst,
wherein the arylamine compound contains at least one selected from the group consisting of a germanium group and deuterium.

5. An organic electronic device comprising a first electrode, a second electrode, and at least one organic material layer interposed between the first electrode and the second electrode, wherein at least one layer of the organic material layers comprises the compound according to claim 1.

6. The organic electronic device according to claim 5, wherein the organic material layer comprises at least one of a hole injecting layer, a hole transporting layer, and a hole injecting and hole transporting layer, and one of the layers comprise the compound.

7. The organic electronic device according to claim 5, wherein the organic material layer comprises a light emitting layer, and the light emitting layer comprises the compound.

8. The organic electronic device according to claim 5, wherein the organic material layer comprises an electron transporting layer, and the electron transporting layer comprises the compound.

9. The organic electronic device according to claim 5, wherein the organic electronic device is selected from the group consisting of an organic light emitting device, an organic photovoltaic cell, an organic photoconductor (OPC) and an organic transistor.

10. An organic electronic device comprising a first electrode, a second electrode, and at least one organic material layer interposed between the first electrode and the second electrode, wherein at least one layer of the organic material layers comprises the compound according to claim 2.

11. The organic electronic device according to claim 10, wherein the organic electronic device is selected from the group consisting of an organic light emitting device, an organic photovoltaic cell, an organic photoconductor (OPC) and an organic transistor.

12. An organic electronic device comprising a first electrode, a second electrode and at least one organic material layer interposed between the first electrode and the second electrode wherein at least one layer of the organic material layers comprises the compound according to claim 3.

13. The organic electronic device according to claim 12, wherein the organic electronic device is selected from the group consisting of an organic light emitting device. an organic photovoltaic cell, an organic photoconductor (OPC) and an organic transistor.

* * * * *